US007666592B2

(12) United States Patent
Ecker et al.

(10) Patent No.: US 7,666,592 B2

(45) Date of Patent: Feb. 23, 2010

(54) METHODS FOR CONCURRENT IDENTIFICATION AND QUANTIFICATION OF AN UNKNOWN BIOAGENT

(75) Inventors: David J. Ecker, Encinitas, CA (US); Rangarajan Sampath, San Diego, CA (US); Lawrence B. Blyn, Mission Viejo, CA (US); Steven A. Hofstadler, Oceanside, CA (US); Thomas A. Hall, Oceanside, CA (US)

(73) Assignee: Ibis Biosciences, Inc., Carlsbad, CA (US)

( * ) Notice: Subject to any disclaimer, the term of this patent is extended or adjusted under 35 U.S.C. 154(b) by 144 days.

(21) Appl. No.: 11/059,776

(22) Filed: Feb. 17, 2005

(65) Prior Publication Data

US 2009/0004643 A1 Jan. 1, 2009

Related U.S. Application Data

(60) Provisional application No. 60/545,425, filed on Feb. 18, 2004, provisional application No. 60/559,754, filed on Apr. 5, 2004.

(51) Int. Cl.
*C12Q 1/68* (2006.01)
*C12P 19/34* (2006.01)

(52) U.S. Cl. ......................................... 435/6; 435/91.2

(58) Field of Classification Search ....................... None
See application file for complete search history.

(56) References Cited

U.S. PATENT DOCUMENTS

| | | | | |
|---|---|---|---|---|
| 4,075,475 | A | 2/1978 | Risby et al. | |
| 4,683,195 | A | 7/1987 | Mullis et al. | |
| 4,683,202 | A | 7/1987 | Mullis | |
| 4,965,188 | A | 10/1990 | Mullis et al. | |
| 5,015,845 | A | 5/1991 | Allen et al. | |
| 5,072,115 | A | 12/1991 | Zhou | |
| 5,213,961 | A | 5/1993 | Bunn et al. | |
| 5,219,727 | A | 6/1993 | Wang et al. | |
| 5,436,129 | A | 7/1995 | Stapleton | |
| 5,451,500 | A | 9/1995 | Stapleton | |
| 5,472,843 | A | 12/1995 | Milliman | |
| 5,476,774 | A | 12/1995 | Wang et al. | |
| 5,484,908 | A | 1/1996 | Froehler et al. | |
| 5,502,177 | A | 3/1996 | Matteucci et al. | |
| 5,503,980 | A | 4/1996 | Cantor | |
| 5,504,327 | A | 4/1996 | Sproch et al. | |
| 5,504,329 | A | 4/1996 | Mann et al. | |
| 5,523,217 | A | 6/1996 | Lupski et al. | |
| 5,527,669 | A | 6/1996 | Resnick et al. | |
| 5,527,675 | A | 6/1996 | Coull et al. | |
| 5,547,835 | A | 8/1996 | Koster | |
| 5,567,587 | A | 10/1996 | Kohne | |
| 5,576,204 | A | 11/1996 | Blanco et al. | |
| 5,580,733 | A | 12/1996 | Levis et al. | |
| 5,605,798 | A | 2/1997 | Koster | |
| 5,608,217 | A | 3/1997 | Franzen et al. | |
| 5,612,179 | A | 3/1997 | Simons | |
| 5,622,824 | A | 4/1997 | K oster | |
| 5,625,184 | A | 4/1997 | Vestal et al. | |
| 5,639,606 | A | 6/1997 | Willey | |
| 5,645,985 | A | 7/1997 | Froehler et al. | |
| 5,683,869 | A | 11/1997 | Shaw et al. | |
| 5,686,242 | A | 11/1997 | Bruice et al. | |
| 5,691,141 | A | 11/1997 | Koster | |
| 5,700,642 | A | 12/1997 | Monforte et al. | |
| 5,702,895 | A | 12/1997 | Matsunaga et al. | |
| 5,707,802 | A | 1/1998 | Sandhu et al. | |
| 5,712,125 | A | 1/1998 | Uhlen | |
| 5,716,825 | A | 2/1998 | Hancock et al. | |
| 5,727,202 | A | 3/1998 | Kucala | |
| 5,745,751 | A | 4/1998 | Nelson et al. | |
| 5,747,246 | A | 5/1998 | Pannetier et al. | |
| 5,747,251 | A | 5/1998 | Carson et al. | |
| 5,753,489 | A | 5/1998 | Kistner et al. | |
| 5,759,771 | A | 6/1998 | Tilanus | |
| 5,763,169 | A | 6/1998 | Sandhu et al. | |
| 5,763,588 | A | 6/1998 | Matteucci et al. | |
| 5,770,367 | A | 6/1998 | Southern et al. | |
| 5,777,324 | A | 7/1998 | Hillenkamp | |
| 5,814,442 | A * | 9/1998 | Natarajan et al. | 435/5 |
| 5,828,062 | A | 10/1998 | Jarrell et al. | |
| 5,830,653 | A | 11/1998 | Froehler et al. | |
| 5,830,655 | A | 11/1998 | Monforte et al. | |
| 5,832,489 | A | 11/1998 | Kucala | |
| 5,834,255 | A | 11/1998 | van Gemen et al. | |
| 5,845,174 | A | 12/1998 | Yasui et al. | |
| 5,849,492 | A | 12/1998 | Rogan | |
| 5,849,497 | A | 12/1998 | Steinman | |

(Continued)

FOREIGN PATENT DOCUMENTS

| | | |
|---|---|---|
| AU | 2003245488 | 6/2002 |

(Continued)

OTHER PUBLICATIONS

Ding et al (Proc. Natl. Acad. Sci. (Mar. 18, 2003 (online Mar. 6) 100(6):3059-3064).*

(Continued)

*Primary Examiner*—Kenneth R. Horlick
*Assistant Examiner*—David C Thomas
(74) *Attorney, Agent, or Firm*—Casimir Jones S.C.; Christopher C. Sappenfield

(57) ABSTRACT

The present invention provides methods for the quantification of an unknown bioagent in a sample by amplification of nucleic acid of the bioagent, and concurrent amplification of a known quantity of a calibration polynucleotide from which are obtained a bioagent identifying amplicon and a calibration amplicon. Upon molecular mass analysis, mass and abundance data are obtained. The identity of the bioagent is then determined from the molecular mass of the bioagent identifying amplicon and the quantity of the identified bioagent in the sample is determined from the abundance data of the bioagent identifying amplicon and the abundance data of the calibration amplicon.

30 Claims, 3 Drawing Sheets

U.S. PATENT DOCUMENTS

| | | | | |
|---|---|---|---|---|
| 5,849,901 | A | 12/1998 | Mabilat et al. | |
| 5,851,765 | A | 12/1998 | Koster | |
| 5,856,174 | A | 1/1999 | Lipshutz et al. | |
| 5,864,137 | A | 1/1999 | Becker et al. | |
| 5,866,429 | A | 2/1999 | Bloch | |
| 5,869,242 | A | 2/1999 | Kamb | |
| 5,871,697 | A | 2/1999 | Rothberg et al. | |
| 5,872,003 | A | 2/1999 | Koster | |
| 5,876,936 | A | 3/1999 | Ju | |
| 5,885,775 | A | 3/1999 | Haff et al. | |
| 5,928,905 | A | 7/1999 | Stemmer et al. | |
| 5,928,906 | A | 7/1999 | Koster et al. | |
| 5,965,363 | A | 10/1999 | Monforte et al. | |
| 5,976,798 | A | 11/1999 | Parker et al. | |
| 5,981,176 | A | 11/1999 | Wallace | |
| 5,981,190 | A | 11/1999 | Israel | |
| 5,994,066 | A | 11/1999 | Bergeron et al. | |
| 6,001,564 | A | 12/1999 | Bergeron et al. | |
| 6,005,096 | A | 12/1999 | Matteucci et al. | |
| 6,007,690 | A | 12/1999 | Nelson et al. | |
| 6,007,992 | A | 12/1999 | Lin et al. | |
| 6,015,666 | A | 1/2000 | Springer et al. | |
| 6,018,713 | A | 1/2000 | Coli et al. | |
| 6,028,183 | A | 2/2000 | Lin et al. | |
| 6,043,031 | A | 3/2000 | Koster et al. | |
| 6,046,005 | A | 4/2000 | Ju et al. | |
| 6,051,378 | A | 4/2000 | Monforte et al. | |
| 6,054,278 | A | 4/2000 | Dodge et al. | |
| 6,055,487 | A | 4/2000 | Margery et al. | |
| 6,061,686 | A | 5/2000 | Gauvin et al. | |
| 6,063,031 | A | 5/2000 | Cundari et al. | |
| 6,074,823 | A | 6/2000 | Koster | |
| 6,074,831 | A | 6/2000 | Yakhini et al. | |
| 6,090,558 | A | 7/2000 | Butler et al. | |
| 6,104,028 | A | 8/2000 | Hunter et al. | |
| 6,110,710 | A | 8/2000 | Smith et al. | |
| 6,111,251 | A | 8/2000 | Hillenkamp | |
| 6,140,053 | A | 10/2000 | Koster | |
| 6,146,144 | A | 11/2000 | Fowler et al. | |
| 6,146,854 | A | 11/2000 | Koster et al. | |
| 6,153,389 | A | 11/2000 | Haarer et al. | |
| 6,159,681 | A | 12/2000 | Zebala | |
| 6,180,339 | B1 | 1/2001 | Sandhu et al. | |
| 6,180,372 | B1 | 1/2001 | Franzen | |
| 6,194,144 | B1 | 2/2001 | Koster | |
| 6,197,498 | B1 | 3/2001 | Koster | |
| 6,214,555 | B1 | 4/2001 | Leushner et al. | |
| 6,218,118 | B1 | 4/2001 | Sampson et al. | |
| 6,221,587 | B1 | 4/2001 | Ecker et al. | |
| 6,221,601 | B1 | 4/2001 | Koster et al. | |
| 6,221,605 | B1 | 4/2001 | Koster | |
| 6,225,450 | B1 | 5/2001 | Koster | |
| 6,235,476 | B1 | 5/2001 | Bergmann et al. | |
| 6,235,478 | B1 | 5/2001 | Koster | |
| 6,235,480 | B1 | 5/2001 | Shultz et al. | |
| 6,238,871 | B1 | 5/2001 | Koster | |
| 6,238,927 | B1 | 5/2001 | Abrams et al. | |
| 6,239,159 | B1 | 5/2001 | Brown et al. | |
| 6,258,538 | B1 | 7/2001 | Koster et al. | |
| 6,261,769 | B1 | 7/2001 | Everett et al. | |
| 6,265,716 | B1 | 7/2001 | Hunter et al. | |
| 6,268,129 | B1 | 7/2001 | Gut et al. | |
| 6,268,131 | B1 | 7/2001 | Kang et al. | |
| 6,268,144 | B1 | 7/2001 | Koster | |
| 6,268,146 | B1 | 7/2001 | Shultz et al. | |
| 6,270,973 | B1 | 8/2001 | Lewis et al. | |
| 6,270,974 | B1 | 8/2001 | Shultz et al. | |
| 6,274,726 | B1 | 8/2001 | Laugharn, Jr. et al. | |
| 6,277,573 | B1 | 8/2001 | Koster | |
| 6,277,578 | B1 | 8/2001 | Shultz et al. | |
| 6,277,634 | B1 | 8/2001 | McCall et al. | |
| 6,300,076 | B1 | 10/2001 | Koster | |
| 6,303,297 | B1 | 10/2001 | Lincoln et al. | |
| 6,312,893 | B1 | 11/2001 | Van Ness et al. | |
| 6,312,902 | B1 | 11/2001 | Shultz et al. | |
| 6,322,970 | B1 | 11/2001 | Little et al. | |
| 6,361,940 | B1 | 3/2002 | Van Ness et al. | |
| 6,372,424 | B1 | 4/2002 | Brow et al. | |
| 6,389,428 | B1 | 5/2002 | Rigault et al. | |
| 6,391,551 | B1 | 5/2002 | Shultz et al. | |
| 6,393,367 | B1 | 5/2002 | Tang et al. | |
| 6,419,932 | B1 | 7/2002 | Dale | |
| 6,423,966 | B2 | 7/2002 | Hillenkamp et al. | |
| 6,428,955 | B1 | 8/2002 | Koster et al. | |
| 6,428,956 | B1 | 8/2002 | Crooke et al. | |
| 6,432,651 | B1 | 8/2002 | Hughes et al. | |
| 6,436,635 | B1 | 8/2002 | Fu et al. | |
| 6,436,640 | B1 | 8/2002 | Simmons et al. | |
| 6,453,244 | B1 | 9/2002 | Oefner | |
| 6,458,533 | B1 | 10/2002 | Felder et al. | |
| 6,468,743 | B1 | 10/2002 | Romick et al. | |
| 6,468,748 | B1 | 10/2002 | Monforte et al. | |
| 6,475,143 | B2 | 11/2002 | Iliff | |
| 6,475,736 | B1 | 11/2002 | Stanton, Jr. | |
| 6,479,239 | B1 | 11/2002 | Anderson et al. | |
| 6,500,621 | B2 | 12/2002 | Koster | |
| 6,553,317 | B1 | 4/2003 | Lincoln et al. | |
| 6,558,902 | B1 | 5/2003 | Hillenkamp | |
| 6,563,025 | B1 | 5/2003 | Song et al. | |
| 6,566,055 | B1 | 5/2003 | Monforte et al. | |
| 6,582,916 | B1 | 6/2003 | Schmidt et al. | |
| 6,586,584 | B2 | 7/2003 | McMillian et al. | |
| 6,589,485 | B2 | 7/2003 | Koster | |
| 6,602,662 | B1 | 8/2003 | Koster et al. | |
| 6,605,433 | B1 | 8/2003 | Fliss et al. | |
| 6,610,492 | B1 | 8/2003 | Stanton et al. | |
| 6,613,509 | B1 | 9/2003 | Chen | |
| 6,613,520 | B2 | 9/2003 | Ashby | |
| 6,623,928 | B2 | 9/2003 | Van Ness et al. | |
| 6,638,714 | B1 | 10/2003 | Linnen et al. | |
| 6,682,889 | B1 | 1/2004 | Wang et al. | |
| 6,705,530 | B2 | 3/2004 | Kiekhaefer | |
| 6,706,530 | B2 | 3/2004 | Hillenkamp | |
| 6,716,634 | B1 | 4/2004 | Myerson | |
| 6,783,939 | B2 | 8/2004 | Olmsted et al. | |
| 6,800,289 | B2 | 10/2004 | Nagata et al. | |
| 6,813,615 | B1 | 11/2004 | Colasanti et al. | |
| 6,836,742 | B2 | 12/2004 | Brekenfeld | |
| 6,852,487 | B1 | 2/2005 | Barany et al. | |
| 6,856,914 | B1 | 2/2005 | Pelech | |
| 6,875,593 | B2 | 4/2005 | Froehler et al. | |
| 6,906,316 | B2 | 6/2005 | Sugiyama et al. | |
| 6,906,319 | B2 | 6/2005 | Hoyes | |
| 6,914,137 | B2 | 7/2005 | Baker | |
| 6,977,148 | B2 | 12/2005 | Dean et al. | |
| 6,994,962 | B1 | 2/2006 | Thilly | |
| 7,022,835 | B1 | 4/2006 | Rauth et al. | |
| 7,024,370 | B2 | 4/2006 | Epler et al. | |
| 7,108,974 | B2 * | 9/2006 | Ecker et al. | 435/6 |
| 7,217,510 | B2 | 5/2007 | Ecker et al. | |
| 7,255,992 | B2 | 8/2007 | Ecker et al. | |
| 7,226,739 | B2 | 9/2007 | Ecker et al. | |
| 7,312,036 | B2 | 12/2007 | Sampath et al. | |
| 7,321,828 | B2 | 1/2008 | Cowsert et al. | |
| 7,349,808 | B1 | 3/2008 | Kreiswirth et al. | |
| 7,390,458 | B2 | 6/2008 | Burow et al. | |
| 2002/0006611 | A1 | 1/2002 | Portugal et al. | |
| 2002/0028923 | A1 | 3/2002 | Cowsert et al. | |
| 2002/0042112 | A1 | 4/2002 | Koster et al. | |
| 2002/0042506 | A1 | 4/2002 | Kristyanne et al. | |
| 2002/0045178 | A1 | 4/2002 | Cantor et al. | |
| 2002/0055101 | A1 | 5/2002 | Bergeron et al. | |
| 2002/0090320 | A1 | 7/2002 | Burow et al. | |
| 2002/0120408 | A1 | 8/2002 | Kreiswirth et al. | |

| | | | |
|---|---|---|---|
| 2002/0137057 | A1 | 9/2002 | Wold et al. |
| 2002/0138210 | A1 | 9/2002 | Wilkes et al. |
| 2002/0150903 | A1 | 10/2002 | Koster |
| 2002/0150927 | A1 | 10/2002 | Matray et al. |
| 2002/0168630 | A1 | 11/2002 | Fleming et al. |
| 2003/0017487 | A1 | 1/2003 | Xue et al. |
| 2003/0027135 | A1 | 2/2003 | Ecker et al. |
| 2003/0039976 | A1 | 2/2003 | Haff |
| 2003/0050470 | A1 | 3/2003 | An et al. |
| 2003/0064483 | A1 | 4/2003 | Shaw et al. |
| 2003/0073112 | A1 | 4/2003 | Zhang et al. |
| 2003/0082539 | A1 | 5/2003 | Ecker et al. |
| 2003/0101172 | A1 | 5/2003 | Ecker et al. |
| 2003/0104410 | A1 | 6/2003 | Mittmann |
| 2003/0113745 | A1 | 6/2003 | Monforte et al. |
| 2003/0119018 | A1 | 6/2003 | Omura et al. |
| 2003/0124556 | A1 | 7/2003 | Ecker et al. |
| 2003/0129589 | A1 | 7/2003 | Koster et al. |
| 2003/0134312 | A1 | 7/2003 | Burgoyne |
| 2003/0143201 | A1 | 7/2003 | Nagata et al. |
| 2003/0148284 | A1 | 8/2003 | Vision et al. |
| 2003/0167133 | A1 | 9/2003 | Ecker et al. |
| 2003/0167134 | A1 | 9/2003 | Ecker et al. |
| 2003/0175695 | A1 | 9/2003 | Ecker et al. |
| 2003/0175696 | A1 | 9/2003 | Ecker et al. |
| 2003/0175697 | A1 | 9/2003 | Ecker et al. |
| 2003/0175729 | A1 | 9/2003 | Van Eijk et al. |
| 2003/0186247 | A1 | 10/2003 | Smarason et al. |
| 2003/0187588 | A1 | 10/2003 | Ecker et al. |
| 2003/0187593 | A1 | 10/2003 | Ecker et al. |
| 2003/0187615 | A1 | 10/2003 | Epler et al. |
| 2003/0190605 | A1 | 10/2003 | Ecker et al. |
| 2003/0190635 | A1 | 10/2003 | McSwiggen |
| 2003/0194699 | A1 | 10/2003 | Lewis et al. |
| 2003/0203398 | A1 | 10/2003 | Bramucci et al. |
| 2003/0220844 | A1 | 11/2003 | Marnellos et al. |
| 2003/0224377 | A1 | 12/2003 | Wengel et al. |
| 2003/0225529 | A1 | 12/2003 | Ecker et al. |
| 2003/0228571 | A1 | 12/2003 | Ecker et al. |
| 2003/0228613 | A1 | 12/2003 | Bornarth et al. |
| 2004/0005555 | A1 | 1/2004 | Rothman et al. |
| 2004/0014957 | A1 | 1/2004 | Eldrup et al. |
| 2004/0023207 | A1 | 2/2004 | Polansky |
| 2004/0023209 | A1 | 2/2004 | Jonasson |
| 2004/0029129 | A1 | 2/2004 | Wang et al. |
| 2004/0038206 | A1 | 2/2004 | Zhang et al. |
| 2004/0038234 | A1 | 2/2004 | Gut et al. |
| 2004/0038385 | A1 | 2/2004 | Langlois et al. |
| 2004/0101809 | A1 | 5/2004 | Weiss et al. |
| 2004/0110169 | A1 | 6/2004 | Ecker et al. |
| 2004/0111221 | A1 | 6/2004 | Beattie et al. |
| 2004/0117129 | A1 | 6/2004 | Ecker et al. |
| 2004/0121309 | A1 | 6/2004 | Ecker et al. |
| 2004/0121310 | A1 | 6/2004 | Ecker et al. |
| 2004/0121311 | A1 | 6/2004 | Ecker et al. |
| 2004/0121312 | A1 | 6/2004 | Ecker et al. |
| 2004/0121313 | A1 | 6/2004 | Ecker et al. |
| 2004/0121314 | A1 | 6/2004 | Ecker et al. |
| 2004/0121315 | A1 | 6/2004 | Ecker et al. |
| 2004/0121329 | A1 | 6/2004 | Ecker et al. |
| 2004/0121335 | A1 | 6/2004 | Ecker et al. |
| 2004/0121340 | A1 | 6/2004 | Ecker et al. |
| 2004/0122598 | A1 | 6/2004 | Ecker et al. |
| 2004/0122857 | A1 | 6/2004 | Ecker et al. |
| 2004/0126764 | A1 | 7/2004 | Lasken et al. |
| 2004/0137013 | A1 | 7/2004 | Katinger et al. |
| 2004/0161770 | A1 | 8/2004 | Ecker et al. |
| 2004/0180328 | A1 | 9/2004 | Ecker et al. |
| 2004/0185438 | A1 | 9/2004 | Ecker |
| 2004/0191769 | A1 | 9/2004 | Marino et al. |
| 2004/0202997 | A1 | 10/2004 | Ecker et al. |
| 2004/0209260 | A1 | 10/2004 | Ecker et al. |
| 2004/0219517 | A1 | 11/2004 | Ecker et al. |
| 2005/0026147 | A1 | 2/2005 | Walker et al. |
| 2005/0026641 | A1 | 2/2005 | Hokao |
| 2005/0027459 | A1 | 2/2005 | Ecker et al. |
| 2005/0065813 | A1 | 3/2005 | Mishelevich et al. |
| 2005/0130196 | A1 | 6/2005 | Hofstadler et al. |
| 2005/0130216 | A1 | 6/2005 | Becker et al. |
| 2005/0142584 | A1 | 6/2005 | Willson et al. |
| 2005/0250125 | A1 | 11/2005 | Novakoff |
| 2005/0266397 | A1 | 12/2005 | Ecker et al. |
| 2006/0020391 | A1 | 1/2006 | Kreiswirth et al. |
| 2006/0121520 | A1 | 6/2006 | Ecker et al. |
| 2006/0172330 | A1 | 8/2006 | Osborn et al. |
| 2006/0205040 | A1 | 9/2006 | Sampath |
| 2006/0240412 | A1 | 10/2006 | Hall et al. |
| 2006/0259249 | A1 | 11/2006 | Sampath et al. |
| 2006/0275788 | A1 | 12/2006 | Ecker et al. |
| 2007/0048735 | A1 | 3/2007 | Ecker et al. |
| 2007/0218467 | A1 | 9/2007 | Ecker et al. |
| 2008/0160512 | A1 | 7/2008 | Ecker et al. |
| 2009/0004643 | A1 | 1/2009 | Ecker et al. |

FOREIGN PATENT DOCUMENTS

| | | |
|---|---|---|
| CN | 1202204 | 12/1998 |
| DE | 19732086 | 1/1999 |
| DE | 19802905 | 7/1999 |
| DE | 19824280 | 12/1999 |
| DE | 19852167 | 5/2000 |
| DE | 19943374 | 3/2001 |
| DE | 10132147 | 2/2003 |
| EP | 0281390 | 9/1988 |
| EP | 0633321 | 11/1995 |
| EP | 0620862 | 4/1998 |
| EP | 1035219 | 9/2000 |
| EP | 1138782 | 2/2003 |
| EP | 1308506 | 5/2003 |
| EP | 1310571 | 5/2003 |
| EP | 1333101 | 8/2003 |
| EP | 1365031 | 11/2003 |
| EP | 1234888 | 1/2004 |
| EP | 1748072 | 1/2007 |
| FR | 2811321 | 1/2002 |
| GB | 2325002 | 11/1998 |
| GB | 2339905 | 2/2000 |
| JP | 5-276999 | 10/1993 |
| JP | 2004-200 | 1/2004 |
| JP | 2004-24206 | 1/2004 |
| JP | 2004-201641 | 7/2004 |
| JP | 2004-201679 | 7/2004 |
| WO | WO 88/003957 | 6/1988 |
| WO | WO 90/015157 | 12/1990 |
| WO | WO 92/008117 | 5/1992 |
| WO | WO 92/05182 | 11/1992 |
| WO | WO 92/19774 | 11/1992 |
| WO | WO 93/003186 | 2/1993 |
| WO | WO 93/008297 | 4/1993 |
| WO | WO 94/016101 | 7/1994 |
| WO | WO 94/019490 | 9/1994 |
| WO | WO 94/021822 | 9/1994 |
| WO | WO 95/004161 | 2/1995 |
| WO | WO 95/011996 | 5/1995 |
| WO | WO 95/013395 | 5/1995 |
| WO | WO 95/013396 | 5/1995 |
| WO | WO95/031997 | 11/1995 |
| WO | WO 96/016186 | 5/1996 |
| WO | WO 96/029431 | 9/1996 |
| WO | WO 96/032504 | 10/1996 |
| WO | WO 96/037630 | 11/1996 |
| WO | WO 97/033000 | 9/1997 |
| WO | WO 97/034909 | 9/1997 |
| WO | WO 97/037041 | 10/1997 |
| WO | WO 97/47766 | 12/1997 |
| WO | WO 98/003684 | 1/1998 |

| | | | |
|---|---|---|---|
| WO | WO 98/012355 | | 3/1998 |
| WO | WO 98/014616 | | 4/1998 |
| WO | WO 98/015652 | | 4/1998 |
| WO | WO 98/020020 | | 5/1998 |
| WO | WO 98/020157 | | 5/1998 |
| WO | WO 98/020166 | | 5/1998 |
| WO | WO 98/026095 | | 6/1998 |
| WO | WO 98/031830 | | 7/1998 |
| WO | WO 98/035057 | | 8/1998 |
| WO | WO 98/040520 | | 9/1998 |
| WO | WO 98/054751 | | 12/1998 |
| WO | WO 99/005319 | | 2/1999 |
| WO | WO 99/012040 | | 3/1999 |
| WO | WO 99/013104 | | 3/1999 |
| WO | WO 99/014375 | | 3/1999 |
| WO | WO 99/029898 | | 6/1999 |
| WO | WO 99/031278 | | 6/1999 |
| WO | WO 00/063362 | | 10/1999 |
| WO | WO 99/057318 | | 11/1999 |
| WO | WO 99/058713 | | 11/1999 |
| WO | WO 99/60183 | | 11/1999 |
| WO | WO 00/066789 | | 11/2000 |
| WO | WO 01/007648 | | 2/2001 |
| WO | WO 01/012853 | | 2/2001 |
| WO | WO 01/023604 | | 4/2001 |
| WO | WO 01/023608 | | 4/2001 |
| WO | WO 01/032930 | | 5/2001 |
| WO | WO 01/040497 | | 6/2001 |
| WO | WO 01/046404 | | 6/2001 |
| WO | WO 01/051661 | | 7/2001 |
| WO | WO 01/051662 | | 7/2001 |
| WO | WO 01/057263 | | 8/2001 |
| WO | WO 01/057518 | | 8/2001 |
| WO | WO 01/073119 | | 10/2001 |
| WO | WO 01/073199 | | 10/2001 |
| WO | WO 01/077392 | | 10/2001 |
| WO | WO 02/002811 | | 1/2002 |
| WO | WO 02/010186 | | 2/2002 |
| WO | WO 02/010444 | | 2/2002 |
| WO | WO 02/018641 | | 3/2002 |
| WO | WO 02/021108 | | 3/2002 |
| WO | WO 02/022873 | | 3/2002 |
| WO | WO 02/024876 | | 3/2002 |
| WO | WO 02/050307 | | 6/2002 |
| WO | WO 02/057491 | | 7/2002 |
| WO | WO 02/070664 | | 9/2002 |
| WO | WO02/070664 | * | 9/2002 |
| WO | WO 02/070728 | | 9/2002 |
| WO | WO 02/077278 | | 10/2002 |
| WO | WO 02/099034 | | 12/2002 |
| WO | WO 02/099095 | | 12/2002 |
| WO | WO 02/099129 | | 12/2002 |
| WO | WO 02/099130 | | 12/2002 |
| WO | WO 2003/002750 | | 1/2003 |
| WO | WO 2003/008636 | | 1/2003 |
| WO | WO 03/012058 | | 2/2003 |
| WO | WO 03/012074 | | 2/2003 |
| WO | WO 03/014382 | | 2/2003 |
| WO | WO 2003/016546 | | 2/2003 |
| WO | WO 03/020890 | | 3/2003 |
| WO | WO 03/033732 | | 4/2003 |
| WO | WO 03/054162 | | 7/2003 |
| WO | WO 03/054755 | | 7/2003 |
| WO | WO 2003/060163 | | 7/2003 |
| WO | WO 2003/075955 | | 9/2003 |
| WO | WO 2003/088979 | | 10/2003 |
| WO | WO 2003/093506 | | 11/2003 |
| WO | WO 2003/097869 | | 11/2003 |
| WO | WO 2003/100035 | | 12/2003 |
| WO | WO 2003/100068 | | 12/2003 |
| WO | WO 2003/104410 | | 12/2003 |
| WO | WO 2004/003511 | | 1/2004 |
| WO | WO 2004/011651 | | 2/2004 |
| WO | WO 2004/040013 | | 5/2004 |
| WO | WO 2004/044123 | | 5/2004 |
| WO | WO 2004/044247 | | 5/2004 |
| WO | WO 2004/052175 | | 6/2004 |
| WO | WO 2004/053076 | | 6/2004 |
| WO | WO 2004/053141 | | 6/2004 |
| WO | WO 2004/053164 | | 6/2004 |
| WO | WO 2004/060278 | | 7/2004 |
| WO | WO 2004/070001 | | 8/2004 |
| WO | WO 2004/072230 | | 8/2004 |
| WO | WO 2004/072231 | | 8/2004 |
| WO | WO 2004/101809 | | 11/2004 |
| WO | WO 2005/003384 | | 1/2005 |
| WO | WO 2005/012572 | | 2/2005 |
| WO | WO 2005/024046 | | 3/2005 |
| WO | WO 2005/053141 | | 6/2005 |
| WO | WO 2005/054454 | | 6/2005 |
| WO | WO 2005/075686 | | 10/2005 |
| WO | WO 2005/091971 | | 10/2005 |
| WO | WO 2005/098047 | | 10/2005 |
| WO | WO 2006/089762 | | 8/2006 |
| WO | WO 2006/094238 | | 9/2006 |
| WO | WO 2006/116127 | | 11/2006 |
| WO | WO 2008/118809 | | 10/2008 |

OTHER PUBLICATIONS

Flora et al (Anal. Bioanal. Chem. (2002) 373 :538-546).*

Arnal et al (Applied and Environmental Microbiology (1999) 65(1):322-326).*

Amexis, G. et al., "Quantitative mutant analysis of viral quasispecies by chip-based matrix-assisted laser desorption/ionization of time-of-flight mass spectrometry," *Proc. Natl. Acad. Sci.* USA (2001) 98(21):12097-12102. Correction: 98(24): 14186.

Boivin-Jahns, V. et al., "Bacterial Diversity in a Deep-Subsurface Clay Environment," *Appl. Environ. Microbiol.* (1996) 62(9): 3405-3412.

Chelly, J. et al., "Transcription of the dystrophin gene in human muscle and non-muscle tissue," *Nature* (1988) 333(6176): 858-860.

Denis, M. et al., "Development of a semiquantitative PCR assay using internal standard and colorimetric detection on microwell plate for pseudorabies virus," *Mol. Cell. Probes* (1997) 11(6): 439-448.

Eremeeva, M. E. et al., "Evaluation of a PCR Assay for Quantitation of *Rickettsia rickettsii* and Closely Related Spotted Fever Group Rickettsiae," *J. Clin. Microbiol.* (2003) 41(12): 5466-5472.

Garcia, S. et al., "Quantitative Real-Time PCR Detection of Rift Valley Fever Virus and Its Application to Evaluation of Antiviral Compounds," *J. Clin. Microbiol.* (2001) 39(12): 4456-61.

Gilbert, N. et al., "Comparison of commercial assays for the quantitation of HBV DNA load in health care workers: calibration differences," *J. Virol. Methods* (2002) 100(1-2): 37-47.

Gilliland, G. et al., "Analysis of cytokine mRNA and DNA: detection and quantitation by competitive polymerase chain reaction," *Proc. Natl. Acad. Sci.* USA (1990) 87(7): 2725-2729.

Guatelli, J. C. et al., "Nucleic Acid Amplification In Vitro: Detection of Sequences with Low Copy Numbers and Application to Diagnosis of Human Immunodeficiency Virus Type 1 Infection," *Clin. Microbiol. Rev.* (1989) 2(2): 217-226.

Hāmmerle, T. et al., "A sensitive PCR assay system for the quantitation of viral genome equivalents: hepatitis C virus (HCV)," *Arch. Virol.* (1996) 141: 2103-2114.

Le Cann, P. et al., "Quantification of human astroviruses in sewage using real-time RT-PCR," *Res. Microbiol.* (2004) 155(1): 11-15.

Mellor, J. et al., "Genotype Dependence of Hepatitis C Virus Load Measurement in Commercially Available Quantitative Assays," *J. Clin. Microbiol.* (1999) 37(8): 2525-2532.

Muddiman, D. C. et al., "Characterization of PCR Products from Bacilli Using Electrospray Ionization FTICR Mass Spectrometry," *Anal. Chem.* (1996) 68(21): 3705-3712.

Muddiman, D. C. et al., "Length and Base Composition of PCR-Amplified Nuelcic Acids Using Mass Measurements from Electrospray Ionization Mass Spectrometry," *Anal. Chem.* (1997) 69(8): 1543-1549.

Nygren, M. et al., "Quantification of HIV-1 Using Multiple Quantitative Polymerase Chain Reaction Standards and Bioluminometric Detection," *Anal. Biochem.* (2001) 288(1): 28-38.
Peters, S. E. et al., "Quantification of the detection of *Pneumocystis carinii* by DNA amplification," *Mol. Cell. Probes* (1992) 6: 115-117.
Rupf, S. et al., "Quantitative determination of *Streptococcus mutans* by using competitive polymerase chain reaction," *Eur. J. Oral. Sci.* (1999) 107(2): 75-81.
Widjojoatmodjo, M. N. et al., "Rapid Identification of Bacteria by PCR-Single Strand Conformation Polymorphism," *J. Clin. Microbiol.* (1994) 32(12): 3002-3007.
U.S. Appl. No. 90/010,209, filed Jun. 27, 2008, Ecker et al.
U.S. Appl. No. 90/010,210, filed Jun. 27, 2008, Ecker et al.
Aaserud et al., "Accurate base composition of double-strand DNA by mass spectrometry" *J. Am. Soc. Spec.* (1996) 7:1266-1269.
Alves-Silva, J. et al., "The Ancestry of Brazilian mtDNA Lineages," *Am. J. Hum. Genet.* (2000) 67:444- 461.
Anderson et al., "Sequence and organization of the human mitochondrial genome," *Nature* (1981) 290:457-465.
Andreasson et al., "Mitochondrial Sequence Analysis for Forensic Identification Using Pyrosequencmg Technology" *BioTechniques* (2002) 32:124-133.
U.S. Appl. No. 09/798,007 Office Communication Mailed Apr. 16, 2002.
U.S. Appl. No. 09/798,007 Office Communication Mailed Jun. 20, 2002.
U.S. Appl. No. 09/798,007 Office Communication Mailed Nov. 6, 2002.
U.S. Appl. No. 09/798,007 Office Communication Mailed Jan. 8, 2003.
U.S. Appl. No. 09/798,007 Office Communication Mailed Jan. 31, 2003.
U.S. Appl. No. 09/798,007 Office Communication Mailed Feb. 27, 2003.
U.S. Appl. No. 09/798,007 Office Communication Mailed May 20, 2003.
U.S. Appl. No. 09/798,007 Office Communication Mailed Jul. 11, 2003.
U.S. Appl. No. 09/798,007 Office Communication Mailed Sep. 22, 2003.
U.S. Appl. No. 09/798,007 Office Communication Mailed Nov. 19, 2003.
U.S. Appl. No. 09/798,007 Office Communication Mailed Jun. 30, 2004.
U.S. Appl. No. 09/798,007 Office Communication Mailed Aug. 10, 2004.
U.S. Appl. No. 09/798,007 Office Communication Mailed Feb. 10, 2005.
U.S. Appl. No. 10/156,608 Office Communication Mailed Apr. 1, 2004.
U.S. Appl. No.10/156,608 Office Communication Mailed Aug. 10, 2004.
U.S. Appl. No. 10/156,608 Office Communication Mailed Oct. 14, 2004.
U.S. Appl. No. 10/156,608 Office Communication Mailed Nov. 19, 2004.
U.S. Appl. No. 10/156,608 Office Communication Mailed Dec. 9, 2004.
U.S. Appl. No.10/156,608 Office Communication Mailed May 10, 2005.
U.S. Appl. No. 10/156,608 Office Communication Mailed May 26, 2005.
U.S. Appl. No. 10/156,608 Office Communication Mailed Jun. 2, 2005 with associated Information Disclosure Statement filed Nov. 28, 2005.
U.S. Appl. No.10/156,608 Office Communication Mailed Jul. 20, 2005.
U.S. Appl. No. 10/156,608 Office Communication Mailed Sep. 15, 2005.
U.S. Appl. No. 10/660,997 Office Communication Mailed Mar. 13, 2006.
U.S. Appl. No. 10/660,997 Office Communication Mailed May 26, 2006.
U.S. Appl. No. 10/660,997 Office Communication Mailed Sep. 18, 2006.
U.S. Appl. No. 10/660,997 Office Communication Mailed Nov. 21, 2006.
U.S. Appl. No. 10/660,997 Office Communication Mailed Apr. 26, 2007 with associated Information Disclosure Statement filed Feb. 20, 2007.
U.S. Appl. No. 10/660,122 Office Communication Mailed Mar. 17, 2006.
U.S. Appl. No. 10/660,122 Office Communication Mailed Jul. 6, 2006.
U.S. Appl. No. 10/660,122 Office Communication Mailed Sep. 19, 2006.
U.S. Appl. No. 10/660,122 Office Communication Mailed Apr. 20, 2007.
U.S. Appl. No. 10/660,122 Office Communication Mailed Sep. 19, 2007.
U.S. Appl. No. 10/660,122 Office Communication Mailed Mar. 21, 2008.
U.S. Appl. No. 10/660,122 Office Communication Mailed Jul. 9, 2008.
U.S. Appl. No. 10/660,122 Office Communication Mailed Sep. 17, 2008.
U.S. Appl. No. 10/660,996 Office Communication Mailed Feb. 28, 2006.
U.S. Appl. No. 10/660,996 Office Communication Mailed May 30, 2006.
U.S. Appl. No.10/660,996 Office Communication Mailed Jul. 12, 2006.
U.S. Appl. No. 10/660,996 Office Communication Mailed Sep. 5, 2006.
U.S. Appl. No. 10/660,996 Office Communication Mailed Nov. 22, 2006.
U.S. Appl. No. 10/660,996 Office Communication Mailed Jul. 10, 2007 with associated Information Disclosure Statement filed Feb. 21, 2007.
U.S. Appl. No. 10/660,998 Office Communication Mailed May 1, 2006.
U.S. Appl. No. 10/660,998 Office Communication Mailed Aug. 3, 2006.
U.S. Appl. No. 10/660,998 Office Communication Mailed Jan. 24, 2007.
U.S. Appl. No. 10/660,998 Office Communication Mailed Aug. 7, 2007
U.S. Appl. No. 10/660,998 Office Communication Mailed Dec. 11, 2007
U.S. Appl. No. 10/660,998 Office Communication Mailed Sep. 19, 2008.
U.S. Appl. No. 11/233,630 Office Communication Mailed Jun. 8, 2007.
U.S. Appl. No. 11/233,630 Office Communication Mailed Jul. 13, 2007.
U.S. Appl. No. 11/233,630 Office Communication Mailed Apr. 16, 2008.
U.S. Appl. No. 11/233,630 Office Communication Mailed Oct. 2, 2008.
U.S. Appl. No.11/331,978 Office Communication Mailed Nov. 15, 2007.
U.S. Appl. No. 11/331,978 Office Communication Mailed Aug. 15, 2008.
U.S. Appl. No. 11/331,978 Office Communication Mailed Oct. 17, 2008.
U.S. Appl. No. 11/331,987 Office Communication Mailed Jul. 16, 2007.
U.S. Appl. No. 11/331,987 Office Communication Mailed Oct. 22, 2007.
U.S. Appl. No. 11/331,987 Office Communication Mailed Jul. 9, 2008.
U.S. Appl. No. 09/891,793 Office Communication Mailed Dec. 18, 2002.
U.S. Appl. No. 09/891,793 Office Communication Mailed Aug. 26, 2003.

U.S. Appl. No. 09/891,793 Office Communication Mailed Nov. 13, 2003.
U.S. Appl. No. 09/891,793 Office Communication Mailed Mar. 9, 2004.
U.S. Appl. No. 09/891,793 Office Communication Mailed Jun. 14, 2004.
U.S. Appl. No. 09/891,793 Office Communication Mailed Jul. 13, 2004.
U.S. Appl. No. 09/891,793 Office Communication Mailed Aug. 10, 2004.
U.S. Appl. No. 09/891,793 Office Communication Mailed Oct. 20, 2004.
U.S. Appl. No. 09/891,793 Office Communication Mailed Mar. 8, 2005.
U.S. Appl. No. 09/891,793 Office Communication Mailed May 19, 2005.
U.S. Appl. No. 09/891,793 Office Communication Mailed Aug. 11, 2005.
U.S. Appl. No. 09/891,793 Office Communication Mailed Mar. 16, 2006.
U.S. Appl. No. 09/891,793 Office Communication Mailed Jul. 12, 2006.
U.S. Appl. No. 09/891,793 Office Communication Mailed Sep. 13, 2006.
U.S. Appl. No. 09/891,793 Office Communication Mailed Nov. 20, 2006.
U.S. Appl. No. 10/754,415 Office Communication Mailed Mar. 13, 2006.
U.S. Appl. No. 10/754,415 Office Communication Mailed Aug. 28, 2006.
U.S. Appl. No. 10/754,415 Office Communication Mailed Nov. 17, 2006.
U.S. Appl. No. 10/754,415 Office Communication Mailed Feb. 27, 2007.
U.S. Appl. No. 10/754,415 Office Communication Mailed Aug. 30, 2007.
U.S. Appl. No.10/754,415 Office Communication Mailed Oct. 10, 2007.
U.S. Appl. No. 10/754,415 Office Communication Mailed Jun. 12, 2008.
U.S. Appl. No. 10/728,486 Office Communication Mailed Apr. 10, 2006.
U.S. Appl. No. 10/728,486 Office Communication Mailed Jul. 27, 2006.
U.S. Appl. No. 10/728,486 Office Communication Mailed Oct. 17, 2006.
U.S. Appl. No. 10/728,486 Office Communication Mailed Dec. 20, 2006.
U.S. Appl. No. 10/728,486 Office Communication Mailed May 11, 2007.
U.S. Appl. No. 10/728,486 Office Communication Mailed Jan. 17, 2008.
U.S. Appl. No. 10/728,486 Office Communication Mailed Nov. 3, 2008.
U.S. Appl. No. 10/418,514 Office Communication Mailed Sep. 29, 2005.
U.S. Appl. No. 10/418,514 Office Communication Mailed Feb. 27, 2006.
U.S. Appl. No. 10/418,514 Office Communication Mailed Mar. 27, 2007.
U.S. Appl. No. 10/418,514 Office Communication Mailed Dec. 6, 2007.
U.S. Appl. No. 10/418,514 Office Communication Mailed Apr. 15, 2008.
U.S. Appl. No. 10/418,514 Office Communication Mailed Jul. 1, 2008.
U.S. Appl. No. 11/059,776 Office Communication Mailed Jan. 19, 2007.
U.S. Appl. No. 11/059,776 Office Communication Mailed May 29, 2007.
U.S. Appl. No. 11/059,776 Office Communication Mailed Jan. 23, 2008.
U.S. Appl. No. 11/060,135 Office Communication Mailed Dec. 21, 2006.
U.S. Appl. No. 11/060,135 Office Communication Mailed Mar. 8, 2007.
U.S. Appl. No. 11/060,135 Office Communication Mailed Jul. 24, 2007.
U.S. Appl. No. 11/491,376 Office Communication Mailed Oct. 31, 2008.
U.S. Appl. No. 11/210,516 Office Communication Mailed Jun. 8, 2007.
U.S. Appl. No. 11/210,516 Office Communication Mailed Oct. 19, 2007.
U.S. Appl. No. 11/409,535 Office Communication Mailed Oct. 31, 2007.
U.S. Appl. No. 90/010,209 Office Communication Mailed Jun. 27, 2008.
U.S. Appl. No. 90/010,209 Office Communication Mailed Jul. 22, 2008.
U.S. Appl. No. 90/010,210 Office Communication Mailed Jun. 27, 2008.
U.S. Appl. No. 90/010,210 Office Communication Mailed Jul. 22, 2008.
Bahrmand et al., "Polymerase chain reaction of bacterial genomes with single universal primer: application to distinguishing mycobacteria species" *Molecular and Cellular Probes* (1996) 10:117-122.
Bahrmand et al., "Use of restriction enzyme analysis of amplified DNA coding for the hsp65 gene and polymerase chain reaction with universal primer for rapid differentiation of mycobacterium species in the clinical laboratory" *Scandinavian Journal of Infectious Diseases* (1998) 30:477-480.
Baker et al., "Review and re-analysis of domain-specific 16S primers" *J. Microbiol. Methods* (2003) 55:541-555.
Bastia et al., "Organelle DNA analysis of Solanum and Brassica somatic hybrids by PCR with 'universal primers'." *Theoretical and Applied Genetics* (2001) 102:1265-1272.
Batey et al., "Preparation of Isotopically Labeled Ribonucleotides for Multidimensional NMR Spectroscopy of Rna" *Nucleic Acids Research* (1992) 20:4515-4523.
Baumer et al., "Age-related Human mtDNA Deletions: a Heterogeneous Set of Deletions Arising at a Single Pair of Directly Repeated Sequences" *Am. J. Hum. Genet*. (1994) 54:618-630.
Benson et al., "Advantages of Thermococcus kodakaraenis (KOD) DNA polymerase for PCR-mass spectrometry based analyses" *J. Am. Soc. Mass Spectrom*. (2003) 14:601-604.
Black et al., "Detection of trace levels of tricothecene mycotoxins in human urine by gas chromatography-mass spectrometry" J. *Chromatog* (1986) 367:103-115.
Blast Search results (Mar. 2006).
Boivin-Jahns etal., "Bacterial Diversity in a Deep-Subsurface Clay Environment" *Applied and Environmental Microbiology* (1996) 62:3405-3412.
Borrow et al., "SiaD PCR Elisa for confirmation and identification of serogroup Y and W135 meningococcal infections" *FEMS Microbiological Letters* (1998) 159:209-214.
Bowen et al., "The native virulence plasmid combination affects the segegational stability of a theta-replicating shuttle vector in bacillus anthracis var, New Hampshire" *J. Appl. Microbiol*. (1999) 87:270-278.
Campbell et al., "Detection of California serogroup Bunyaviruses in tissue culture and mosquito pools by PCR" *J. Virol. Methods* (1996) 57:175-179.
Carracedo et al., "Dna commission of the international society for forensic genetics: guidelines for mitochondrial Dna typing" *Forensic Science International* (2000) 110:79-85.
Case et al., "Maternal inheritance of mitochondrial DNA polymorphisms in cultured human fibroblasts," *Somatic Cell Genetics* (1981) 7:103-108.
Cespedes et al., "Polymerase chain reaction restriction fragment length polymorphism analysis of a short fragment of the cytoclu-ome b gene for identification of flatfish species" *J. Food Protection* (1998) 61:1684- 1685.

Chang, P.-K. et al., "aflT, a MFS transporter-encoding gene located in the aflatoxin gene cluster, does not have a significant role in aflatoxin secretion," Fungal Genet.Biol. (2004) 41:911-920.
Chen et al., "Universal primers for amplification of mitochondrial small subunit ribosomal RNA-encoding gene in scleractinian corals" *Marine Biotechnology* (2000) 2:146-153.
Chen et al., "A universal PCR primer to detect members of the Potyviridae and its use to examine the taxonomic status of several members of the family" *Archives of Virology* (2001) 146:757-766.
Chen, N. etal., "The genomic sequence of ectromelia virus, the causative agent of mousepox," Virology (2003) 317:165-186.
Cho etal., "Application of the ribonuclease P (RNase P) Rna gene sequence for phylogenetic analysis of the gene Saccharomonospora" International Journal of Systematic Bacteriology (1998) 48:1223-1230.
Conrads etal., "16S-23S rDNA internal transcribed spacer sequences for analysis of the phylogenetic relationships among species of the genus Fusobacterium" International Journal of Systematic and Evolutionary Microbiology (2002) 52:493-499.
Cornel et al., "Polymerase chain reaction species diagnostic assay for Anopheles quadrimaculatus cryptic species (Diptera: Culicidae) based on ribosomal Dna ITS2 sequences" Journal of Medical Entomology (1996) 33:109-116.
Crain etal., "Applications of mass spectrometry of the characterization of oligonucleotides and nucleic acids" Cum Opin. Biotechnol. (1998) 9:25-34.
Crespillo etal., "Mitochondrial DNA sequences for 118 individuals from northeastern Spain" Int. J. Legal Med. (2000) 114:130-132.
Dasen etal., "Classification and identification of Propionibacteria based on 16S ribosomal RNA genes and PCR" Systematic and Applied Microbiology (1998) 21:251-259.
Deforce etal., "Analysis of oligonucleotides by Esi-Ms" Advances in Chromatography (2000) 40:539- 566.
Deforce etal., "Characterization of Dna Oligonucleotides by Coupling of Capillary Zone Electrophoresis to Electrospray Ionization Q-Tof Mass Spectrometry" Analytical Chemistry (1998) 70:3060-3068.
Demesure etal., "A set of universal primers for amplification of polymorphic non-coding regions of mitochondrial and chloroplast Dna in plants" Molecular Ecology (1995) 4:129-131.
Dias Neto et al., "Shotgun sequencing of the human transcriptome with Orf expressed sequence tags" PNAS (2000) 97:3491-3496.
Dinauer etal., "Sequence-based typing of HLA class II DQB1" Tissue Anigens (2000) 55:364-368.
Dubernet etal., "A PCR-based method for identification of Lactobacilli at the genus level" Fems Microbiology Letters (2002) 214:271-275.
Elnifro etal., "Pcr and Restriction Endonuclease Analysis for Rapid Identification of Adenovirus Subgenera Journal of Clinical Microbiology (2000) 38:2055-2061.
Embl Accession No. S90302, Human, Muscle, Mitochondrial Mutant, 22 nt, segment 2 of 2 (XP002436791) Nov. 26, 1993.
Esmans et al., "Liquid Chromatography-Mass Spectrometry in Nucleoside, nucleotide and modified nucleotide characterization" J. Of Chromatography a (1998) 794:109-127.
European Search Report for 02709785.6 dated Oct. 10, 2005.
European Patent Office Communication 96(2) Epc for 02709785.6 dated Nov. 20, 2006.
European Supplemental Search Report for 03796752.8 dated Aug. 14, 2007.
European Supplemental Search Report for 03810055.8 dated Jul. 9, 2007
Figueiredo et al., "Identification of Brazilian flaviviruses by a simplified reverse transcription-polymerase chain reaction method using Flavivirus universal primers" American Journal of Tropical Medicine and Hygiene (1998) 59:357-362.
Flora, et al., "Dual-micro-Esi source for precise mass determination on a quadrupole time-of-flight mass spectrometer for genomic and proteomic applications" *Anal. Bioanal. Chem.* (2002) 373:538-546.
Fox et al., "Identification and Detection of Bacteria: Electrospray MS-MS Versus Derivatization/GC-MS" *Proceedings of the ERDEC Scientific Conference on Chemical and Biological Defense Research* (1994) 39- 44.
Fox et al., "Identification of Brucella by Ribosomal-spacer-region PCR and differentiation of, Brucella canis from other Brucella spp. pathogenic for humans by carbohdrate profiles" *Journal of Clinical Microbiology* (1998) 36:3217-3222.
Fox et al., "Report of the 'Bioterrorism Workshop Duke University Thomas Center on Apr. 24, 2002 organized by US Army Research Office" Journal of Microbiological Methods (2002) 51:247-254.
Fraser et al., "The Minimal Gene Complement of Mycoplasma Genitalium" *Science* (1995) 270:397-403.
Fuerstenau etal., "Molecular Weight Determination of Megadalton DNA Electrospray Ions Using Charge Detection Time-of-flight Mass Spectrometry" *Rapid Comm. Mass Spec.* (1995) 9:1528-1538.
Fujioka et al., "Analysis of enterovirus genotypes using single-strand conformation polymorphisms of polymerase chain reaction products" *J. Virol. Meth.* (1995) 51:253-258.
Gabriel et al., "Improved mtDNA sequence analysis of forensic remains using a "mini-primer set" amplification strategy" *Journal of Forensic Sciences* (2001) 46:247-253.
Gattermann et al., "Heteroplasmic Point Mutations of Mitochondrial DNA Affecting Subunit I of Cytoclrome c Oxidase in Two Patients with Acquired Idiopathic Sideroblastic Anemia" *Blood* (1997) 90:4961-4972.
Gendel et al., "Computational analysis of the specificity of 16S rRNA-derived signature sequences for identifying food-related microbes" *Food Microbiology* (1996) 13:1-15.
Ginther et al., "Identifying individuals by sequencing mitochondrial DNA from teeth," *Nature Genetics* (1992) 2:135-138.
Giles etal., "Maternal inheritance of human mitochondrial DNA," *PNAS* (1980) 77:6715-6719.
Goto etal., "Applications of the partial 16S rDNA sequence as an index for rapid identification of species in the genus Bacillus" *J. Gen. Appl. Microbiol.* (2000) 46:1-8.
Greenberg et al., "Intraspecific nucleotide sequence variability surrounding the origin of replication in human mitochondrial DNA," *Gene* (1983) 21:33-49.
Griffey et al., "Detection of base pair mismatches in duplex DNA and RNA oligonucleotides using electrospray mass spectrometry" *Proceedings of SPIE - the International Society for Optical Engineering* (1997) 2985:82-86.
Griffin et al., "Direct genetic analysis by matrix-assisted laser desorption/ionization mass spectrometry" *PNAS* (1999) 96:6301-6306.
Griffin etal., "Single-nucleotide polymorphism analysis by MALDI-TOF mass spectrometry" *Trends in Biotechnology* (2000) 18:77-84.
Grzybowski "Extremely high levels of human mitochondrial DNA heteroplasmy in single hair roots" *Electrophoresis* (2000) 21:548-553.
Hahner et al., "Analysis of short tandem repeat polymorphisms by electrospray ion trap mass spectrometry" *Nucleic Acids Research* (2000) 28:E82.
Hannis et al., "Accurate characterization of the tyrosine hydroxylase forensic allele 9.3 through development of electrospray ionization Fourier transform ion cyclotron resonance mass spectrometry" *Rapid* Communications in Mass Spectrometry (1999) 13:954-962.
Hannis et al., "Detection of double-stranded Pcr amplicons at the attomole level electrosprayed from low nanomolar solutions using Ft-Icr mass spectrometry" *Fresenius Journal of Analytical Chemistry* (2001) 369: 246-251.
Hannis et al., "Genotyping short tandem repeats using flow injection and electrospray ionization Fourier transform ion cyclotron resonance mass spectrometry" *Rapid Communications in Mass Spectrometry* (2001) 15:348-350.
Hannis et al., "Genotyping complex short tandem repeats using electrospray ionization Fourier transform ion cyclotron resonance multistage mass spectrometry" *Proceedings of SPIE - the International Society for Optical Engineering* (2000) 3926:36-47.
Haugland et al., "Identification of putative sequence specific Pcr primers for detection of the toxigenic fungal species Stachybotrys chartarum" *Mol. Cell. Probes* (1998) 12:387-396.
Hayashi et al., "Phylogenetic analysis of the human gut microbiota using 16S rDNA clone libraries and strictly anaerobic culture-based methods" *Microbiology and Immunology* (2002) 46:535-548.
Henchal et al., "Sensitivity and specificity of a universal primer set for the rapid diagnosis of dengue virus infections by polymerase chain reaction and nucleic acid hybridization" *American Journal of Tropical* Medicine and Hygiene (1991) 45:418-428.
Herrmann et al., "Differentiation of Chlamydia spp. By Sequence Determination and Restriction Endonuclease Cleavage of RNase p. Rna Genes" *J. Clin. Microbiol.* (1996) 34:1897-1902.
Higgins et al., "Competitive oligonucleotide single-base extension combined with mass spectrometric detection for mutation screening" *BioTechniques* (1997) 23:710-714.
Hoffman et al., "Universal primer set for the full-length amplification of all influenza a viruses" *Archives of Virology* (2001) 146:2275-2289.
Holland et al., "Mitochondrial DNA Sequence Analysis of Human Skeletal Remains: Identification of Remains from the Vietnam War," *Journal of Forensic Sciences* (1993) 38:542-553.
Holm et al., "Removing near-neighbour redundancy from large protein sequence collections" *Bioinformatics* (1998) 14:423-429.
Honda et al., "Universal method of hypersensitive nested PCR toward forensic DNA typing" *International Congress Series* (1998) 7:28-30.
Howell etal., "Persistent Heteroplasmy of a Mutation in the Human mtDNA Control Region: Hypermutation as an Apparent Consequence of Simple-Repeat Expansion/Contraction" *Am. J. Hum. Genet.* (2000) 66:1589-1598.
Hurst et al., "Detection of bacterial DNA polymerase chain reaction products by matrix-assisted laser desorptioniodzation mass spectrometry" *Rapid Commun. Mass. Spec.* (1996) 10:377-382.
Hurst et al., "Maldi-Tof Analysis of Polymerase Chain Reaction Products from Methanotrophic Bacteria" *Anal. Chem.* (1998) 70:2693-2698.
Hutchison etal., "Maternal inheritance of mammalian mitochondrial DNA," *Nature* (1974) 251:536-538.
Ingman et al., "Mitochondrial genome variation and the origin of modern humans" *Nature* (2000) 408:708- 713.
International Search Report for PCT/U502/20336 dated Feb. 3, 2003.
International Search Report for PCT/U503/38795 dated Apr. 19, 2004.
International Prelim. Exam. Report for PCT/U502/20336 dated May 12, 2004.
International Search Report for PCT/U503/38757 dated Jun. 24, 2004.
International Search Report for PCT/U503/38830 dated Aug. 25, 2004.
International Search Report for PCT/U503/38505 dated Apr. 12, 2005.
International Search Report for PCT/U503/38761 dated Dec. 30, 2005.
International Search Report for PCT/U52004/011877 dated Apr. 20, 2006.
International Search Report for PCT/U52005/000386 dated May 9, 2006.
International Search Report for PCT/U52005/018031 dated Jun. 28, 2006.
Isola et al., "Maldi-Tof mass spectrometric method for detection of hybridized DNA oligomers" *Analytical Chemistry* (2001) 73:2126-2131.
Jackson et al., "Mass spectrometry for genotyping: an emerging tool for molecular medicine" *Molecular Medicine Today* (2000) 6:271-276.
Jankowski etal., "Mass spectrometry of DNA. Part 2. Quantitative estimation of base composition" *European Journal of Mass Spectrometry in Biochemistry, Medicine, and Environmental Research* (1980) 1:45-52.
Jansen et al., "Genotype-by-environment Interaction in Genetic Mapping of Multiple Quantitative Trait Loci" *Theor. Appl. Genet.* (1995) 91:33-37.
Jensen et al., "Rapid Identification of Bacteria on the Basis of Polymerase Chain Reaction-Amplified Ribosomal DNA Spacer Polymorphisms" *Appl. Environ. Microbiol.* (1993) 59:945-952.
Jiang et al., "Multiple Trait Analysis of Genetic Mapping for Quantitative Trait Loci Genetics" *Genetics* (1995) 140:1111-1127.
Jiang et al., "A highly efficient and automated method of purifying and desalting PCR products for analysis by electrospray ionization mass spectrometry." *Anal. Biochem.* (2003) 316:50-57.
Johnson et al., "Precise molecular weight determination of Cpr products of the rRNA intergenic spacer region using electrospray quadrupole mass spectroemtry for differentiation of B. subtilis and B. atrophaeus, closely related species of bacilli" *Journal ofMicrobiological Methods* (2000) 40:241-254.
Jurinke et al., "Detection of hepatitis B virus DNA in serum samples via nested PCR and MALDI-TOF mass spectrometry" *Genetic Analysis: Biomolecular Engineering* (1996) 13:67-71.
Kageyama et al., "Rapid detection of human fecal Eubacterium species and related genera by nested Pcr method" *Microbiology and Immunology* (2001) 45:315-318.
Ke etal., "Development of a PCR Assay for Rapid Detection of Enterococci" *Journal of Clinical Microbiology* (1999) 37:3497-3503.
Keller etal., "Empirical Statistical Model to Estimate the Accuracy of Peptide Identifications Made by MS/MS and Database Search" *Anal. Chem* (2002) 74:5383-5392.
Kilpatrick et al., "Group-Specific Identification of Polioviruses by PCR Using Primer Containing Mixed-Base or Deoxyinosine Residues at Positions of Codon Degeneracy" *J. Clin. Microbiol.* (1996) 34:2990-2996.
Krahmer etal., "Electrospray quadrupole mass spectrometry analysis of model oligonucleotides and polymerase chain reaction products: determination of base substitutions, nucleotide additions/deletions, and chemical modifications" *Anal. Chem.* (1999) 71:2893-2900.
Krahmer et al., "MS for identification of single nucleotide polymorphisms and Ms/Ms for discrimination of isomeric PCR products" *Anal. Chem.* (2000) 72:4033-4040.
Kupke et al., "Molecular Characterization of Lantibiotic-synthesizing Enzyme EpiD Reveals a Function for Bacterial Dfp Proteins i Coenzyme a Biosynthesis" *Journal of Biological Chemistry* (2000) 275:31838- 31846.
Lacroix et al., "PCR-Based Technique for the Detection of Bacteria in Semen and Urine" *J. Microbiol. Meth.* (1996) 26:61-71.
Lebedev, Y. et al "Oligonucleotides containing 2-aminoadenine and 5-methycytosine are more effective as primers for Pcr amplification than their nonmodified counterparts" *Genetic Analysis: Biomolecular* Engineering (1996) 13:15-21.
Leif et al., "Isolation and characterization of the proton-translocating NADH: ubiquinone oxidoreductase from Escherichia coli" *Eur. J. Biochem.* (1995) 230:538-548.
Lewers et al., "Detection of Linked Qtl for Soybean Brown Stem Rot Resistance in 'BSR 101' as Expressed in a Growth Chamber Environment" *Molecular Breeding* (1999) 5:33-42.
Li etal., "Single nucleotide polymorphism determination using primer extension and time of flight mass spectrometry" *Electrophoresis* (1999) 20:1258-1265.
Little, et al., "Rapid Sequencing of Oligonucleotides by High-Resolution Mass Spectrometry" *J. Am. Chem. Soc.* (1994) 116:4893-4897.
Little etal., "Maldi on a Chip: Analysis of Arrays of Low-Femtomole to Subfemtomole Quantities of Synthetic Oligonucleotides and Dna Diagnostic Products Dispensed by a Piezoelectric Pipet" *Analytical Chemistry* (1997) 69:4540-4546.
Liu et al., "An unusual gene arrangement for the putative chromosome replication origin and circadian expression of dnaN in Synechococcus sp. Strain PCC 7942" *Gene* (1996) 172:105-109.
Liu et al., "Improving the microdialysis procedure for electrospray ionization mass spectrometry of biological samples" *Journal of Mass Spectrometry* (1997) 32:425-431.
Loakes et al., "Nitroindoles as universal bases" *Nucleosides and Nucleotides* (1995) 14:1001-1003.
Love et al., "Cloning and sequence of the groESL heat-shock operon of Pasteurella multocida" *Gene* (1995) 166:179-180.
Maiwald et al., "Characterization of contaminating DNA in Taq polymerase which occurs during amplification with a primer set for Legionella 5S ribosomal RNA" *Molecular and Cellular Probes* (1994) 8:11-14.
Mangrum et al., "Solution composition and thermal denaturation for the production of single-stranded Pcr amplicons: piperdine-induced destabilization of the DNA duplex?" *Journal of the American Society for Mass Spectrometry* (2002) 13:232-240.

Martemyanov et al., "Extremely Thermostable Elongation Factor G from Aquifex aeolicus: Cloning, Expression, Purification, and Characterization in a Heterologous Translation System" *Protein Expr. Purif* (2000) 18:257-261.

Matray et al., "Synthesis and properties of RNA analogs - oligoribonucleotide N3'->P5' phosphoramidates" *Nucleic Acids Res* (1999) 3976-3985.

Mccabe et al., "Bacterial Species Identification after DNA Amplification with a Universal Primer Pair" *Molecular Genetics and Metabolism* (1999) 66:205-211.

Mclafferty et al., "Comparison of Algorithms and Databases for Matching Unknown Mass Spectra" *J. Am. Soc. Mass Spectrom.* (1998).

Meiyu et al., "Detection of flaviviruses by reverse transcriptase-polymerase chain reaction with the universal primer set" *Microbiology and Immunology* (1997) 41:209-213.

Messmer et al., "Discrimination of Streptococcus pneumoniae from other upper respiratory tract streptococci by arbitrarily primed Pcr" *Clinical Biochemistry* (1995) 28:567-572.

Miller et al., "A compendium of human mitochondrial DNA control region: development of an international standard forensic database," *Croat Med. J.* (2001) 42:315-327.

Moricca etal., "Detection of Fusarium oxysporum Esp. Vas nfectum in cotton tissue by polymerase chain reaction" *Plant Pathology* (1998) 47:486-494.

Morse etal., "Nucleotide Sequence of Part of the ropC Gene Encoding the B Subunit of Dna-Dependent RNA Polymerase from some Gram-Positive Bacteria and Comparative Amino Acid Sequence Analysis" *System Appl. Microbiol.* (1996) 19:150-157.

Muddiman et al., "Application of secondary ion and matrix-assisted laser desorption-ionization time-of-flight mass spectrometry for the quantitative analysis of biological molecules" *Mass Spectrometry Reviews* (1995) 14:383-429.

Muddiman etal., "Important aspects concerning the quantification of biomolecules by time-of-flight secondary-ion mass spectrometry" *Applied Spectroscopy* (1996) 50:161-166.

Muddiman etal., "Characterization of PCR Products from Bacilli Using Electrospray Ionization Fticr Mass Spectrometry" *Anal. Chem.* (1996) 68:3705-3712.

Muddiman etal., "Length and base composition of PCR-amplified nucleic acids using mass measurements from electrospray ionization mass spectrometry" *Anal. Chem.* (1997) 69:1543-1549.

Muddiman etal., "Sequencing and Characterization of Larger Oligonucleotides by Electrospray Ionization Fourier Transform Ion Cyclotron Resonance Mass Spectrometry" *Reviews in Analytical Chemistry* (1998) 17:1-68.

Muddiman etal., "Precise mass measurement of a double-stranded 500 base-pair (309 kDa) polymerase chain reaction product by negative ion electrospray ionization fourier transform ion cyclotron resonance mass spectrometry" *Rapid Commun. Mass Spec.* (1999) 13:1201-1204.

Muhammad et al., "Electrospray ionization quadrupole time-of-flight mass spectrometry and quadrupole mass spectrometry for genotyping single nucleotide substitutions in intact polymerase chain reaction products in K-ras and p53" *Rapid Commun. Mass Spectrom.* (2002) 16:2278-2285.

Mushegian et al., "A minimal gene set for ceullular life derived by comparison of complete bacterial genomes" *Proc. Natl. Acad. Sci.* USA (1996) 93:10268-10273.

Nagpal et al., "Utility of 16S-23S RNA spacer region methodology: how similar are interspace regions within a genome and between strains for closely related organisms?" *Journal of Microbiological Methods* (1998) 33:211-219.

Nakao et al., "Development of a Direct PCR Assay for Detection of the Diphtheria Toxin Gene" *J. Clin. Microbiol.* (1997) 35:1651-1655.

Naumov et al., "Discrimination of the Soil Yest Species Williopsis saturnus and Williopsis suaveolens by the Polymerase Chain Reaction with the Universal Primer N21" *Microbiology (Moscow)(Translation of Mikrobiologiya)* (2000) 69:229-233.

Nilsson etal., "Evaluation of mitochondrial DNA coding region assays for ncreased discrimination in forensic analysis" *Forensic Science International: Genetics* (2008) 2:1-8.

Nishikawa et al., "Reconstitution of active recombinant Shiga toxin (Stx)1 from recombinant Stxl-A and Stxl-B subunits independently produced by E. coli clones" *FEMS* (1999) 178:13-18.

Norder et al., "Typing of Hepatitis B Virus Genomes by a Simplified Polymerase Chain Reaction" *J. Med. Virol.* (1990) 31:215-221.

Null et al., "Preparation of single-stranded PCR products for electrospray ionization mass spectrometry using the Dna repair enzyme lambda exonuclease" *Analyst* (2000) 125:619-626.

Null et al., "Genotyping of Simple and Compound Short Tandem Repeat Loci Using Electrospray Ionization Fourier Transform Ion Cyclotron Resonance Mass Spectrometry" Analytical Chemistry (2001) 73:4514-4521.

Null et al., "Perspectives on the use of electrospray ionization Fourier transform ion cyclotron resonance mass spectrometry for short tandem repeat genotyping in the post-genome era" *Journal of Mass Spectrometry* (2001) 36:589-606.

Null et al., "Evaluation of sample preparation techniques for mass measurements of PCR products using ESI-FT-ICR mass spectrometry" *Journal of the American Society for Mass Spectrometry* (2002) 13:338-344.

Null et al., "Determination of a correction to improve mass measurement accuracy of isotopically unresolved polymerase chain reaction amplicons by electrospray ionization Fourier transform ion cyclotron resonance mass spectrometry" *Rapid Comm. Mass Spectrom.* (2003) 17:1714-1722.

Null et al., "Implications of hydrophobicity and free energy of solvation for characterization of nucleic acids by electrospray ionization mass spectrometry" *Anal. Chem.* (2003) 75:1331-1339.

Parson et al., "Population data for 101 Austrian Caucasian mitochondrial DNA d-loop sequences: Application of mtDNA sequence analysis to a forensic case" *Int. J. Legal Med.* (1198) 111:124-132.

Paterson et al., "Fine Mapping of Quantitative Trait Loci Using Selected Overlapping Recombinant Chromosomes, in an Interspecies Cross of Tomato" Genetics (1990) 124:735-742.

Peng et al., "Rapid detection of Shigella species in environmental sewage by an immunocapture PCR with universal primers" *Applied and Environmental Microbiology* (2002) 68:2580-2583.

Pomerantz et al., "Determination of oligonucleotide composition from mass spectrometrically measured molecular weight" *Journal of the American Society for Mass Spectrometry* (1993) 4:204-209.

Raaum, R. L. etal., "Catarrhine primate divergence dates estimated from complete mitochondria genomes: concordance with fossil and nuclear DNA evidence," *J. Hum. Evol.* (2005) 48:237-257.

Reid etal., "Primary diagnosis of foot-and-mouth disease by reverse transcription polymerase chain reaction" *Journal of Virological Methods* (2000) 89:167-176.

Reilly etal., "Design and use of 16S ribosomal DNA-directed primers in competitive PCRs to enumerate proteolytic bacteria in the rumen" *Microb. Eco*l. (2002) 43:259-270.

Ross et al., "Discrimination of Single-Nucleotide Polymorphisms in Human DNA Using Peptide Nucleic Acid Probes Detected by Maldi-Tof Mass Spectrometry" *Anal. Chem.* (1997) 69:4197-4202.

Ross et al., "Analysis of DNA fragments from conventional and microfabricated Pcr devices using delayed extraction Maldi-Tof mass spectrometry" *Anal. Chem.* (1998) 70:2067-2073.

Sala et al., "Ambiguous base pairing of the purine analogue 1-(20deoxy-B-D-ribofuranosyl)-imidazole-4- carboxamide during Pcr" *Nucl. Acids Res.* (1996) 24:3302-3306.

Sauer et al., "A novel procedure for efficient genotyping of single nucleotide polymorphisms" *Nucleic Acids Research* (2000) 28:E13.

Scaramozzino et al., "Comparison of Flavivirus universal primer pairs and development of a rapid, highly sensitive heminested reverse transcription-Pcr assay for detection of flaviviruses targeted to a conserved region of the N55 gene sequences" *J. Clin. Microbio*l. (2001) 39:1922-1927.

Schen A. M. "Genome analysis with gene expression microarrays" Bioessays (1996) 18:427-431.

Schram et al., "Mass Spectrometry of Nucleic Acid Components" *Biomedical Applications of Mass Spectrometry* (1990) 34:203-280.

Schultz et al., "Polymerase chain reaction products analyzed by charge detection mass spectrometry" Rapid Communications in Mass Spectrometry (1999) 13:15-20.

Senko et al., "Determination of Monoisotopic Masses and Ion Populations for Large Biomolecules from Resolved Isotopic Distributions," *J. Am. Soc. Mass Spectrom.* (1995) 6:229.
Seshardi et al., "Differential Expression of Translational Elements by Life Cycle Variants of Coxiella burnetii" *Infect. Immun.* (1999) 67:6026-6033.
Shaver et al., "Variation in 16S-23S rRNA intergenic spacer regions among Bacillus subtilis 168 isolates" *Molecular Microbiology* (2001) 42:101-109.
Shaver et al., "Restriction fragment length polymorphism of rRNA operons for discrimination and intergenic spacer sequences for cataloging Bacillus subtilis sub-groups" *J. Microbiol Methods* (2002) 50:215- 223.
Srinivasan et al., "Matrix-assisted laser desorption/ionization time-of-flight mass spectrometry as a rapid screening method to detect mutations causing Tay-Sachs disease" *Rapid Communications in Mass* Spectrometry (1997) 11:1144-1150.
Steffens et al., "Sequence analysis of mitochondrial DNA hybervariable regions using infrared fluorescence detection" *BioTechniques* (1998) 24:1044-1046.
Stoneking etal., "Population variation of human mDNA control region sequences detected by enzymatic amplification and sequence-specific oligonucleotide probes," *American Journal of Human Genetics* (1991) 48:370-382.
Takahashi etal., "Characterization of gyA, gyB, glA and gr1B mutations in fluoroquinolone-resistant clinical isolates of Staphylococcus aureus" *J. Antimicrob. Chemother* (1998) 41:49-57.
Takeuchi et al., "Serotyping of Adenoviruses on Conjunctival Scrapings by PCR and Sequence Analysis" *Journal of Clinical Microbiology* (1999) 37:1839-1845.
Tatuch et al., "Heteroplasmic mtDNA mutation (T-G) at 8993 can cause Leigh disease when the percentage of abnormal mtDNA is high" Am. *J. Hum. Genet.* (1992) 50:852-858.
Tong etal., "Ligation reaction specificities of an NAD+-dependent DNA ligase from the hyperthermophile Aquifex aeolicus" *Nucleic Acids Res* (2000) 28:1447-1454.
Torroni et al., "Classification of European mtDNAs from an Analysis of Three European Populations" *Genetics* (1996) 144:1835-1850.
Van Aerschot etal., "In search of acyclic analogues as universal nucleosides in degenerate probes" *Nucleosides and Nucleotides* (1995) 14:1053-1056.
Van Baar et al., "Characterization of Bacteria by Matrix Assisted Laser Desorption/Ionization and Electrospray Mass Spectrometry" *FEMS Microbiol. Review* (2000) 24:195-219.
Van Camp et al., "Amplification and sequencing of variable regions in bacteria 23S ribosomal RNA genes with conserved primer sequences" *Current Microbiology* (1993) 27:147-151.
Van Der Vos Sen et al., "DNA based typing, identification and detection systems for food spoilage microorganisms: development and implementation" *Int. J. Food Microbiol.* (1996) 33:35-49.
Van Ert et al., "Mass spectrometry provides accurate characterization of two genetic marker types in Bacillus antlu-acis" *Biotechniques* (2004) 37:642-651.
Vanderhallen et al., "Identification of Encephalomyocarditis Virus in Clinical Samples by Reverse Transcription-Pcr Followed by Genetic Typing Using Sequence Analysis" *J. Clin. Microbiol.* (1998) 36:3463-3467.
Walters et al., "Genotyping single nucleotide polymorphisms using intact polymerase chain reaction products by electrospray quadrupole mass spectrometry" *Rapid Communications in Mass Spectrometry* (2001) 15:1752-1759.
Welham et al., "The Characterization of Micro-organisms by Matrix-assisted Laser Desorption/Ionization Time-of-flight Mass Spectrometry" *Rapid Communications in Mass Spectrometry* (1998) 12:176-180.
Widjojoatmodjo et al., "Rapid Identification of Bacteria by PCR-Single-Strand Conformation Polymorphism" *Journal of Clinical Microbiology* (1994) 3002-3007.
Wolter et al., "Negative Ion FAB Mass Spectrometric Analysis of Non-Charged Key Intermediates in Oligonucleotide Synthesis: Rapid Identification of Partially Protected Dinucleoside Monophosphates" *Biomed. Environ. Mass Spectrom.* (1987) 14:111-116.
Woo et al., "Identification of Leptospira inadai by continuous monitoring of fluorescence during rapid cycle Pcr" *Systematic and Applied Microbiology* (1998) 21:89-96.
Wunschel et al., "Discrimination Among the B. Cereus Group, in Comparison to B. Subtilis, by Structural Carbohydrate Profiles and Ribosomal Rna Spacer Region Pcr" *System. Appl. Microbiol.* (1994) 17:625- 635.
Wunschel et al., "Analysis of double-stranded polymerase chain reaction products from the Bacillus cereus group by electrospray ionization Fourier transform ion cyclotron resonance mass spectrometry" *Rapid Communications in Mass Spectrometry* (1996) 10:29-35.
Wunschel et al., "Mass spectrometric characterization of DNA for molecular biological applications: Advances using MALDI and ESI" *Advances in Mass Spectrometry* (1998) 14:Chapter 15/377-Chapter 15/406.
Wunschel et al., "Heterogeneity in baciullus cereus Pcr products detected by Esi-Fticr mass spectrometry" *Anal. Chem.* (1998) 70:1203-1207.
Yao et al., "Mass Spectrometry Based Proteolytic Mapping for Rapid Virus Detection" *Anal. Chem.* (2002) 74:2529-2534.
Yasui et al., "A specific oligonucleotide primer for the rapid detection of Lactobacillus lindneri by polymerase chain reaction" *Can. J. Microbiol.* (1997) 43:157-163.
Zeng et al., "Precision Mapping of Quantitative Trait Loci" *Genetics* (1994) 136:1457-1468.
Table listing related applications and office actions and rejections from those related applications.
Unpublished U.S. Appl. No. 10/318,463 filed Dec. 13, 2002.
Unpublished U.S. Appl. No. 11/233,630 filed Sep. 21, 2005.
Aaserud et al., "DNA sequencing with balckbody infrared radioactive dissociation of electrosprayed ions" Int. J. Mass. Spectrom. Ion Processes, (1997) 167-168: 705-712 (Reference not found in.
Adam et al., Molecular structure of the two-dimensional hexon crystalline array and of adenovirus capsid: *Acta Microbiol. Immuno. Hung.* (1998) 45:305-310.
Adam et al., "Intertype specific epitope structure of adenovirus hexon" *Acta Microbiol. Immuno. Hung.* (1998) 45:311-316.
Adam et al., "Characterization of intertype specific epitopes on adenovirus hexons" *Arch. Virol.* (1998) 143:1669-1682.
Adrian et al., "DNA restriction analysis of adenovirus prototypes 1 to 41" *Arch. Virol.* (1986) 91:277- 290.
Adzhar et al., "Universal oligonucleotides for the detection of infectious bronchitis virus by the polymerase chain reaction" *Avian Pathology* (1996) 25:817-836.
Agostini et al. "Complete genome of a JC virus genotype Type 6 from the brain of an African American with progressive multifocal leukoencephalopathy" (1998) 1:267-272.
Akalu et al., "Rapid identification of subgenera of human adenovirus by serological and Pcr assays" *J. Virol Methods* (1998) 71:187-196.
Allaouchiche et al., "Clinical Impact of Rapid Oxacillin Susceptibility Testing Using a PCR Assay in Staphylococcus aureus Bactaeremia" *J. Infect.* (1999) 39(3):198-204.
Allawi, H.T. & Santa Lucia J., Jr. Thermodynamics and Nmr of internal G.T. mismatches in DNA, Biochemistry, 36, 10581-94 (1997).
Altschuel et al., J. Mol. Biol., 215,403-410 (1990).
Altschul et al., Nucl. Acid Res., 25:3389-3402 (1997).
Amano et al., "Detection of influenza virus: traditional approaches and development of biosensors" Anal. Bioanal. Chem. (2005) 381:156-164.
Anderson and Young, Quantitative Filter Hybridization in Nucleic Acid Hybridization (1985).
Anthony et al., "Use of the Polymerase Chain Reaction for Rapid Detection of High-Level Mupirocin Resistance in Staphylococci" Eur. J. Clin. Microbiol. Infect. Dis. (1999) 18(1):30-34.
Application for Grant by David Mitchell Lubmann dated Oct. 25, 1992 and Oct. 29, 1992.
Application for Continuation Grant by David Mitchell Lubmann dated Jun. 10, 1994 and Jun. 24, 1994.
Application for Grant by David Mitchell Lubmann dated Sep. 1, 1994 and Sep. 27, 1994.
Application for Continuation Grant by David Mitchell Lubmann dated Jun. 4, 1996 and Jun. 14, 1996.

U.S. Appl. No. 09/798,007 Office Communication Mailed May 28, 2003.
U.S. Appl. No. 09/891,793 Office Communication Mailed May 19, 2003 interview summary report.
U.S. Appl. No. 09/891,793 Office Communication Mailed May 23, 2003.
U.S. Appl. No. 09/891,793 Office Communication Mailed Jul. 22, 2008.
U.S. Appl. No. 10/156,608 Office Communication Mailed May 23, 2005.
U.S. Appl. No. 10/323,438 Office Communication Mailed Nov. 20, 2003.
U.S. Appl. No. 10/323,438 Office Communication Mailed Jul. 26, 2004.
U.S. Appl. No. 10/325,527 Office Communication Mailed Dec. 3, 2003.
U.S. Appl. No. 10/325,527 Office Communication Mailed Aug. 16, 2004.
U.S. Appl. No. 10/325,527 Office Communication Mailed Mar. 11, 2005.
U.S. Appl. No. 10/326,642 Office Communication Mailed Nov. 21, 2003.
U.S. Appl. No. 10/326,642 Office Communication Mailed Jul. 14, 2004.
U.S. Appl. No. 10/660,998 Office Communication Mailed Apr. 7, 2009.
U.S. Appl. No. 10/754,415 Office Communication Mailed Jun. 4, 2009.
U.S. Appl. No. 10/829,826 Office Communication Mailed Jul. 6, 2007.
U.S. Appl. No. 10/829,826 Office Communication Mailed Apr. 4, 2008.
U.S. Appl. No. 10/829,826 Office Communication Mailed Dec. 10, 2008.
U.S. Appl. No. 10/844,938 Office Communication Mailed Feb. 2, 2007.
U.S. Appl. No. 10/844,938 Office Communication Mailed Aug. 7, 2007.
U.S. Appl. No. 10/844,938 Office Communication Mailed May 20, 2008.
U.S. Appl. No. 10/844,938 Office Communication Mailed Jan. 30, 2009.
U.S. Appl. No. 10/891,337 Office Communication Mailed Apr. 20, 2009.
U.S. Appl. No. 10/933,928 Office Communication Mailed Jun. 02, 2006.
U.S. Appl. No. 10/943,344 Office Communication Mailed Feb. 27, 2007.
U.S. Appl. No. 10/943,344 Office Communication Mailed May 21, 2008.
U.S. Appl. No. 10/943,344 Office Communication Mailed Feb. 23, 2009.
U.S. Appl. No. 11/060,135 Office Communication Mailed Mar. 25, 2008.
U.S. Appl. No. 11/060,135 Office Communication Mailed Jan. 2, 2009.
U.S. Appl. No. 11/060,135 Office Communication Mailed Jul. 15, 2009.
U.S. Appl. No. 11/070,634 Office Communication Mailed Jul. 23, 2009.
U.S. Appl. No. 11/136,134 Office Communication Mailed Jun. 20, 2007.
U.S. Appl. No. 11/136,134 Office Communication Mailed Mar. 26, 2008.
U.S. Appl. No. 11/136,134 Office Communication Mailed Oct. 31, 2008.
U.S. Appl. No. 11/136,134 Office Communication Mailed Feb. 12, 2009.
U.S. Appl. No. 11/136,134 Office Communication Mailed May 21, 2009.
U.S. Appl. No. 11/331,978 Office Communication Mailed Jun 2, 2008 (interview summary).
U.S. Appl. No. 11/404,561 Office Communication Mailed May 16, 2008.
U.S. Appl. No. 11/404,561 Office Communication Mailed Feb. 4, 2009.
U.S. Appl. No. 11/409,535 Office Communication Mailed Apr. 16, 2008.
U.S. Appl. No. 11/491,376 Office Communication Mailed Apr. 22, 2009.
U.S. Appl. No. 11/582,859 Office Communication Mailed Oct. 21, 2008.
U.S. Appl. No. 11/582,863 Office Communication Mailed Aug. 20, 2007.
U.S. Appl. No. 11/582,863 Office Communication Mailed Jun. 17, 2008.
U.S. Appl. No. 11/582,863 Office Communication Mailed Feb. 26, 2009.
U.S. Appl. No. 11/582,930 Office Communication Mailed Sep. 14, 2007.
U.S. Appl. No. 11/582,930 Office Communication Mailed May 2, 2008.
U.S. Appl. No. 11/582,930 Office Communication Mailed Oct. 24, 2008.
U.S. Appl. No. 11/582,930 Office Communication Mailed Jan. 16, 2009.
U.S. Appl. No. 11/582,930 Office Communication Mailed Jul. 2, 2009.
U.S. Appl. No. 11/754,163 Office Communication Mailed Jul. 28, 2009.
U.S. Appl. No. 11/754,174 Office Communication Mailed Aug. 3, 2009.
U.S. Appl. No. 11/754,182 Office Communication Mailed Jul. 2, 2009.
U.S. Appl. No. 12/211,641 Office Communication Mailed Apr. 17, 2009.
U.S. Appl. No. 90/010,447 Office Communication Mailed Apr. 24, 2009.
U.S. Appl. No. 90/010,448 Office Communication Mailed Apr. 24, 2009.
Arbique et al., "Comparison of the Velogene Rapid MRSA Identification Assay, Denka MRSA-Screen Assay, and BBL Crystal MRSA ID System for rapid identification of methicillin-resistant Staphylococcus aureus" Diagn. Microbiol. Infect. Dis. (2001) 40(1-2):5-10.
Archer, G. L. et al., "Detection of Methicillin Resistance in Staphylococci by Using a DNA Probe," *Antimicrob. Agents Chemother*. (1990) 34(9): 1720-1724.
Armstrong, P. et al., "Sensitive and Specific Colorimetric Dot Assay to Detect Eastern Equine Encephalomyelitis Viral RNA in Mosquitoes After PCR Amplification" *J. Med, Entomol*. (1995) 32(1): 42-52.
Aronsson et al., Persistence of the influenza A/WSN/33 virus RNA at midbrain levels of immunodefective mice, Online Publication Date: Apr. 1, 2001, Journal of the NeuroVirology 7:117- 124, 2001.
Ausubel et al., Current Protocols in Molecular Biology (Relevant portions of the book).
Avellon et al. "Rapid and sensitive diagnosis of human adenovirus infections by a generic polymerase chain reaction" *J. Virol. Methods* (2001) 92:113-120.
Azevedo et al. "Detection of influenza, parainfluenza, adenovirus and respiratory syncytial virus during asthma attacks in children older than two years old." Allergol. Immunopathol. (2003) 31:311- 317.
Baba et al., "Genome and virulence determinants of high virulence community-acquired MRSA" Lancet (2002) 359:1819-1827.
Bai, J, T.H. Liu and D.M.. Lubman, "Matrix-Assisted Laser Desorption/lonization Mass Spectrometry of Restriction Enzyme-Digested Plasmid DNA Using an Active Nafion Substrate," 8 Rapid Commun. Mass Spectrom. 687-691 (1994) (787 reexamination).
Banik et al. "Multiplex PCR assay for rapid identification of oculopathogenic adenoviruses by amplification of the fiber and hexon genes" *J. Clin. Microbiol* (2005) 43:1064-1068.
Baron, E. J., "Genetic Aspects of Methicillin Resistance in Staphylococcus aureus and Methods Used for its Detection in Clinical Laboratories in the United States," *J. Chemother*. (1995) 7(Suppl. 3): 87-92.

Barr et al., "An Influenza a(H3) Reassortant Was Epidemic in Australia and New Zealand in 2003" *J. Med. Virol.* (2005) 76:391-397.
Barski, P. et al., "Rapid assay for detection of methicillin-resistant Staphylococcus aureus using multiplex Pcr," *Mol. Cell Probes* (1996) 10:471-475.
Beall, B., et al. "Survey of emm Gene Sequences and T-Antigen Types from Systemic Streptococcus pyogenes Infection Isolates Collected in San Francisco, California; Atlanta, Georgia; and Connecticut in 1994 and 1995" (1997), J. Clin. Micro. 35, 1231-1235.
Beall et al., "Sequencing emm-Specific Pcr Products for Routine and Accurate Typing of Group a Streptococci" (1996) J. Clin. Micro. 34, 953-958.
Benko, M. et al., "Family Adenoviridae", Virus taxonomy, VIIIth report of the International Committee on Taxonomy of Viruses (2004) Fauquet, C.M. et al. (Eds.) Academic Press, New York, pp. 213-228.
Berencsi, G. et al., "Molecular Biological Characterization of Adenovirus DNA", Acta Microbiol. Immunol. Hung, 1998, Vol. 45, Nos. 3-4; pp. 297-304.
Bisno, a.L. (1995) in Principles and Practice of Infectious Diseases, eds., Mandell, G.L., Bennett, J.E. & Dolin, R. (Churchill Livingston, New York), Vol. 2, pp. 1786-1799.
Blaiotta, G. et al., "Pcr detection of staphylococcal enterotoxin genes in Staphyiococcus spp. strains isolated from meat and dairy products. Evidence for new variants of seG and sel in S. aureus Ab-8802," *J. Appl. Microbiol.* (2004) 97:719-730.
Bolton and McCarthy, Proc. Natl. Acad. Sci. U.S.A., 48, 1390 (1962).
Bont, Thomas et al., "Matrix-assisted laser desorption/ionization time-of-flight mass spectrometry-based detection of microsatellite instabilities in coding Dna sequences: a novel approach to identify Dna-mismatch repair-deficient cancer cells," Clinical Chemistry, 49(4):552-561 Apr. 2003.
Boubaker, K. et al., "Panton-Valentine Leukocidin and Staphyloccoccal Skin Infections in Schoolchildren," *Emerg.Infct. Dis.* (2004) 10(1):121-124.
Bowers, K. M. et al., "Screening for methicillin resistance in Staphylococars aureus and coagulase-negative staphylococci: evaluation of three selective and Mastalex-MRSA latex agglutination," *Br. J. Biomed. Sci.* (2003) 60(2):71-74.
Brakstad, O. G, et al., "Multiplex polylnerase chain reaction for detection of genes for Staphylococcus aureus themonuclease and methicillin resistance and correlation with oxacillin resistance," *APMIS* (1993) 101:681-688.
Brakstad, O. G. et al., "Direct identification of *Staphylococcus aureus* in blood cultures by detection of the gene, encoding the thermostable nuclease or the gene product," *APMIS* (1995) 103:209-218.
Brandt, C.D., et al., "Infections in 18,000 Infants and Children in a Controlled Study of Respiration Tract Disease. I. Adenovirus Pathogenicity in Relation to Serologic Type and Illness Syndrome," Am. J. Epidemio.; 1969, vol. 90, No. 6, pp. 484-500.
Brayshaw, D. P., "Methicillin-resistant Staphylococcus aureus : evaluation of detection techniques on laboratory-passaged organisms," *Br. J Biomed. Sci.* (1999) 56:170-176.
Brightwell et al., "Development of internal controls for PCR detection of Bacillus anthracis" Molecular and Cellular Probes (1998) 12(6):367-377.
Brightwell, G. et al., "Genetic targets for the detection and identifiaction of Venezuelan equine encephalitis viruses," Arch. Virol (1998) 143(4): 731-742.
Bronzoni, R. V. M. et al., "Multiplex nested PCR for Brazilian Alphavirus diagnosis," *Trans. R. Soc. Trop. Med. Hyg.* (2004) 98(8): 456-461.
Bronzoni, R. V. M. et al., "Duplex Reverse Transcription-PCR Followed by Nested PCR Assats for Detection and Identification of Brazilan Alphaviruses and Flaviviruses." *J. Clin. Microbiol.* (2005) 43(2): 696-702.
Brown, "Advances in Molecular Diagnostics for Avian Influenza" Dev. Biol. (2006) 124:93-97.
Brownstein et al., "Modulation of Non-Templated Nucleotide Addition by Taq DNA Polymerase: Primer Modifications that Facilitate Genotyping" BioTechniques (1996) 20:1004-1010.
Brunaud et al., "T-Dna integration into the Arabidopsis genome depends on sequences of pre-insertion sites" Embo Rep. (2002) 3(12):1152-1157.
Buck et al., "Design Strategies and Performance of Custom DNA Sequencing Primers" Biotechniques (1999) 27:528-536.
Butel et al. "Cell and molecular biology of simian virus 40: implications for human infections and diseases" J. Natl. Cancer Institute (1999) 91(2):119-134.
Butler "DNA profiling and quantitation of human DNA" CCQM BAWG 04122005.
Carroll, K. C. et al., "Rapid Detection of the Staphylococcal mec A Gene from Bactec Blood Culture Bottles by the Polymerase Chain Reaction," *Am. J. Clin. Pathol.* (1996) 106:600-5.
Cattoli et al., "Comparison of three rapid detection systems for type a influenza virus on tracheal swabs of experimentally and naturally infected birds" Avian Pathology (2004) 33(4):432-437.
Cavassini, M. et al., "Evaluation of Mrsa-Screen, a Simple Anti-Pbp 2a Slide Latex Agglutination Kit, for Rapid Detection of Methicillin Resistance in Staphylococcus aureus," *J. Clin. Microbial.* (1999) 37(5): 1591-1594.
Chamberlin et al., "New RNA polymerase from Escerichia coli infected with bacteriophage T7" Nature 228:227 (1970).
Chandra, S. et al., "Virus reduction in the preparation and intravenous globulin: in vitro experiments," *Transfusion* (1999) 39(3): 249-257.
Chaves, F. et al., "Molecular Characterization of Resistance to Mupirocin in Methidlin-Susceptible and -Resistant Isolates of Staphylococcus aureu s from Nasal Samples," J. Clin. Microbiol. (2004) 42(2):822-824.
Chen, Y. Z. et al., "A BAC-Based STS-Content Map Spanning a 35-Mb Region of Human Chromosome 1p35-36," Genomics (2001) 74(1):55-70.
Chen et al., "Genetic mapping of the cold-adapted phenotype of B/Ann Arbor/1/66, the master donor virus for live attenuated influenza vaccines (FluMist)" Virology (2006) 345:416-423.
Chen, CH, K. Tang, N. Taranenko and S. Allman, "Laser Desorption Mass Spectrometry for Fast DNA Sequencing," (Nov. 1994), http://www.ornl.gove/sci/techresources/ man_Genome/publicat/94SANTA/sequencing/seqtoc.shtml (787 reexamination).
Chmielewicz, B. et al., "Development of a PCR-Based Assay for Detection, Quantification, and Genotyping of Human Adenoviruses," Clin. Chem., 2005, vol. 51, No. 8, pp. 1365-1373.
Choi et al., "Detection and subtying of swine influenza H1N1, H1N2 and H3N2 viruses in clinical samples using two multiplex RT-PCR assays" J. Virol. Methods (2002) 102:53-59.
Choi, S. et al., "Real-Time PCR Quantification of Human Adenoviruses in Urban Rivers Indicates Genome Prevalence but Low Infectivity," Appl. Environ. Microbiol., 2005, vol. 71, No. 11, pp. 7426- 7433.
Christel, La et al., "Rapid, Automated Nucleic Acid Probe Assays Using Silicon Microstructures for Nucleic Acid Concentration" J. Biomech. Eng., 1999, 121, 22-27.
Claas, E.C.J. et al., "Internally Controlled Real-Time PCT Monitoring of Adenovirus DNA Load in Serum or Plasma of Transplant Recipients," J. Clin. Microbiol., 2005, vol. 43, No. 4, pp. 1738-1744.
Cloney, L. et al., "Rapid detection of mecA in methicillin resistant *Stuphylococcus* aureus using cycling probe technology," Mo/. Cell Probes (1999) 13:191-197.
Contreras-Salazar et al. "up regulation of the Epstein-Barr virus (EBV)-encoded membrane protein Lmp in the Burkitt's lymphoma line Daudi after exposure to n-Butyrate and after EBV superinfection" J. Virol. (1990) 64(11):5441-5447.
Couto, I. et al., "Devetopment of Methicillin Resistance in Clinical Isolates of *Staphylococcus sciuri* by Transcriptional Activation of the mecA Homologue Native to the Species," *J. Bacteriol.* (2003) 185(2):645-653.
Crawford-Miksza, L.K. et al., "Analysis of 15 Adenovirus Hexon Proteins Reveals the Location and Structure of Seven Hypervariable Regions Containing Serotype-Specific Residues," J. Virol., 1996, vol. 70, No. 3, pp. 1836-1844.
Crawford-Miksza, L.K. et al., "Adenovirus Serotype Evolution is Driven by Illegitimate Recombination in the Hypervariable Regions of the Hexon Protein," Virol., 1996, vol. 224, pp. 357-367.

Crawfor-Miksza et al., "Strain variation in adenovirus serotypes 4 and 7a causing acute respiratory disease." (1999) 37:1107-1112.
Cui, L. et al., "Contribution of a Thickened Cell Wall and Its Glutamine Nonamidated Component to the Vancomnycin Resistance Expressed by *Staphylococcus aureus* Mu50,"*Antimicrob. Agents Chemother*. (2000) 44(9):2276-2285.
De Sousa, M. A. et al., "Bridges from hospitals to the laboratory: genetic portraits of methicillin-resistant Staphylococcus aureus clones," *FEMS lmmunol. Med. Microbiol*. (2004) 40:101-111.
De Jong, J.C. et al., "Adenoviruses from Human Immunodeficiency Virus-Infected Individuals, Including Two Strains That Represent New Candidate Serotypes Ad50 and Ad51 of Species B1 and D, Respectively," J. Clin. Microbiol., 1999, vol. 37, No. 12, pp. 3940-3945.
Del Vecchio, V. G. et al., "Molecular Genotyping of Methicillin-Resistant Staphylococcus aureus via Fluorophore-Enhanced Repetitive-Sequence Pcr," *J. Clin. Microbiol*. (1995) 33(8):2141-2144.
Deurenberg et al., "Rapid detection of Panton-Valentine leukocidin from clinical isolates of Staphylococcus aureus strains by real-time PCR" FEMS Microbiol. Lett. (2004) 240(2):225-228.
Di Guilmi, a.M. et al., "Human adenovirus serotype 3 (Ad3) and the Ad3 fiber p[protein bind to a 130- kDa membrane protein on HeLa cells," Virus Res., 1995, Vol. 38, pp. 71-81.
Diep, B. A. et al., "Complete genome sequence of USA300, an epidemic clone of community acured meticillin-resistant *Staphylococcus aures*, " *Lancent* (2006) 367:731-739.
Donehower, et al., "The use of primers from highly conserved pol regions to identify uncharacterized retroviruses by the polymerase chain reaction," J. Vir. Methods (1990) 28:33-46.
Donofrio et al., "Detection of influenza a and B in respiratory secretions with the polymerase chain reaction" Pcr methods and applications, Cold Spring Harbor Lab. Press Vol. 1, No. 4, (1992) pp263-268.
Doty et al., Proc. Natl. Acad. Sci. USA 46:461 (1960).
Drosten et al., New England Journal of Medicine, 2003, 348, 1967.
EBI Accession No. AEM14131 (Jan. 11, 2007) - Bacterial DNA PCR Primer Seq ID No:874.
Ebner, K. et al., "Molecular Detection and Quantitative Analysis of the Entire Spectrum of Human Adenoviruses by a Two-Reaction Real-Time Pcr Assay," J. Clin. Microbiol., 2005, vol. 43, No. 7, pp. 3049-3053.
Ebner et al., "Typing of human adenoviruses in specimens of immunosuppressed patients by PCR-fragment length analysis and real-time quantitative PCR" Journal of Clinical Microbiology (2006) 44:2808-2815.
Echavarria, M. et al., "PCr Method for Detection of Adenovirus in Urine of Healthy and Human Immunodeficiency Virus-Infected Individuals," J. Clin. Microbiol., 1998, vol. 36, No. 11, pp. 3323-3326.
Echavarria, M. et al., "Detection of Adenoviruses (AdV) in Culture-Negative Environmental Samples by Pcr During an AdV-Associated Respiratory Disease Outbreak," J. Clin. Microbiol., 2000, Vol. 38, No. 8, pp. 2982-2984.
Echavarria, M. et al., "Prediction of severe disseminated adenovirus infection by serum PCr," Lancet, 2001, vol. 358, pp. 384-385.
Echavarria, M. et al., "Rapid Detection of Adenovirus in Throat Swab Specimens by PCR During Respiratory Disease Outbreaks among Military Recruits", J. Clin. Microbiol., 2003, vol. 41, No. 2, pp. 810-812.
Echavarria, M. et al "Use of PCR to demonstrate of Adenovirus Species B, C, of F as Well as Coinfection with Two Adenovirus Species in Children with Flu-Like Symptoms", J. Clin. Microbiol, 2006, vol. 44, No. 2, pp. 625-627.
Ecker et al., "Rapid identification and strain-typing of respiratory pathogens for epidemic surveillance" PNAS (2005) 102(22):8012-8017.
Ecker et al., "The Ibis T5000 Universal Biosensor: An Automated Platform for Pathogen Identification and Strain Typing" JALA (2006) 11:341-351.
Edwards, K.M. et al., "Adenovirus Infections in Young Children", Pediatrics, 1985, Vol. 76, No. 3, pp. 420-424.
Ellis et al., "Molecular diagnosis of influenza" Rev. Med. Virol. (2002) 12(6):375-389.
Elsayed, S. et al., "Development and Validation of a Molecular Beacon Probe-Based Real-Time Polymerase Chain Reaction Assay for Rapid Detection of Methicillin Resistance in *Staphylococcus aureus* ," *Arch. Pathol. Lab. Med.* (2003) 127945-849.
EMBL Accession AJ552897 (Mar. 29, 2003).
EMBL Accession AR321656 (Aug. 12, 2003).
EMBL Accession L15697 (Mar. 4, 2000).
EMBL Accession AB068711 (May 21, 2003).
EMBL Accession Z48571 (Jun. 9 1995).
Enright, M. C, et al., "Multilocus Sequence Typing for Characterization of Methicillin-Resistant and Methicillin-Susceptible Clones of Staphylococcus aureus," *J. Clin. Microbial.* (2000) 38(3): 1008-1015.
Enright, M. C. et al., "The evolutionary history of methicillin-resistant *Staphylococcus aureus* (MRSA)," PNAS(2002) 99(11): 7687-7692.
Enright, M. C. et al., "The evolution of a resistant pathogen--the case of MRSA," *Curr. Opin.* Pharmacol. (2003) 3:474-479.
Enright, M.C., et al., "Multilocus Sequence Typing of Streptococcus pyogenes and the Relationships between emm Type and Clone" Infection and Immunity, 2001, 69, 2416-2427.
Erlich (ed.). PCR Technology, Stockton Press (1989).
Evans & Wareham, "Practical Algorithms for Universal DNA Primer Design: an Exercise in Algorithm Engineering".
European Patent Office Communication for 06849755.1 dated Mar. 12, 2008.
European Supplemental Search Report for 02709785.6-2405 (PCT/US0206763) dated Oct. 12, 2005.
European Supplemental Search Report for 04752257.8 dated Feb. 15, 2006.
European Supplemental Search Report for 05751872.2 dated Jan. 28, 2008.
European Supplemental Search Report for 05856582.1 dated Nov. 10, 2008
European Supplemental Search Report for 04775904.8 dated Jul. 25, 2008.
European Supplemental Search Report for 05856582.1 dated Nov. 10, 2008.
Facklam, R., et al., "emm Typing and Validation of Provisional M Types for Group a Streptococci" (1999) Emerging Infectious Diseases, 5, 247-253.
Fang, H. et al., "Rapid Screening and Identification of Methicillin-Resistant *Staphylococcus aureus* from Clinical Samples by Selective-Broth and Real-Time Pcr Assay," *J. Clin. Microbial*. (2003) 41 (7):2894-2899.
Farrell, D. J., "The Reliability of Microscan Conventional and Rapid Panels to Identify Staphylococcus aureus and Detect Methicillin Resistance: An Evaluation Using the Tube Coagulase Test and *mec A* PCR," *Pathology* (1997) 29:406-410.
Fedele C Get al., "Multiplex polymerase chain reaction for the simultaneous detection and typing of polyomavirus JC, BK, and 5V40 DNA in clinical samples", Journal of Virological Methods, 82(2), Oct. 1999, pp. 137-144.
Fedele C G et al., "Quantitation of polyomavirus DNA by a competitive nested polymerase chain reaction," Journal of Virological Methods, 88(1):51-61 (Jul. 2000).
Feng, P., "Impact of molecular biology on the detection of food pathogens" Mol. Biotechnol., 1997, 7, 267-278.
Fong, W. K., et al., "Rapid Solid-Phase Immunoassay for Detection of Methicillin-Resistant *Staphylococcus aureus* Using Cycling Probe Technology." *J. Clin. Microbiol.* (2000) 38(7): 2525- 2529.
Fox, J.P. et al., "The Virus Watch Program: A Continuing Surveillance of Viral Infections in Metropolitan New York Families", Am. J. Epidemiol., 1969, vol. 89, No. 1, pp. 25-50.
Francois et al. "Sequence-specific recognition and cleavage of duplex DNA via triple-helix formation by oligonucleotides covalently linked to a phenanthroline-copper chelate" Proc. Natl. Acad. Sci. USA (1989) 86:9702-9706.
Francois, P. et al., "Rapid Detection of Methicillin-Resistant *Staphylococcus aureus* Directly from Sterile or Nonsterile Clinical Samples by a New Molecular Assay," *J. Clin. Microbiol.* (2003) 41(1):254-260.

Freiberg et al. Genome-wide mRNA profiling: impact on compound evaluation and target identification in anti-bacterial research. Targets 1(1):20-29 (2002).
Freymuth et al., "Comparison of Multiplex Pcr Assays and Conventional Techniques for the Diagnostic of Respiratory Virus Infections in Children Admitted to Hospital with an Acute Respiratory Illness" J. Med. Virol. (2006) 78(11):1498-1504.
Freymuth, F. et al., "Detection of respiratory syncytial virus, parainfluenzavirus 3, adenovirus and rhinovirus sequences in respiratory tract of infants by polymerase chain reaction and hybridization", Clin. Dian. Virol, 1997, vol. 8, pp. 31-40.
Fujimoto, T. et al., "Single-Tube Multiplex PCR for Rapid and Sensitive Diagnosis of Subgenus B and Other Subgenera Adenoviruses in Clinical Samples", Microbiol. Immunol., 2000, vol. 44, No. 10, pp. 821-826 (abstract only).
Fujimura, S, et al., "Characterization of the *mupA* Gene in Strains of Methicillin-Resistant Staphylococcus aureus with a Low Level of Resistance to Mupirocin," *Antimicrob. Agents Chemother*. (2001) 45(2):641-642.
Fujimura, S. et al., "Isoleucyl-tRNA Synthetase Mutations in *Staphylococcus aureus* Clinical Isolates and in Vitro Selection of Low-Level Mupirocin-Resistant Strains," *Antimicrob. Agents Chemother*. (2003) 47(10): 3373-3374.
Gall, J.G.D. et al., "Construction and Characterization of Hexon-Chimeric Adenoviruses: Specification of Adenovirus Serotype", J. Virol, 1998, Vol. 72, No. 12, pp. 10260-10264.
Gammelin et al., "Two Subtypes of Nucleoproteins (NP) of Influenza a Viruses" Virology (1989) 170:71-80.
Gaydos, C.A. et al., "Adenovirus Vaccines in the U.S. Military", Military Med., 1995, vol. 160, No. 6, pp. 300-304.
Geha et al., "Multiplex PCR for Identification of Methicillin-Resistant Staphylococci in the Clinical Laboratory" J. Clin. Microbiol. (1994) 32:1768-1772.
GenBank Accession No. NC_000913.
GenBank Accession AF304460 (Jul. 11, 2001).
GenBank Accession No. M21150 Apr. 26, 1993.
GenBank Accession No. AF375051.1 (Jun. 26, 2001).
GenBank Accession No. Z48571 (Jun. 9, 1995).
GenBank Accession No. X84646 (Jul. 2, 1995).
GenBank GI:147581 [online] Sept 14, 1992 [retrieved on Jul. 20, 20091 from http://www.ncbi.nlm.nih.gov/sviewer/viewerfqi?147581:OLDID:114614.
Genbank GI:15922990 [online] Oct. 4, 2001 [retrieved on Jun. 22, 2008] retrieved from: http://www.ncbi.nlm.nih.gov/entrez/viewerfcgi?15922990:OLD08:50885 (pp. 1, 12, 15, 148, 216, 476, 722, 723, 725, 881, 1251).
Genbank GI:18542231 [online] Sep. 16, 2003 [retrieved on Jun. 23, 20081 retrieved from http://www.ncbi.nlm.nih.gov/entrez/viewerfcgi?db=nuccore&id=18542231 (2 pages).
GenBank GI:174375 [online] Aug. 11, 1995 [retrieved on Jul. 20, 20091 retrieved from http://www.ncbi.nlm.nih.gov/nuccore/174375.
Genbank GI:21281729 [online], publicly available at least as of May 31, 2002 [retrieved on Apr. 11, 20081, retrieved from: http://www.ncbi.nlm.nih.gov/entrez/viewerfcgi?21281729:OLD11:599579 (pp. 1,723 and 1137).
GenBank GI:42813 [online] Feb. 28, 1992 [retrieved on Jul. 20, 2009] retrieved from the Internet at http://www.ncbi.nlm.nih.gov/sviewer/viewer.fqi?42813:OLDID:25896.
GenBank GI:49243355 [online] Jun. 24, 2004 [retrieved on Jul. 27, 2009] retrieved from http://www.ncbi.nlm.nih.govlsviewer/viewer.fi?49243355:OLD04:1481434.
GenBank GI:73916349 [online] Sep. 30, 2005 [retrieved on Jul. 25, 2009] retrieved from http://www.ncbi.nlm.nih.gov/nuccore/73916349.
GenBank GI:78099429 [online] Mar. 11, 2006 [retrieved on Jul. 22, 20091 retrieved from http://www.ncbi.nlm.nih.gov/sviewer/viewer.fi?78099429:NCBI:12971731.
Gibb et al., "Development and evaluation of a 5' fluorogenic nuclease assay to detect and differentiate between Ebola Virus subtypes Zaire and Sudan", Journal of Clinical Microbiology, 39(11):4125-4130 (Nov. 2001).
Giles et al., "Maternal inheritance of human mitochondria! DNA," *PNAS* (1980) 77:6715-6719.
Gill, S. R. et al., "Insights on Evolution of Virulence and Resistance from the Complete Genome Analysis of an Early Methicillin-Resistant Staphylococcus aureus Strain and a Biofilm-Producing Methicillin-Resistant *Staphylococcus epidemidis* Strain," *J. Bacteriol*. (2005) 187(7): 2426-2438.
Gjoen et al., "Specific detection of coxsackie viruses a by the polymerase chain reaction" Clinical and Diagnostic Virology (1997) 8:183-188.
Golden et al., Pilot Study of COBAS PCR and Ligase Chain Reaction for Detection of Rectal Infections Due to Chlamydia trachomatis, J. Clin. Microbiol., 41(5):2174-2175 (May 2003).
Goto et al., "Applications of the partial 16S rDNA sequence as an index for rapid identification of species in the genus Bacillus" *J. Gen. Appl. Microbiol*. (2000) 46:1-8.
Gravet et al., "Characterization of a novel structural member, LukE-LukD, of the bi-component staphylococcal leucotoxins family" *FEBS Lett*. (1998) 436(2):202-208.
Gray, G.C. et al., "Adult Adenovirus Infections: Loss of Orphaned Vaccines Precipitates Military Respiratory Disease Epidemics", Clin. Infect. Diseases, 2000, vol. 31, pp. 663-670.
Greenberg et al., "Intraspecific nucleotide sequence variability surrounding the origin of replication in human mitochondria! DNA," *Gene* (1983) 21:33-49.
Griffey et al., "Detection of base pair mismatches in duplex DNA and RNA oligonucleotides using electrospray mass spectrometry" *Proceedings of SPIE - the International Society for Optical Engineering* (1997) 2985:82-86.
Griffin et al., "Direct genetic analysis by matrix-assisted laser desorption/ionization mass spectrometry" *PNAS* (1999) 96:6301-6306.
Grondahl, B. et al., "Rapid Identification of Nine Microorganisms Causing Acute Respiratory Tract Infections by Single-Tube Multiplex Reverse Transcription-PCR: Feasibility Study", J. Clin. Microbiol., 1999, vol. 37, No. 1, pp. 1-7.
Grundmann, H. et al., "Emergence and resurgence of meticillin-resistant *Staphylococcus aureus* as a public-health threat," *Lancet* (2006) 368: 874-885.
Gu, Z et al., "Multiplexed, Real-Time PCR for Quantitative Detection of Human Adenovirus", J. Clin. Microbiol., 2003, vol. 41, No. 10, pp. 4636-4641.
Haff et al., "Multiplex Genotyping of PCR Products with Mass Tag-Labeled Primers" Nucleic Acids Research (1997) 25(18):3749-3750.
Heim, A. et al., "Rapid and Quantitative Detection of Human Adenovirus DNA by Real-Time PCR", J. Med. Virol., 2003, vol. 70, pp. 228-239.
Haines, J.D., et al., "Medical response to bioterrorism: Are we prepared?" J. Okla. State Med. Assoc. 2000, 93, 187-196.
Hall et al., "Base composition analysis of human mitochondria! DNA using electrospray ionization mass spectrometry: a novel tool for the identification and differentiation of humans" Analytical Biochemistry (2005) 344:53-69.
Hamdad, F. et al., "Detection of Methicillin/Oxacillin Resistance and Typing in Aminoglycoside-Susceptible Methicillin-Resistant and Kanamycin-Tobramycin-Resistant Methicillin-Susceptible" *Microbial Drug Resistance* (2006) 12(3): 177-185.
Hamels et al., "Consensus PCR and Microarray for Diagnosis of the Genus Staphylococcus, Species, and Methicillin Resistance" BioTechniques (2001) 31(6):1364-1366.
Hanssen, a.M. et al., "SCCmec in staphylococci: genes on the move," *FEMS lmmuol. Med. Microbiol*. (2006) 46:8-20.
Hasebe, F. et al. "Combined Detection and Genotyping of Chikungunya Virus by a Specific Reverse Transcription-Polymerase Chain Reaction," *J. Med. Virol*. (2002) 67(3): 370-374.
Hassan et al., "Inter- and Intraspecies Variations of the 16S-23S rDNA Intergenic Spacer Region of Various Streptococcal Species" Systematic and Applied Microbiology (2003) 26(1):97-103.
Higgins, J.A., et al., Sensitive and Rapid Identification of Biological Threat AgentsHIGGINS et al., "Competitive oligonucleotide single-base extension combined with mass spectrometric detection for mutation screening" BioTechniques (1997) 23:710-714. *Ann. Ny Acad. Sci*., 1999, 894, 130-148.

Hill, F., et al., "Polymerase recognition of synthetic oligodeoxyribonucleotides incorporating degenerate pyrimidine and purine bases," Proc. Natl. Acad. Sci. USA 95:4258-4263 (1998).
Hiramatsu, K. et al., "The emergence and evolution of methicillin-resistant *Staphylococcus aureus* " *Trends Microbiol.* (2001) 9(10):486-493.
Hoffmann et al., "Rescue of influenza B virus from eight plasmids" PNAS (2002) 99:11411-11416.
Hofstadler et al., "TIGER: The universal biosensor" Inter. J. Mass Spectrom. (2005) 242:23-41.
Hodgson et al. Molecular Characterization of the Gene Encoding High-Level Mupirocin Resistance in Staphylococcus aureus J2870. Antimicrobial Agents and Chemotherapy 38(5):1205-1208, May 1994.
Holden, M. T. G. et al., "Complete genomes of two clinical *Staphylocuccus aureus* strain: Evidence for the rapid evolution of virulence and drug resistance," PNAS (2004) 101(26):9786- 9791.
Holland, M.M. And T.J. Parsons "Mitochondria! DNA analsysis_Validation and use for forensic casework" (1999) Forensic Science Review, vol. 11, pp. 25-51.
Holmes et al., "Whole-Genome Analysis of Human Influenza a Virus Reveals Multiple Persistent Lineages and Reassortment among Recent H3N2 Viruses" PLoS Biol. (2005) 3(9):1579-1589.
Hongoh et al., "Evaluation of primers and PCR conditions for the analysis of 16s rRNA genes from a natural environment" FEMS Microbiol. Lett. (2003) 221:299-304.
Hood, E., "Chemical and biological weapons: New questions, new answers" Environ. Health Perspect., 1999, 107:931-932.
Houng, H.-S. H. et al., "Rapid type-specific diagnosis of adenovirus type 4 infection using a hexon-based quantitative fluorogenic PCR", Diagn. Microbiol. Infect. Dis., 2002, vol. 42, pp. 227-236.
Huber et al., On-line cation exchange for suppression of adduct formation in negative-ion electrospray mass spectrometry of nucleic acids." Anal. Chem. (1998) 70:5288-5295.
Huletsky, a. et al., New real-time Pcr assay for rapid detection of methicillin-resistant Staphylococcus aureus directly from specimens containing a mixture of staphylococci. J. Clin. Microbial. (2004) 42(5): 1875-84.
Hung, "Detection of Sars coronavirus RNA in the cerebrospinal fluid of a patient with severe acute respiratory syndrome" Clin. Chem. (2003) 2108.
Hunag, C. et al., "Detection of arboviral RNA directly from mosquito homogenates by reverse transcription-polymerase chain reaction," *J. Virol. Methods* (2001) 94(1-2): 121-128.
Hurdle, J. G. et al., "Analysis of Mupirocin Resistance and Fitness in Staphylococcus aureus by Molecular Genetic and Structural Modeling Techniques," Antimicrob. Agents Chemother. (2004) 48(11):4366-4376.
Hyde-Deruyscher, R. et al., "Polyomavirus early-late switch is not regulated at the level of transcription initiation and is associated with changes in RNA processing" Proc. Natl. Acad. Sci. USA (1988) 85:8993-8997.
IEven, M. et al., "Rapid Detection of Methicillin Resistance in Coagulase-Negative Staphylococci by Commercially Available Fluorescence Test," *J. Clin. Microbiol.* (1995) 33(8):2183-2185.
Ihle et al., "Efficient purification of DNA fragments using a protein binding membrane" *Nucleic Acids Research* (2000) 28:e76.
Inglis, T. J. et al., "Rapid Genotypic Confirmation of Methicillin Resistance," *Pathology* (1996) 28(3):259-261.
Australian Search Report for AU 2003297687 dated Sep. 4, 2008.
Australian Search Report for AU 2003302236 dated Sep. 10, 2008.
Australian Search Report for AU 2004248107 dated Jul. 30, 2008.
Canadian patent office communication for Application No. 2,567,839 dated Mar. 7, 2009.
Canadian patent office communication for Application No. 2,525,498 dated Feb. 5, 2009.
Chinese Office Communication for CN2004800161.9 dated Jun. 12, 2009.
International Prelim. Exam. Report for PCT/US02/20336 dated May 12, 2004.
International Prelim. Exam. Report for PCT/US2005/033707 dated Mar. 20, 2007.
International Search Report for PCT/US02/06763 dated Oct. 23, 2002.
International Search Report for PCT/US03/009802 dated Aug. 20, 2004.
International Search Report for PCT/US03/22835 dated Dec. 12, 2003.
International Search Report for PCT/US04/007236 dated Feb. 24, 2006.
International Search Report for PCT/US04/012671 dated Sep. 28, 2007.
International Search Report for PCT/US04/015123 dated Oct. 3, 2005.
International Search Report for PCT/US04/015196 dated Jul. 1, 2005.
International Search Report for PCT/US2004/028869 dated Jul. 17, 2006.
International Search Report for PCT/US04/033742 dated May 15, 2006.
International Search Report for PCT/US05/005356 dated Aug. 7, 2007.
International Search Report for PCT/US05/007022 dated Oct. 20, 2006.
International Search Report for PCT/US05/018337 dated Oct. 10, 2006
International Search Report for PCT/US05/024799 dated Dec. 28, 2006.
International Search Report for PCT/US05/030058 dated Aug. 20, 2007.
International Search Report for PCT/US05/033707 dated Feb. 6, 2006.
International Search Report for PCT/US05/06133 dated Jul. 26, 2007.
International Search Report for PCT/US05/09557 dated Sep. 19, 2005.
International Search Report for PCT/US06/007747 dated Sep. 5, 2006.
International Search Report for PCT/US2006/040747 dated Mar. 17, 2009.
International Search Report for PCT/US06/015160 dated Oct. 10, 2006.
International Search Report for PCT/US2006/061307 dated Jan. 9, 2008.
International Search Report for PCT/US2007/020045 dated Jan. 8, 2009.
International Search Report for PCT/US2007/066194 dated Jan. 15, 2008.
International Search Report for PCT/US2008/054926 dated Jan. 26, 2009.
International Search Report for PCT/US2008/057717 dated Jan. 13, 2009.
International Search Report for PCT/US2008/064891 dated Aug. 28, 2008.
International Search Report for PCT/US2008/057901 dated Jun. 29, 2009.
International Search Report for PCT/US2008/065332 dated Nov. 28, 2008.
Inyaku, K. et al., "Rapid Detection and Identification of Mycobacteria in Sputum Samples by Nested Polymerase Chain Reaction and Restriction Fragment Length Polymorphisms of dnaJ Heat Shock Protein Gene," 42 J. MED. SCI. 21-31 (1993) ('787 reexamination).
Iqbal et al,"A review of molecular recognition technologies for detection of biological threat agents" Biosensors & Bioelectronics, 15:549-578 (2000).
Ito, T. et al., "Structural Comparison of Three Types of Staphylococcal Cassette Chromosome mec Integrated in the Chromosome in Methicillin-Resistant *Staphylococcus aureus*," *Antimicrob. Agents Chemother*. (2001) 45(5): 1323-1336.
Ito, T. et al., "Insights on antibiotic resistance of *Staphylococcus aureus* from its whole genome: genomic istand Scc," *Drug Resist. Updat*. (2003) 6(1):41-52.
Jambrina et al., GenBank: AF005737.1 influenza B virus B/Panama/45/90 polymerase (PB2) mRNA, complete cds, (1997), pp1-3.

Jaulhac, B. et al., "Synthetic DNA probes for detection of genes for enterotoxins a, B, C, D, E and for TSST-1 in staphylococcal strains," *J. Appl. Bacterial.* (1992) 72(5):386-392.

Jeong, J, et al., "Early Screening of Oxacillin-Resistant *Staphylococcus aureus* and *Staphylcoccus epidermidis* from Blood Culture," *J. Korean Med. Sci.* (2002) 17: 168-172.

Jonas, D. et al., "Rapid PCR-Based Identification of Methicillin-Resistant *Staphylococcus aureus* from Screening Swabs," *J. Clin. Microbiol.* (2002) 40(5): 1821-1823.

Jurinke C et al., "Application of nested PCR and mass specctrometry for DNA based virus detection: HBV-DNA detected in the majority of isolated anti-Hbc positive sera", Genetic Analysis: Biomolecular Engineering, Elsevier Science Publishing, US, 14(3):97-102 (Jan. 3, 1998)+A627+A661.

Jurinke et al., "MALDI-TOF Mass Spectrometry. A Versatile Tool for High-Performance DNA Analysis" Molecular Biotechnology (2004) 26(2):147-163.

Kacian et al., "A Replicating RNA Molecule Suitable for a Detailed Analysis of Extracellular Evolution and Replication" Proc. Natl. Acad. Sci. USA 69:3038 (1972).

Kajon, a.E. et al., "Genome Type Analysis of Brazilian Adenovirus Strains of Serotypes 1, 2, 3, 5, and 7 Collected Between 1976 and 1995", J. Med. Virol., 1999, Vol. 58, pp. 408-412.

Katano, H., et al., "Identification of Adeno-associated virus contamination in cell and virus stocks by PCR", Biotechniques, Informa Life Sciences Publishing, Westborough, MA, US, 36(4):676-680 (Apr. 2004).

Katayama, Y. et al., "Genetic Organization of the Chromosome Region Surrounding mecA in Clinical Staphylococcal Strains: Role of 1S431-Mediated mecl Deletion in Expression of Resistance in med-Canying, Low-Level Methicillin-Resistant *Staphylococcus haemolyticus*," *Antimicrob. Agents Chemother.* (2001) 45(7): 1955-1963.

Kearns, A. M. et al., "Rapid detection of methicillin-resistant staphylococci by multiplex PCR," *J. Hosp. Infect.* (1999) 43:33-37.

Khan, A.S., et al., "An outbreak of Crimean-Congo haemorrhagic fever in the United Arab Emirates, 1994-1995" Am. J. Trop. Med. Hyg., 1997, 57, 519-525.

Khan, S. A. et al., "Simultaneous detection of erythromycin-resistant methylase genes ermA and ermC from Staphylococcus spp. By multiplex-Pcr," *Mol. Cell Probes* (1999) 13:381-387.

Kidd, A.H. et al., "Rapid Subgenus Identification of Human Adenovirus Isolates by a General PPCR", J. Clin. Microbiol., 1996, vol. 34, No. 3, pp. 622-627.

Kilbourne, "Influenza Pandemics: Can We Prepare for the Unpredictable?" Viral Immunol. (2004) 17(3):350-357.

Kilbourne, "Influenza Pandemics of the 20th Century" Emerg. Infect. Dis. (2006) 12(1):9-14.

Kim et al. "Identification of Mycobacterial species by comparative sequence analysis of the RNA polymerase gene (rpoB)" Journal of Clinical Microbiology 37(6):1714-1720, Jun. 1999.

Kinney et al., American J. Trop. Med. Hyg., (1998), vol. 59, No. 6, p. 952-954.

Kolbert et al., "Branched-DNA Assay for Detection of the mecA Gene in Oxacillin-Resistant and Oxacillin-Sensitive Staphylococci" J. Clin. Microbiol. (1998) 36:2640-2644.

Krafft, A.E. et al., "Evaluation of PCR Testing of Ethanol-Fixed Nasal Swab Specimens as an Augmented Surveillance Strategy for Influenza Virus and Adenovirus Identification", J. Clin. Microbiol., 2005, vol. 43, No. 4, pp. 1768-1775.

Kramer, L. D. et al., "Dection of St. Louis Encephalitis and Western Equine Encephalomyelitis RNA in Mosquitoes Tested Without Maintainance of a Cold Chain," J. Am. Mosq. Control Assoc. (2001) 17(4): 213-215.

Kramer, L. D. et al., "Dection of Encephalitis Viruses in Mosquitoes (Diptera: Culicidea) and Avian Tissues," *J. Med. Entomol.* (2002) 39(2): 312-323.

Kroes et al., "Bacterial diversity within the human subgingival crevice," Proc. Natl. Acad. Sci. USA (1999) 96:14547-14552.

Kresken, M. et al., "Prevalence of mupirocin resistance in clinical isolates of *Staphylococccus aureus* and *Staphylococcus epidermidis* : results of the Antimicrobial Resistance Surveillance Study of the Paul-Ehrlich-Society for Chemotherapy, 2001," Int. J. Antimicrob. Agents (2004) 23:577-581.

Krishnan, P.U. et al., "Detection of methicillin and mupirocin resistance in Staphylococcus aureus isolates using conventional and molecular methods: a descriptive study from a burns unit with high prevalence of MRSA," J. Clin. Pathol. (2002) 55:745-748.

Krossoy et al., "The putative polymerase sequence of infectious anemia virus suggests a new geneus within the Orthomyxoviridae" Journal of Virology (1999) 73:2136-2142.

Ksiaxek, Thomas G., et al., "A novel coronavirus associated with severe acute respiratory syndrome," New England Journal of Medicine, 348(20):1953-1966 (Apr. 10, 2003).

Kuroda, M., et al., "Whole genome Sequencing of meticillin-resistant Staphylococcus aureus", the Lancet, 357(9264):1225-1240 (Apr. 21, 2001).

Kwok, S. And R. Hguchi, "Avoiding false positives with PCR" Nature, 1989, 339,237-238.

Labandeira-Rey, M. et al., "Staphylococcus aureus Panton Valentine Leukocidin Causes Necrotizing Pneumonia" Sciencexpress (2007) Jan. 18.

Lacroix, L. et al., "Triplex Formation by Oligonucleotides Containing 5-(1-Propynyl)-2'- deoxyuridine: Decreased Magnesium Dependence and Improved Intracellular Gene Targeting" Biochem. (1999) 38(6):1893-1 901.

Lamb et al., "Sequence of Interrupted and Uninterrupted mRNAs and Cloned DNA Coding for the Two Overlapping Nonstructural Proteins of Influenza Virus" Cell (1980) 21:475-485.

Lambert, a.J. et al., "Detection of North American Eastern and Western Equine Encephalitis Viruses by Nucleic Acid Amplification Assays," *J. Clin. Microbiol.* (2003) 41(1): 379-385.

Lau et al., "Nucleic acid sequence-based amplification methods to detect avian influenza virus" Biochem. Biophys. Res. Commun. (2004) 313:336-342.

Lau et al., "A real-time PCR for SARS-coronavirus incorporating target gene pre-amplification" Biochem. Biophys. Res. Comm. (2003) 312:1290-1296.

Lednicky, J. A. et al., "Polyomaviruses and Human Tumors: a Brief Review of Current Concepts and Interpretations," Front. Biosci. (1999) 4:d153-164.

Lee, J.A. et al., "Rapid Identification of Human Adenovirus Types 3 and 7 from Respiratory Specimens via Multiplex Type-Specific PCR", J. Clin. Microbiol., 2005, vol. 43, No. 11, pp. 5509-5514.

Lee, J.H. et al., "Simultaneous Detection of Three Mosquito-Borne Encephalitis Viruses (Eastern equine, La Crosse, and St. Louis) with a Single-Tube Multiplex Reverse Transcriptase Polymerase Chaine Reaction Assay," *J. Am. Mosq. Control Assoc.* (2002) 18(1): 26-31.

Lengyel, a. et al., "Characterization of the Main Protein Components of Adenovirus Virion and its Possible Use in Laboratory Diagnostics", Acta Microbiol. Immunol. Hung., 1998, vol. 43, Nos. 3-4; pp. 281-283.

Leroy et al., "Diagnosis of Ebola haemorrhagic fever by Rt-Pcr in an epidemic setting", Journal of Medical Virology, 60:463-467 (2000).

Letter count for Jambrina et al., GenBank: AF005737.1 influenza B virus B/Panama/45/90 polymerase (PB2) mRNA, complete cds, (1997), pp1-2.

Levi, K. et al., "Evaluation of an Isothermal Signal Amplification Method for Rapid Detection of Methicillin-Resistant Staphylococcus aureus from Patient-Screening Swabs," J. Clin. Microbiol. (2003) 41(7):3 187-3191.

Levine et al., "PCR-based detection of Bacillus anthracis in formalin-fixed tissue from a patient receiving ciprofloxacin" Journal of Clinical Microbiology (2002) 40(11):4360-4362.

Levison et al., "Recent developments of magnetic beads for use in nucleic acid purification" Journal of Chromatography (1998) a 816:107-111.

Le Cann et al., "Quantification of human astroviruses in sewage using real-time RT-PCR" Res. Microbiol. (2004) 155(1):11-15.

Li, Q.-G. et al., "Analysis of 15 Different Genome Types of Adenovirus Type 7 Isolated on Five Continents", J. Virol., 1986, vol. 60, No. 1, pp. 331-335.

Li, Q.-G. et al., "Comparison of 17 Genome Types of Adenovirus Type 3 Identified among Strains Recovered from Six Continents", J. Clin. Microbiol, 1988. vol. 26, No. 5, pp. 1009-1015.

Li, Q.-G. et al., "Genetic variability of hexon loops 1 and 2 between seven genome types of adenovirus serotype 7", Arch. Virol., 1999, vol. 144, No. 9, pp. 1739-1749.

Li et al., "Screening of the high yield influenza B virus on MDCK cell and cloning of its whole genome" International Congress Series 1263 (2004) 610-614.

Li et al., "Evolution of H9N2 influenza viruses from domestic poultry in Mainland China" Virology (2005) 340:70-83.

Liebermann, H. et al., "Mapping of linear epitopes on fibre knob of human adenovirus serotype 5", Virus Res., 2001, vol. 73, No. 2, pp. 145-151.

Liebermann, H. et al., "Mapping of Epitopes on the Fiber Knobs of Human Adenovirus Serotypes 8 and 15", Intervirology, 2002, vol. 45, pp. 59-66.

Lim et al., "The microRNAs of Caenorhabditis elegans" Genes and Development 17:991-1008 (2003).

Limbach, P.A., et al., "Enzymatic Sequencing of Oligonucleotides with Electrospray Mass Spectrometry" 42nd ASMS Conference on Mass Spectrometry (Jun. 1994) ('787 reexamination).

Limoncu, M. H. et al., "Emergence of phenotypic resistance to ciprofloxacin and levofloxacin in methicillin-resistant and methicillin-sensitive Staphylococcus aureus strains," Int. J. Antimicrob. Agents (2003) 21:420-424.

Lin et al., "Oxidative Damage to Mitochondria! DNA in Atrial Muscle of Patients with Atrial Fibrillation," Free Radical Biology and Medicine, 35(10):1310-1318 (2003).

Lin, B. et al., "Use of Oligonucleotide Microarrays for Rapid Detection and Serotyping of Acute Respiratory Disease-Associated Adenoviruses", J. Clin. Microbiol., 2004, vol. 42, No. 7, pp. 3232-3239.

Lina, G. et al., "Involvement of Panton-Valentine Leukocidin-Producing Staphylococcus aurues in Primary Skin Infections and Pneumonia," Clin. Infect. Dis. (1999) 29(5):1128-1132.

Lina, G. et al., "Bacterial Competition for Human Nasal Cavity Colonization: Role of Staphylococcal agr Alleles," Appl. Environ. Microbiol. (2003) 69(1):18-23.

Linssen, B. et al., "Development of Reverse Transcription-Pcr Assays Specific for Detection of Equine Encephalitis Viruses," *J. Clin. Microbio*l. (2000) 38(4): 1527-1535.

Liu et al., "Interregional Transmission of the Internal Protein Genes of H2 Influenza Virus in Migratory Ducks from North America to Eurasia" Virus Genes (2004) 29(1):81-86.

Livermore, D. M., "The threat from the pink corner," Ann. Med. (2003) 35(4):226-234.

Loo, J. A et al., "Applying Charge Discrimination with Electrospray Ionization-Mass Spectrometry to Protein Analysis," J. Am. Soc. Mass. Spectrom. (1995) 6:1098-1104.

Lott, "Nucleotide Sequence Analysis of the 5-8s rDNA and Adjacent IT52 Region of Candida albicans and Related Species" Yeast, 9:1199-1206 (1999).

Louie, L. et al., "Evaluation of Three Rapid Methods for Detection of Methicillin Resistance in Staphylococcus aureus," J. Clin. Microbiol. (2000) 38(6):2170-2173.

Lovseth, A. et al., "Modified Multiplex PCR Method for Detection of Pyrogenic Exotoxin Genes in Staphylococcal Isolates," J. Clin. Microbiol. (2004) 42(8):3869-3872.

Lowe et al., "A computer program for selection of oligonucleotide primers for polymerase chain reactions" Nucleic Acids Research, (1990) vol. 18(7):1757-1761.

Lu, X. et al., "Molecular typing of human adenoviruses by PCR and sequencing of a partial region of the hexon gene", Arch. Virol,., 2006, vol. 15, No. 8, pp. 1587-1602.

Ludwig W. "Bacterial phylogeny based on 16s and 23s rRNA sequence analysis" FE,S Microbiol Rev 15(2-3):155-73, Oct. 1994.

Ludwig, S.L. et al., "Prevalence of Antibodies to Adenovirus Serotypes 4 and 7 among Unimmunized US Army Trainees: Results of Retrospective Nationwide Seroprevalence Survey", J. Infect. Dis., (1998) 178, pp. 1776-1778.

Lukashov, V. V. et al., "Evolutionary Relationships among Parvoviruses: Virus-Host Coevolution among Autonomous Primate Parvoviruses and Links between Adeno-Associated and Avian Parvoviruses," J. Virol. (2001) 75(6):2729-2740.

Ma, X. X. et al., "Novel Type of Staphylococcal Cassette Chromosome mec Identified in Community-Acquired Methicillin-Resistant Staphylococcus aureus Strains," Antimicrob. Agents Chemother. (2002) 46(4):1147-1152.

Mack and Sninsky, "A sensitive method for the identification of uncharacterized viruses related to known virus groups: Hepadnavirus model system," Proc. Natl. Acad. Sci. Usa (1988) 85:6977-6981.

Magnuson, Vl, "Substrate nucleotide-determined non-templated addition of adenine by Taq DNA polymerase: Implications for PCR-based genotyping and cloning" Biotechniques, 21:700-709 (Oct. 1996).

Malasig, M.D. et al "Simplified Microneutralization Test for Serotyping Adenovirus Isolates", J. Clin. Microbiol., 2001, vol. 39, No. 8, pp. 2984-2986.

ManIan, F. A "Asymptomatic Nasal Carriage of Mupirocin-Resistant, Methicillin-Resistant Staphylococcus aureus (MRSA) in a Pet Dog Associated with MRSA Infection in Household Contacts," Clin. Infect. Dis. (2003) 36:e26-e28.

Marmur et al., "Strand Separation and Specific Recombination in Deoxyribonucleic Acids: Biological Studies" Proc. Natl. Acad. Sci. USA 46:453 (1960).

Martineau, F. et al., "Species-Specific and Ubiquitous-DNA-Based Assays for Rapid Identification of Staphylococcus aureus," J. Clin. Microbial. (1998) 36(3):618-623.

Martineau, F. et al., "Development of a PCR Assay for Identification of Staphylococci at Genus and Species Levels," J. Clin. Microbial. (2001) 39(7):2541-2547.

Martin-Lopez, J. V. et al., "Simultaneous PCR detection of ica cluster and methicillin and mupirocin resistance genes in catheter-isolated Staphylococcus," Int. Microbial. (2004) 7:63-66.

Mason et al., "Diversity and linkage of replication and mobilisation genes in Bacillus rolling circle-replicating plasmids from diverse geographical origins" FEMS Microbiol. Ecol. 2002, 42:235-241.

Matsuoka, M. et al., "Characteristic expression of three genes, msrAa), mph(C) and erm(Y), that confer resistance to macrolide antibiotics on Staphylococcus aureus," FEMS Microbiol. Lett. (2003) 220:287-293.

May, "Percent sequence identity: the need to be explicit" Structure (2004) 12(5):737-738.

Mcluckey, S.A., et al., "Ion Trap Tandem Mass Spectrometry Applied to Small Multiply Charged Oligonucleotides with a Modified Base," 5 J. Am. Soc. Mass. Spectrom. 740-747 (1994) (787 reexamination).

Mehrotra et al., "Multiplex PCR for detection of genes for Staphylococcus aureus enterotoxins, exfoliative toxins, toxic shock syndrome toxin 1, and methicillin resistance", Journal of Clinical Microbiology, Washington, DC US 38(3):1032-1035 (Mar. 1, 2000)+256.

Merlino, J. et at., "New Chromogenic Identification and Detection of Staphylococcus aureus and Methicillin-Resistant S. aureus." J. Clin. Microbiol (2000) 38(6): 2378-2380.

Merlino, J. et al., "Rapid Detection of Non-Multidrug-Resistant and Multidrug-Resistant Methicillin-Resistant Staphylococcus aureus Using Cycling Probe Technology for the mecA Gene," Eur. J. Clin. Microbiol. Infect. Dis. (2003) 22: 322.323.

Metzgar, D. et al., "PCR Analysis of Egyptian Respiratory Adenovirus Isolates, Including Identification of Species, Serotypes and Coinfections", J. Clin. Microbiol., 2005, vol. 43, No. 11, p. 5743-5752.

Miragaia, M. et al., "Genetic Diversity among Methicillin-Resistant Staphylococcus epidemidis (MRSE)," Microbial Drug Resistance (2005) 11(2):83-93.

Miura-Ochiai, R. et al., "Quantitative detection and rapid identification of human adenoviruses", J. Clin. Microbiol., 2007, vol. 45, No. 3, pp. 958-967.

Mollet et al. "rpoB sequence analysis as a novel basis for bacterial identification" Molecular Microbiology 26(5):1005-1011 (1997).

Monroy, A.M. et al., "Exvaluation of Reverse Transcriptase Polymerase Chain Reaction for the Detection of Eastern Equine Encephalumyelitis Virus during Vector Surveillance," *J. Med. Entomol*. (1996) 33(3): 449-457.

Moore et al., "Development and Evaluation of a Real-Time Nucleic Acid Sequence Based Amplification Assay for Rapid Detection of Influenza a" J. Med. Virol. (2004) 74(4):619-628.
Morinaga, N. er al., "Purification, Cloning and Charactarizarion of Variant LukE-LukD with Strong Leukocidal Activity of Staphylococcal Bi-Component Leukotoxin Family," Microbiol. Immunol. (2003) 47(1):81-90.
Murakami, K. et al., "Identification of Methicillin-Resistant Strains of Staphylococci by Polymerase Chain Reaction," J. Clin. Microbiol. (1991) 29(10):2240-2244.
Na et al., "Detection and typing of respiratory adenoviruses in a single-tube multiplex polymerase chain reaction" Journal of Medical Virology (2002) 66:512-517.
Nagy, M. et al., "Sequence Analysis of Porcine Adenovirus Serotype 5 Fibre Gene: Evidence for Recombination", Virus Genes, 2002, vol. 24, No. 2, pp. 181-185.
Nakagawa et al., "Gene sequences and specific detection for Panton-Valentine leukocidin" Biochem. Biophys. Res. Commun. (2005) 328(4):995-1002.
Narita et al., "Phage conversion of Panton-Valentine leukocidin in Staphylococcus aureus: molecular analysis of a PVL-converting phage, phiSLT" Gene (2001) 268(1-2):195-206.
Neumann et al., "Host Range Restriction and Pathogenicity in the Context of Influenza Pandemic" Emerg. Infect. Dis. (2006) 12(6):881-886.
New England Biolabs (NEB) Catalog (1998-1999) pp. 1, 79, 121, 284.
Newcombe et al. "PCR of peripheral blood for diagnosis of meningococcal disease" (1996) 34:1637-1640.
Ng et al., "Serial analysis of the plasma concentration of SARS coronavirus RNA in pediatric patients with severe acute respiratory syndrome" Clin. Chem. (2003) 49:2085.
Ng et al., "Quantitative analysis and prognostic implication of SARS coronavirus RNA in the plasma and serum of patients with severe acute respiratory syndrome" Clin. Chem. (2003) 49:1976-1980.
Nordhoff, E., et al., "Matrix Assisted Laser Desorption/lonization Mass Spectrometry of Nucleic Acids with Wavelengths in the Ultraviolet and Infrared" 6 Rapid Commun. Mass Spectrom. 771- 776 (1992) (787 reexamination).
Nubel et al., "PCR primers to amplify 16S rRNA genes from Cyanobacteria," Applied and Environmental Microbiology, 63(8):3327-3332 (Aug. 1997).
Nunes, E. L. et al., "Detection of ileS-2 Gene Encoding Mupirocin Resistance in Methicillin-Resistant Staphylococcus aureus by Multiplex PCR" Diagn. Microbiol. Infect. Dis. (1999) 34(2): 77-81.
Oberacher H et al., "Increased foresnic efficiency of Dna fingerprints through simultaneous resolution of length and nucleotide variability by high-performance mass spectrometry," Human Mutation 29(3):427-432 (Mar. 2008).
Oberacher et al., "Analysis of polymerase chain reaction products by on-line liquid chromatography-mass spectrometry for genotyping of polymeric short tandem repeat loci" (2001) 73:5109-5115.
Oberste, et al., "Molecular phylogeny and proposed classification of the Simian picornaviruses," J. Virol. (2002) 76:1244-1251.
Oberste, et al., "Improved molecular identification of enteroviruses by RT-PCR and amplicon sequencing," J. Clin. Virol. (2003) 26:375-377.
Oberste, et al., "Molecular epidemiology and type-specific detection of echovirus 11 isolates from the Americas, Europe, Africa, Australia, southern Asia and the Middle East," Virus Res. (2003) 91:241- 248.
O'Guinn, M.L. et al., "Field Detection of Eastern Equine Encephalitis Virus in the Amazon Basin Region of Peru Using Reverse Transcription-Polymerase Chain Reaction Adapted for Field Identification of Arthropod-Borne Pathogens," *Am. J. Trop. Med. Hyg.* (2004) 70(2): 164-171.
Oizumi, N, et al., "Relationship between mutations in the DNA gyrase and topoisomerase Iv genes and nadifloxacin resistance in clinically isolated quinolone-resistant Staphylococcus aureus," Journal of Infection and Chemotherapy: Official Journal of the Japan Society of Chemotherapy, 7(3):191-194 (Sep. 2001).
Okada, M. et al., "Detection and sequence-based typing of human adenoviruses using sensitive universal primer sets for the hexon gene", Arch. Virol., 2007, vol. 152, No. 1, pp. 1-9.
Okuma, K. et al., "Dissemination of New Methicillin-Resistant Staphylococcus aureus Clones in the Community," J. Clin. Mcrobiol. (2002) 40(11):4289-4294.
Oliveira, D. C. et al., "Genetic Organization of the Downstream Region of the mecA Element in Methicillin-Resistant Staphylococcus aureus Isolates Carrying Different Polymorphisms of This Region," Antimicrob. dients Chemother. (2000) 44(7): 1906-1910.
Oliveira, D. C. et al., "Multiplex Pcr Strategy for Rapid Identification of Structural Types and Variants of the mec Element in Methicillin-Resistant Staphylococcus aureus," Antimicrob. Agents Chemother. (2002) 46(7):2155-2161.
Osiowy, C. et al., "Direct Detection of Respiratory Syncytial Virus, Parainfluenze Virus, and Adenovirus in Clinical Respiratory Specimens by a Multiplex Reverse Transcription-PCR Assay", J. Clin. Microbiol., 1998, Vol. 36, No. 11, pp. 3149-3154.
Ostrander, E. A. et al., "Identification and Characterization of Dinucleotide Repeat (CA)n. Markers for Genetic Mapping in Dog," Genomics (1993) 16(1):207-213.
Ounissi, H. et al., "Gene Homogeneity for Aminoglycoside-Modifying Enzymes in Gram-Positive Cocci," Antimicrob. Agents Chemother. (1990) 34(11):2164-2168.
Pan, Z.-Q et al., "Oligonucleotide-targeted degradation of U1 and U2 snRNAs reveals differential interactions of simian virus 40 pre-mRNAs with snRNPs," Nucleic Acids Res. (1989) 17(16):6553-6568.
Pastorino, B. et al., "Development of a TaqMan PCR assay without RNA extraction step for the detection and quantification of African Chikungunya viruses," J. Virol. Methods (2005) 124(1-2): 65-71.
Pawa, a. et al., "Co-transfer of plasmids in association with conjugative transfer of mupirocin or mupirocin and penicillin resistance in methicillin-resistant Staphylococcus aureus;" J. Med. Microbiol. (2000) 49: 1103-1107.
Payne et al. Antimicrobials: The challenge of antibiotic resistant bacterial pathogens: the medical need, the market and prospects for new antimicrobial agents. Current Opinion in Microbiology 7:435-438 (2004).
Perez-Roth, E. et al., "Multiplex PCR for Simultaneous Identification of Staphylococcus aureus and Detection of Methicillin and Mupirocin Resistance," J. Clin. Microbial. (2001) 39(11):4037-4041.
Pfeffer, M. et al., "Genus-Specific Detection of Alphaviruses by a Semi-Nested Reverse Transcription-Polymerase Chain Reaction," *Am. J. Trop. Med Hyg.* (1997) 57(6): 709-718.
Pfeffer, M. et al., "Specific Detection of Chikungunya Virus Using a RT-PCR/Nested PCR Combination," *J. Vet. Med. B* (2002) 49(1): 49-54.
Pieles, U, et al., Matrix-Assisted Laser Desorption Ionization Time-of-Flight Spectrometry: a Powerful Tool for the Mass and Sequence Analysis of Natural and Modified Oligonucleotides 21 Nucleic Acids Res. 3191 -31 96 (1993) (787 reexamination).
Pillai, S.D., :Rapid molecular detection of microbial pathogens: breakthroughs and challenges" Arch Virol., 1997, 13 Suppl., 67-82.
Piper, J. et al., "Commercially Available Technique for Rapid Laboratory Detection of Methicillin.
Poddar, S.K., "Detection of adenovirus using PCR and molecular beacon", J. Virol. Methods., 1999, vol. 82, No. 1, pp. 19-26.
Pring-Akerblom, P., et al., "PCR-based detection and typing of human adenoviruses in clinical samples", Res. Virol., 1997, vol. 148, No. 3, pp. 225-231.
Pring-Akerblom, P., et al., "Multiplex Polymerase Chain Reaction for Subgenus-Specific Detection of Human Adenoviruses in Clinical Samples", J. Med. Virol., 1999, vol. 58, No. 1, pp. 87-92.
Promega T4 Polynucleotide Kinase, Promega Technical Bulletin No. 519, Jul. 2002.
Puthavathana et al., "Molecular characterization of the complete genome of human influenza H5N1 virus isolates from Thailand" J. Gen. Virol. (2005) 86:423-433.
Qadri, S. M. et al., "Rapid Detection of Methicillin-Resistant Staphylococcus aureus by Crystal Mrsa Id System,"J. Clin. Microbiol. (1994) 32(7):1830-1832.

Ramisse et al., "Identification and characterization of Bacillus anthracis by multiplex PCR analysis of sequences on plasmids pX01 and pX02 and chromosomal DNA" FEMS Microbiology Letters (1996) 145(1):9-16.
Rangarajan, Sampath, et al., "Rapid identification of emerging infectious agents using PCR and electrospray ionization mass spectrometry" Ann. N. Y. Acad. of Sci (2007) 1102:109-120.
Reischl, Frontiers Biosci., 1996, 1, Application of Molecular Biology-Based Methods to the Diagnosis of Infectious Diseases 1, e72-e77.
Reischl, U. et al., "Rapid Identification of Methicillin-Resistant Staphylococcuss aureus and Simultaneous Species Confirmation Using Real-Time Fluorescence PCR," J. Clin. Microbiol. (2000) 38(6):2429-2433.
Roberts, M.M. et al., "Three-Dimensional Structure of the Adenovirus Major Coat Protein Hexon", Science, 1986, vol. 232, No. 4754, pp. 1148-1151.
Robinson, D. A. et al., "Multilocus sequence typing and the evolution of methicillin-resistant Staphylococcus aureus," Clin. Microbiol. Infect. (2004) 10:92-97.
Rong et al., "Design and Application of 60mer oligonucleotide microarray in Sars coronavirus detection", Chinese Sci. Bull., 2003, 48, 1165-1169.
Ruan et al., Comparative full-length genome sequence analysis of 14 SARS coronavirus isolates and common mutations associated with the putative origins of infection, Lancet (2003) 361:1832.
Rota et al., "Sequencing of a cDNA clone of the nucleoprotein gene of influenza B/Ann Arbor/1/86" Nucleic Acids Research (1989) 17:3595.
Ruest et al., "Comparison of the Directigen Flu A+B test, the QuickVue Influenza Test, and Clinical Case Definition to Viral Culture and Reverse Transcription-PCR for Rapid Diagnosis of Influenza Virus Infection" J. Clin. Microbiol. (2003) 41(8):3487-3493.
Russell, K.L. et al., "Transmission Dynamics and Prospective Environmental Sampling of Adenovirus in a Military Recruit Setting", J. Infect. Dis., 2006, vol. 194, No. 7, pp. 877-885.
Sabat, a. et al., "Comparison of PCR-Based Methods for Typing Staphylococcus aureus Isolates," J. Clin. Microbiol. (2006) 44(10):3804-3807.
Sackesen, C. et al., "Use of polymerase chain reaction for detection of adenovirus in children with or without wheezing", Turk. J. Pediatr., 2005, vol. 47, No. 3, pp. 227-231.
Sakai, H. et al., "Simultaneous Detection of Staphylococcus aureus and Coagulase-Negative Staphylococci in Positive Blood Cultures by Real-Time PCR with Two Fluorescence Resonance Energy Transfer Probe Sets," J. Clin. Microbiol. (2004) 42(12):5739-5744.
Sambrook Et Al., Molecular Cloning: A Laboratory Manual, 2nd Edition, Cold Spring Harbor Press, Cold Spring Harbor, NY 1989.
Sampath et al., "Rapid Identification of Emerging Pathogens: Coronavirus" Emerg. Infect. Dis. (2005) 11(3):373-379.
Sanchez et al., "Detection and Molecular Characterizatio of Ebola viruses causing disease in human and nonhuman primates" the Journal of Infectious Diseases, 179(1):5164-5169 (1999).
Sanchez, J.L. et al., "Epidemic of Adenovirus-Induced Respiratory Illness Among US Military Recruits: Epidemiologic and Immunologic Risk Factors in Healthy, Young adults", J. Med. Virol., 2001, vol. 65, No. 4, pp. 710-718.
Sanchez-Seco, M. P. et al., "A generic nested-RT-PCR followed by sequencing for detection and identification of members of the alphavirus genus," *J. Virol. Methods* (2001) 95(1-2): 153-161.
Santos et al. "Identification and phylogenetic sorting of bacterial lineages with universally conserved genes and proteins" Environmental Microbiology 6(7):754-759, Jul. 2004.
Sarantis, H. et al., "Comprehensive Detection and Serotyping of Human Adenoviruses by PCR and Sequencing", J. Clin. Microbial., 2004, vol. 42, No. 9, pp. 3963-3969.
Scheffner, M. et al., "The E6 Oncoprotein Encoded by Human Papillomavirus Types 16 and 18 Promotes the Degradation of p53," Cell (1990) 63:1129-1136.
Scheuermann et al. "Polymerase chain-reaction-based mRNA quantification Using an internal standard: analysis of oncogene expression" (1993) 218:446-473.
Schlecht, N. F. et al., "Viral Load as a Predictor of the Risk of Cervical Intraepithelial Neoplasia," Int. J. Cancer (2003) 103:519-524.
Schmidt et al., "Analysis of a marine pikoplankton community by 16s rRNA gene cloning and sequencing," J. Bacteriol. (1991) 173:4371-4378.
Schmitz, F. J. et al., "Specific information concerning taxonomy, pathogenicity and methicillin resistance of staphylococci obtained by a multiplex Pcr." J. Med. Microbiol. (1997) 46:773-778.
Schmitz, F. J. et al., "Development of a multiplex-PCR for direct detection of the genes for enterotoxin B and C, and toxic shock syndrome toxin-1 in Staphylococcus aureus isolates," J. Med. Microbiol. (1998) 47(4):335-340.
Schmitz, F. J. et al., "Development of Resistance to Ciprofloxacin, Rifampin, and Mupirocin in Methicillin-Susceptible and -Resistant Staphylococcus aureus Isolates," Antimicrob. Agents Chemother. (2000) 44(11): 3229-3231.
Schwartz, M, et al., "Prenatal diagnosis of alphal-antitrypsin deficiency using polymerase chain reaction (PCR). Comparison of conventional RFLP methods with PCR used in combination with allele specific oligonucleotides or Rflp analysis," 36 CLIN. GENET. 419-426 (1989) (787 reexamination).
Schweiger et al., "Application of a Fluorogenic Pcr Assay for Typing and Subtyping of Influenza Viruses in Respiratory Samples" J. Clin. Microbiol. (2000) 38(4):1552-1558.
Sciacchitano et al., "Analysis of polymerase chain reaction-amplified DNA fragments of clostridium botulinum type E neurotoxin gene by high performance capillary electrophoresis.". *Liq. Chromatogr. Relat. Technol.* (1996) 19:2165-2178.
Scott-Taylor, T.H. et al., "Conserved Sequences of the Adenovirus Genome for Detection of all Human Adenovirus Types by Hybridization", J. Clin. Microbiol., 1992, vol. 30, No. 7, pp. 1703-1710.
Seifarth, et al., "Rapid identification of all known retroviral reverse transcriptase sequences with a novel versatile detection assay," AIDS Res. Human Retrovir. (2000) 16:721-729.
Sellner, L. N. et al., "Sensitive detection of Ross River virus - a one-tube nested RT-PCR," *J. Virol. Methods* (1994) 49(1): 47-58.
Sellner, L., "A Single-Tube Nested RT-PCR for the Detection of Ross River Virus," *Methods Mol. Biol*. (1998) 92: 145-152.
Shadan, F. F. et al., "n-Butyrate, a Cell Cycle Blocker, Inhibits the Replication of Polyomaviruses and Papillomaviruses but Not That of Adenoviruses and Herpesviruses," J. Virol. (1994) 68(8):4785-4796.
Shi et al., "Design and application of 60mer oligonucleotide microarray in SARS coronavirus detection" Chinese Sci. Bull. (2003) 48:1165-1169.
Shimaoka, M. et al., "Development of Enzyme-Labeled Oligonucleotide Probe for Detection of mecA gene in Methicillin-Resistant Staphylococcus aureus," J. Clin. Microbiol (1994) 32(8): 1866-1869.
Shimaoka, M. et al., "Detection of the gene for toxic shock syndrome toxin 1 in Siaphylococcus aureus by enzyme-labelled oligonucleotideprobes," J. Med. Microbiol. (1996) 44:215-218.
Shrestha, N. K. et al., "Rapid Identification of Staphylococcus aureus and the mecA Gene from BacT/Alert Blood Culture Bottles by Using the Lightcycler System," J. Clin. Microbiol. (2002) 40(1):2659-2661.
Simonsen et al., "The Impact of Influenza Epidemics on Hospitalizations" J. Infect. Dis. (2000) 181:831-837.
Skov, R L. et al., "Evaluation of a new 3-h hybridization method for detecting the mecA gene in Staphylococcus aureus and comparison with existing genotypic and phenotypic susceptibility testing methods," J. Antimicrob. Chemother. (1999) 43: 467-475.
Smirnov et al. "Application of Dna-binding polymers for preparation of DNA for analysis by matrix-assisted laser desorption/ionization mass spectrometry." Rapid Comm in Mass Spectrometry (2001) 15:1427-1432.
Smith and Waterman, Adv. Appl. Math., 1981, 2,482-489.
Song et al., "Identification of cry11-type genes from Bacilus thuringiensis strains and characterization of a novel cry11-type gene" App. Environ. Microbiol. (2003) 69:5207-5211.
Spackman et al., "Development of a real-time reverse transcriptase PCR assay for type a influenza virus and the avian H5 and H7 hemagglutinin subtypes" Journal of Clinical Microbiology (2002) 40:3256-3260.

Spiess, et al., "Trehalose is a potent PCR enhancer: Lowering of DNA melting temperature and thermal stabilization of Taq polymerase by the disaccharide trehalose", In: Clinical Chemistry, 2004, 50(7):1256-1259.
Stephensen CB et al., "Phylogenetic analysis of a highly conserved region of the polymerase gene from 11 coronaviruses and development of a consensus polymerase chain reaction assay" Virus Research Amsterdam Nl, 60(2):181-189 (Apr. 1, 1999).
Stone et al., "Rapid detection and simultaneous subtype differentiation of influenza a viruses by real time Pcr" (2004) *Journal of Virological Methods* (2004) 117:103-112.
Stratagene, 1988 Catalog, p. 39.
Strommenger, B. et al., "Multiplex Pcr Assay for Simultaneous Detection of Nine Clinically Relevant Antibiotic Resistance Genes in Staphylococcus aureus," J. Clin. Microbial. (2003) 41(9):4089-4094.
Studdert, M. J. et al., "Polymerase chain reaction tests for the identification of Ross River, Kunjin and Murray Valley encephalitis virus infections in horses," *Aust. Vet. J.* (2003) 81(1-2): 76-80.
Stuhlmeier, R et al., "Fast, simultaneous, and sensitive detection of staphylococci," J. Clin. Pathol. (2003) 56:782-785.
Sundsfjord, a. et al., "Genetic methods for detection of antimicrobial resistance," APMIS (2004) 112:815-837.
Swanborg, R.N., "Human herpesvirus 6 and Chlamydia pneumoniae as etiologic agents in multiple sclerosis—a critical review"Microbes and Infection, 4:1327-1333 (2002).
Swaminathan, B., et al., Emerging Infectious Diseases, 2001, 7, 382-389.
Swenson, J. M. et al., "Perfomance of Eight Methods, Including Two New Rapid Methods, for Detection of Oxacillin Resistance in a Challenge Set of Staphylococcus aureus Organisms," J. Clin. Microbial. (2001) 39(10):3785-3788.
Takagaki, Y. et at., "Four factors are required for 3'-end cleavage of pre-mRNAs," Genes Dev. (1989) 3:1711-1724.
Takahata M, et al., "Mutations in the gyrA and gr1A genes of quinolone-resistant clinical isolates of methicillin-resistant Staphylococcus aureus," the Journal of Antimicrobial Chemotherapy, 38(3):543- 546 (Sep. 1996).
Takayama, R. et al., "Quantification of Adenovirus Species B and C Viremia by Real-Time PCR in Adults and Children Undergoing Stem Cell Transplantation", J. Med. Virol., 2007, vol. 79, No. 3, pp. 278-284.
Talaat et al., "Genome-directed primers for selective labeling of bacterial transcripts for DNA microarray analysis" *Nature Biotechnology* 17:676-682.
Tan, T. Y., "Use of molecular techniques for the detection of antibiotic resistance in bacteria," Expert. Rev. Mol. Diagn. (2003) 3(1):93-103.
Tanabe, F. et al., "The Properties and mec a Gene of the Methicillin-Resistant Staphylccoccus aureus Isolated in Fukushima Medical College Hospital," Fukushima J. Med. Sci (1993) 39(1):35-42.
Tang, K., "Matrix-Assisted Laser Desorption/lonization Mass Spectrometry of Oligonucleotides,".
Tang, K, Nj. Taranenko, S.L. Allman, L.Y. Chang and C.H. Chen, "Double-Stranded DNA Analysis by Matrix Assisted Laser Desorption/lonization," 42nd ASMS Conference on Mass Spectrometry (Jun. 1994) (787 reexamination).
Tang, K, Nj. Taranenko, S.L. Allman, L.Y. Chang and C.H. Chen, "Detection of 500-Nucleotide DNA by Laser Desorption Mass Spectrometry," Rapid Commun. Mass Spectrom. (Sep. 1994) 8: 727-730.
Tarassishin, L. et al., "Adenovirus core protein VII displays a linear epitope conserved in a range of human adenoviruses", J. Gen. Virol., 1999, vol. 80, pp. 47-50.
Tarassishin, L. et al "An epitope on the adenovirus fibre tail is common to all human subgroups", Ach. Virol., 2000, Vol. 145, pp. 805-811.
Taubenberger et al., "Characterization of the 1918 influenza virus polymerase genes" Nature (2005) 437:889-893.
Taylor, L.H., et al., Philos. Trans. R. Soc. Lond B. Biol. Sci. 2001, 356, 983-989.
Tenover, F. C. et al., "Characterization of a Strain of Community-Associated Methicillin-Resistant Slaphylococcus aureus Widely Disseminated in the United States," J. Clin.Microbiol. (2006) 44(1):108- 118.
Teramura, T. et al., "Quantitative detection of serum adenovirus in a transplant recipient", Lancet, 2002, vol. 359, pp. 1945.
Thiel, et al., "Infectious Rna transcribed in vitro from a cDNA copy of the human coronavirus genome cloned in vaccinia virus" J. Gen. Virology 2001 82:1273-1281.
Thompson et al., "Influenza-Associated Hospitalizations in the United States" JAMA (2004) 292:1333-1340.
Thompson et al., "Clustal W: Improving the sensitivity of progressive multiple sequence alignment through sequence weighting, position-specific gap penalties and weight matrix choice" Nucleic Acid Res. (1994) 22:4673-80.
Tokue, Y. et al., "Comparison of a Polymerase Chain Reaction Assay and a Conventional Microbiologic Method for Detection of Methicillin-Resistant Slaphylococcus aureus," Antimicrob. Agents Chemother. (1992) 36(1):6-9.
Top, F., Jr., "Control of Adenovirus Acute Respiratory Disease in U.S. Army Trainees", Yale J. Biol. Med., 1975, vol. 48, pp. 185-195.
Towner, K. J. et al., "Development and evaluation of a PCR-based immunoassay for the rapid detection of methicillin-resistant Staphylococcus aureus," J. Med. Microbial. (1998) 47:607-613.
Tsuneyoshi et al., "Mass spectrometric gene diagnosis of one-base substitution from polymerase chain reaction amplified human DNA" (1997) 11:719-722.
Tsunoda et al., Time and Memory Efficient Algorithm for Extracting Palindromic and Repetitive Subsequences in Nucleic Acid Sequences" Pacific Symposium on Biocomputing (1999) 4:202-213.
Udo, E. E. et al., "Rapid detection of methicillin resistance in staphylococci using a slide latex agglutination kit," Int. J Antimicrob. Agents. (2000) 15(1):19-24.
Udo, E. E. et al., "Genetic analysis of methicillin-resistant Staphylococcus aureus expressing high-and low-level mupirocin resistance."J. Med. Microbiol. (2001) 50:909-515.
Udo, E. E. et al., "A chromosomal location of the mupA gene in Staphylococcus aureus expressing high-level mupirocin resistance," J. Antimicrob. Chemother. (2003) 51:1283-1286.
Unal et al., "Detection of Methicillin-Resistant Staphylococci by Using the Polymerase Chain Reaction" J. Clin. Microbiol. (1992) 30:1685-1691.
Unpublished U.S. Appl. No. 10/323,186 filed Dec. 18, 2002.
Unpublished U.S. Appl. No. 10/323,187 filed Dec. 18, 2002.
Unpublished U.S. Appl. No. 10/324,721 filed Dec. 18, 2002.
Unpublished U.S. Appl. No. 10/728,486 filed Dec. 5, 2003.
Unpublished U.S. Appl. No. 11/209,439 filed Aug. 23, 2005.
Unpublished U.S. Appl. No. 11/682,259 filed Mar. 5, 2007.
Unpublished U.S. Appl. No. 60/604,329 filed Aug. 24, 2004.
Unpublished U.S. Appl. No. 60/632,862 filed Dec. 3, 2004.
Unpublished U.S. Appl. No. 60/639,068 filed Dec. 22, 2004.
Unpublished U.S. Appl. No. 60/648,188 filed Jan. 28, 2005.
Unpublished U.S. Appl. No. 60/658,248 filed Mar. 3, 2005.
Unpublished U.S. Appl. No. 90/010,209 filed Jun. 27, 2008.
Unpublished U.S. Appl. No. 90/010210 filed Jun. 27, 2008.
Upton, A. et al., "Mupirocin and Staphylococcus aureus: a recent paradigm of emerging antibiotic resistance," J. Antimicrob. Chemother. (2003) 51: 613-617.
Vabret, A., et al., "Development of a PCR-and hybridization-based assay (Pcr Adenovirus Consensusa) for the detection and the species identification of adenoviruses in respiratory specimens", J. Clin. Virol., 2004, vol. 31, No. 2, pp. 116-122.
Vanchiere et al. "Detection of BK virus and Simian virus 40 in the urine of healthy children" Journal of Medical Virology (2005) 75:447-454.
Van Der Zee, et al., "Rapid and alternative screening methods for microbiological analysis" J. AOAC Int., 1997, 80, 934-940.
Van Dinten et al., "Proteolytic Processing of the Open Reading Frame 1b-Encoded Part of Arterivirus Replicase Is Mediated by nsp4 Serine Protease and Is Essential for Virus Replication" J. Virology, 1999, vol. 73, pp. 2027-2037.
Van Elden et al., "Simultaneous Detection of Influenza Viruses A and B Using Real-Time Quantitative PCR" J. Clin. Microbiol. (2001) 39(1):196-200.
Van Elden et al., "Clinical diagnosis of influenza virus infection: evaluation of diagnostic tools in general practice" Br. J. Gen. Pract. (2001) 51:630-634.

Van Leeuwen, W. B. et al., "Rapid Detection of Methicillin-Resistance in Staphylococus aureus Isolates by the MRSA-Screen Latex Agglutination Test,"J. Clin. Microbiol. (1999) 37(9):3029-3030.

Van Leeuwen, W. B. et al., "Multilocus Sequence Typing of Staphylococcus aureus with DNA Array Technology," J. Clin. Microbiol. (2003) 41(7):3323-3326.

Vannuffel, P. et al.. "Specific Detection of Methicillin-Resistant Staphylococcus Species by Multiplex PCR," J. Clin Microbiol. (1995) 33(11):2864-2867.

Vannuffel, P. et al., "Rapid and Specific Molecular Identification of Methicillin-Resistant Staphylococcus aureus in Endotracheal Aspirates from Mechanically Ventilated Patients," J Clin. Microbiol. (1998) 36(8):2366-2368.

Videla, C. et al., "Genomic analysis of adenovirus isolated from Argentinean children with acute lower respiratory infections", J. Clin. Virol., 1999, vol. 14, pp. 67-71.

Vilchez, Regis a et al., "Detection of polyomavirus simian virus 40 tumor antigen DNA in Aids related systemic non-Hodgkin lymphoma," J. Aids Journal of Acquired Immune Deficiency Syndromes, 29(2):109-116 (Feb. 1, 2002).

Voelter C et al., "Screening human tumor samples with a broad-spectrum polymerase chain reaction method for the detection of polyomaviruses", VIROLOGY, Academic Press, Orlando, US 237(2):389-396 (Oct. 1997).

Volokhov et al. Microarray analysis of erythromycin resistance determinants. Journal of Applied Microbiology 95:787-798 (2003).

Von Eiff, C. et al., "Pathogenesis of infections due to coagulase-negative staphylococci," Lancet Infect. Dis. (2002) 2:677-685.

Walker, E. S. et al., "A Decline in Mupimcin Resistance in Methicillin-Resistant Staphylococcus aureus Accompanied Administrative Control of Prescriptions," J. Clin. Microbiol. (2004) 42(6):2792-2795.

Wallace, et al., "The Enigma of Endonuclease VII. DNA Repair," 2:441-453 (2003).

Wallet, F. et al., "Choice of a routine method for detecting methicillin-resistance in staphylococci,"I Antimicrob. Chemother. (1996) 37:901-909.

Wang, G. et al., "Targeted Mutagenesis in Mammalian Cells Mediated by Intracellular Triple Helix Formation," Mol. Cell. Biol. (1995) 15(3):1759-1768.

Ward et al., "Design and performance testing of quantitative real time PCR assays for influenza a and B viral load measurement" *Journal of Clinical Virology* (2004) 29:179-188.

Weissenbacher, M. et al., "Etiologic and Clinical Evaluation of Acute Lower Respiratory Tract Infections in Young Argentinean Children: An Overview", Rev. Infect. Dis., 1990, vol. 12, Suppl. 8; pp. S889-898.

Wertheim, H. F. et al., "Effect of Mupirocin Treatment on Nasal, Pharyngeal, and Perinea Carriage of Staphylococcus aureus in Healthy Adults," Antimicrob. Agents Chemother. (2005) 49(4):1465-1467.

Westermann, P. et al., "Inhibition of expression of SV40 virus large T-antigen by antisense oligodeoxyribonucleotides," Biomed. Biochim. Acta (1989) 1:85-93.

Whiley, David M et al., "Simultaneous detection and differentiation of human polyomaviruses JC and BK by a rapid and sensitive PCR-ELAHA assay and a survey of the Jcv subtypes within an Australian population," Journal of Medical Virology, 72(3):467-472 (Mar. 2004).

Wichelhaus, T. A. et al., "Rapid Detection of Epidemic Strains of Methicillin-Resistant Staphylococcus aureus," J. Clin. Microbiol. (1999) 37(3):690-693.

Wickham, T.J., "Targeting adenovirus", Gene Therapy, 2000, vol. 7, pp. 110-114.

Widjojoatmodjo et al. "The magnetic Immuno polymerase chain reaction assay for direct detection of Salmonellae in fecal samples" J. Clin. Microbiol. (1992) 30(12):3195-3199.

Winger et al., "High resolution accurate mass measurements of biomolecules using a new electrospray ionization ion cyclotron resonance mass spectrometer" J. Am. Soc. Mass Spectrom. 4, 566, 1993.

Wintzingerode et al. "Base-specific fragmentation of amplified 16s rRNA genes analyzed by mass spectrometry: A tool for rapid bacterial identification" PNAS 99(10):7039-7044, 2002.

Wood, S.R. et al., "Rapid Detection and Serotyping of Adenovirus by Direct Immunofluorescence", J. Med. Virol., 1997, vol. 51, No. 3, pp. 198-201.

Wright et al., "Typing and Subtyping of Influenza Viruses in Clinical Samples by PCR" J. Clin. Microbiol. (1995) 33(5):1180-1184.

Wu et al., "Genetic Organization of the mecA Region in Methicillin-Susceptible and Methicillin-Resistant Strains of Staphylococcus sciuri" J. Bacteriol. (1998) 180(2):236-242.

Wu et al., "Establishment of a fluorescent polymerase chain reaction method for the detection of Sars-associated coronavirus and its clinical application" Chin. Med. J. (2003) 116:988-990.

Xu et al. "Electrospray mass tag dideoxy DNA sequencing" Anal. Chem. (1997) 69:3595-3602.

Xu et al., "Intercontinental Circulation of Human Influenza a(H1N2) Reassortant Viruses During the 2001-2002 Influenza Season" J. Infect. Dis. (2002):186:1490-1493.

Xu, W. et al., "Species-Specific Identification of Human Adenoviruses by a Multiplex PCR Assay", J. Clin. Microbiol., 2000, vol. 38, No. 11, pp. 4114-4120.

Xu, W. et al., "Type-Specific Identification of Human Adenovirus, 3, 7, and 21 by a Multiplex PCR Assay", J. Med. Virol., 2001, vol. 64, No. 4, pp. 537-542.

Ye, K. et al., "Three Distinct Promoters Direct Transcription of Different 5' Untranslated Regions of the Human Interleukin 1 Type I Receptor: a Possible Mechanism for Control of Translation," Cytokine (1996) 8(6):421-429.

Yun, H J et al., "Increased antibacterial activity of OW286, a novel fluoronaphthyridone antibiotic, against Staphylococcus aureus strains with defined mutations in DNA gyrase and toposiomerase IV", International Journal of Antimicrobial Agents, Amsterdam, NL, 25(4):334-337 (Apr. 1, 2005).

Zhang et al., "Detectiona and identification of human influenza viruses by the polymerase chain reaction" J. Virol. Methods (1991) 33(1-2):165-189.

Zhang, K. et al., "New Quadriplex PCR Assay for Detection of Methicillin and Mupirocin Resistance and Simultaneous Discrimination of Staphylococcus aureus from Coagulase-Negative Staphylococci," J. Clin. Microbiol. (2004) 42(11):4947-4955.

Zhang, Y.-Q. et al., "Genome-based analysis of virulence genes in a non-biofilm-forming.

* cited by examiner

METHODS FOR CONCURRENT IDENTIFICATION AND QUANTIFICATION OF AN UNKNOWN BIOAGENT

CROSS-REFERENCE TO RELATED APPLICATIONS

This application claims the benefit of priority to U.S. Provisional Application Ser. No. 60/545,425 filed Feb. 18, 2004, and U.S. Provisional Application Ser. No. 60/559,754 filed Apr. 5, 2004, each of which is incorporated herein by reference in its entirety.

STATEMENT OF GOVERNMENT SUPPORT

This invention was made with United States Government support under DARPA contract MDA972-00-C-0053. The United States Government has certain rights in the invention.

FIELD OF THE INVENTION

The present invention is related generally to nucleic acid amplification technology and microbiology.

BACKGROUND OF THE INVENTION

Information about the identity and total amount of microbes in biological samples is of prime importance in medicine in order to assess the risk of infectious disease, to diagnose infections and predict their clinical course. In a variety of other areas such as food product monitoring, bioremediation, microbial forensics and biowarfare/bioterror investigations, efficient and cost effective methods for quantification of microbial bioagents are needed. In addition, determination of the quantity of a bioagent (microbe, bacterium, virus, fungus, etc.) is a common endeavor in microbiology in the fields of clinical diagnostics, epidemiology, forensics, bioremediation, and quality control.

Methods currently in use for detection and determination of bacteria include bacterial culture and microscopy, detection of bacterial metabolites, and identification of surface molecules by specific antibodies.

The polymerase chain reaction (PCR) is only a qualitative method due to its exponential time course and equally exponential amplification of errors. Efforts have been made to convert PCR to a quantitative method. Among the variety of quantitative PCR methods, are methods depending upon external standardization and on internal standardization. Among the latter, competitive PCR methods are based on co-amplification of a target DNA with a standard competitor DNA which competes with the template DNA for the same set of amplification primers. Since the competitor is added to the PCR reaction mixture in known amounts, it is possible to calculate the amount of target DNA from the experimental determination of the ratio of amplified products of sample and standard competitor DNA.

Methods for rapid and cost effective identification of microbial bioagents through molecular mass measurement of amplification products by molecular mass analysis of bioagent identifying amplicons are disclosed and claimed in U.S. application Ser. Nos. 09/798,007, 09/891,793, 10/660,997, 10/660,122, 10/660,996, 10/418,514 and 10/728,486, each of which is commonly owned and incorporated herein by reference in its entirety. These methods and others would derive great benefit from a means of determination of the quantity of any given microbial bioagent present in a biological sample. Quantification of organisms can be very valuable, particularly in a clinical setting, like Hepatitis C for example, where the greater the number of infectious organisms generally correlates with a less healthy patient and a more difficult clinical course.

The methods described herein satisfy the need for methods for concurrent identification and quantification of bioagents, as well as other needs, by providing internal calibration using a nucleic acid standard calibrant in an amplification reaction.

SUMMARY OF THE INVENTION

The present invention provides methods for determination of the quantity of an unknown bioagent in a sample by contacting the sample with a pair of primers and a known quantity of a calibration polynucleotide that comprises a calibration sequence. Nucleic acid from the bioagent in the sample is concurrently amplified with the pair of primers and amplifying nucleic acid from the calibration polynucleotide in the sample with the pair of primers to obtain a first amplification product comprising a bioagent identifying amplicon and a second amplification product comprising a calibration amplicon. The sample is then subjected to molecular mass analysis resulting in molecular mass and abundance data for the bioagent identifying amplicon and the calibration amplicon. The bioagent identifying amplicon is distinguished from the calibration amplicon based on molecular mass wherein the molecular mass of the bioagent identifying amplicon provides a means for identifying the bioagent. Comparison of bioagent identifying amplicon abundance data and calibration amplicon abundance data indicates the quantity of bioagent in the sample.

The figures depict preferred embodiments of the present invention for purposes of illustration only. One skilled in the art will readily recognize from the following discussion that alternative embodiments of the structures and methods illustrated herein may be employed without departing from the principles of the invention described herein.

DESCRIPTION OF EMBODIMENTS

Figure 1:
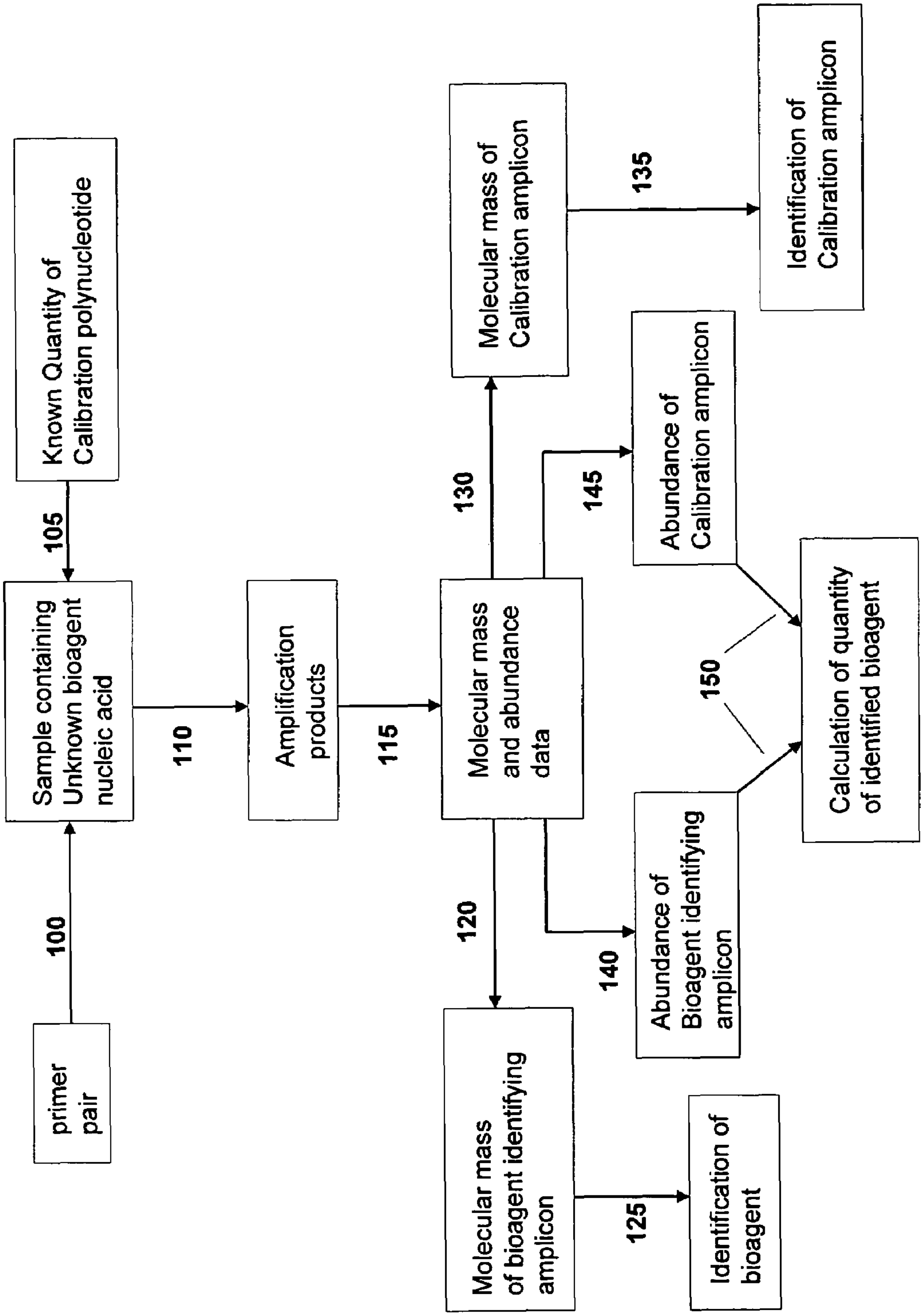
FIG. 1 shows a representative process diagram for identification and determination of the quantity of a bioagent in a sample.

The present invention provides methods for identification and determination of the quantity of a bioagent in a sample. Referring to FIG. 1, to a sample containing nucleic acid of an unknown bioagent are added primers (100) and a known quantity of a calibration polynucleotide (105). The total nucleic acid in the sample is then subjected to an amplification reaction (110) to obtain amplification products. The molecular masses of amplification products are determined (115) from which are obtained molecular mass and abundance data. The molecular mass of the bioagent identifying amplicon (120) provides the means for its identification (125)

and the molecular mass of the calibration amplicon obtained from the calibration polynucleotide (130) provides the means for its identification (135). The abundance data of the bioagent identifying amplicon is recorded (140) and the abundance data for the calibration data is recorded (145), both of which are used in a calculation (150) which determines the quantity of unknown bioagent in the sample. Each of these features is described below in greater detail.

In one embodiment, a sample comprising an unknown bioagent is contacted with a pair of primers which can amplify nucleic acid from the bioagent, and a known quantity of a polynucleotide that comprises a calibration sequence. The nucleic acids of the bioagent and of the calibration sequence are amplified. The rate of amplification is reasonably assumed to be similar for the nucleic acid of the bioagent and of the calibration sequence. The amplification reaction produces two amplification products: a bioagent identifying amplicon and a calibration amplicon. The amplified sample containing the bioagent identifying amplicon and the calibration amplicon is then subjected to molecular mass analysis by mass spectrometry, for example. The resulting molecular mass analysis of the nucleic acid of the bioagent and of the calibration sequence provides molecular mass data and abundance data for the nucleic acid of the bioagent and of the calibration sequence. The molecular mass data obtained for the nucleic acid of the bioagent enables identification of the unknown bioagent and the abundance data enables calculation of the quantity of the bioagent, based on the knowledge of the quantity of calibration polynucleotide contacted with the sample. The calculations are well within the scope of those of the ordinary artisan.

A calibration sequence is a sequence chosen to represent a portion of a genome of a bioagent (bacterium, virus etc.) that can be amplified by a particular primer pair to yield an amplification product (calibration amplicon) that can be distinguished on the basis of its molecular mass from an analogous amplification product (bioagent identifying amplicon) obtained by amplification of native DNA of a bioagent (bacterium, virus, etc) with the same pair of primers. One means of distinguishing an amplification product of a calibration sequence vs. a bioagent identifying amplicon is to design the calibration sequence so that, upon amplification, it gives rise to an amplification product consisting of a calibration amplicon that has a molecular mass distinguishable from the analogous bioagent identifying amplicon. This is desired because, as in any internally calibrated method, the calibration sequence and the bioagent sequence are amplified concurrently in the same amplification reaction vessel.

In some embodiments, construction of a standard curve where the amount of calibration polynucleotide spiked into the sample is varied, provides additional resolution and improved confidence for the determination of the quantity of bioagent in the sample. The use of standard curves for analytical determination of molecular quantities is well known to one with ordinary skill and can be performed without undue experimentation.

In some embodiments, multiplex amplification is performed where multiple bioagent identifying amplicons are amplified with multiple intelligent primer pairs which also amplify the corresponding standard calibration sequences. In this or other embodiments, the standard calibration sequences are optionally included within a single vector such as a plasmid which functions as the calibration polynucleotide. Multiplex amplification methods are well known to those with ordinary skill and can be performed without undue experimentation.

In some embodiments, the calibrant polynucleotide is used as an internal positive control to confirm that amplification conditions and subsequent analysis steps are successful in producing a measurable amplicon. Even in the absence of copies of the genome of a bioagent, the calibration polynucleotide can give rise to a calibration amplicon. Failure to produce a measurable calibration amplicon indicates a failure of amplification or subsequent analysis step such as amplicon purification or molecular mass determination.

In some embodiments, the calibration sequence is inserted into a vector which then itself functions as the calibration polynucleotide. In some embodiments, more than one calibration sequence is inserted into the vector that functions as the calibration polynucleotide. The process of inserting polynucleotides into vectors is routine to those skilled in the art and can be accomplished without undue experimentation. Thus, it should be recognized that the present invention should not be limited to the embodiments described herein. The present invention can be applied for determination of the quantity of any bioagent identifying amplicon when an appropriate standard calibrant polynucleotide sequence is designed and used. The process of choosing an appropriate vector such as a plasmid for insertion of a calibrant is also a routine operation that can be accomplished by one with ordinary skill without undue experimentation.

In some embodiments of the present invention, determination of the molecular masses of the bioagent identifying amplicon and the calibration amplicon is accomplished using mass spectrometry. Exemplary techniques of mass spectrometry include, but are not limited to, electrospray ionization Fourier transform ion cyclotron resonance mass spectrometry (ESI-FTICR-MS) and electrospray ionization time-of-flight mass spectrometry (ESI-TOF-MS).

In some embodiments, bioagent identifying amplicons and calibration amplicons are of a length between about 45-200 base pairs. One will recognize that these embodiments comprise bioagent identifying amplicons and calibration amplicons of lengths of about 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 base pairs, or any range therewithin.

In other embodiments, bioagent identifying amplicons and calibration amplicons are of a length between about 45-140 base pairs. One will recognize that these embodiments comprise bioagent identifying amplicons and calibration amplicons of lengths of about 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, or 140 base pairs, or any range therewithin.

In some embodiments, the primers used to obtain bioagent identifying amplicons and calibration amplicons upon amplification hybridize to conserved regions of nucleic acid of genes encoding proteins or RNAs necessary for life which include, but are not limited to: 16S and 23S rRNAs, RNA polymerase subunits, t-RNA synthetases, elongation factors, ribosomal proteins, protein chain initiation factors, cell division proteins, chaperonin groEL, chaperonin dnaK, phosphoglycerate kinase, NADH dehydrogenase, DNA ligases, and DNA topoisomerases.

Calibration sequences can be routinely designed without undue experimentation by choosing a reference sequence representing any bioagent identifying amplicon that can be amplified by a specific pair of primers of any class e.g: broad range survey, division-wide, clade level, or drill down or any arbitrarily named class of primer and by deleting or inserting about 2-8 consecutive nucleobases into that sequence such that the calibration sequence is distinguishable by molecular mass from the reference sequence upon which the calibration sequence is based. One will recognize that this range comprises insertions or deletions of 2, 3, 4, 5, 6, 7, or 8 nucleobases. In other embodiments, the total insertion or deletion of consecutive nucleobases may also exceed 8 nucleobases. In other embodiments, the total insertion or deletion of consecutive nucleobases results in a calibration sequence having at least 80%, at least 85%, at least 90%, or at least 95% sequence identity with a chosen standard sequence of a bioagent identifying amplicon.

In some embodiments, the primers used for amplification of bioagent identifying amplicons and calibration amplicons hybridize to and amplify genomic DNA, DNA of bacterial plasmids or DNA of DNA viruses.

In some embodiments, the primers used for amplification of bioagent identifying amplicons and corresponding calibration amplicons hybridize directly to ribosomal RNA or messenger RNA (mRNA) and act as reverse transcription primers for obtaining DNA from direct amplification of bacterial rRNA. Methods of amplifying RNA using reverse transcriptase are well known to those with ordinary skill in the art and can be routinely established without undue experimentation.

Synthesis of primers is well known and routine in the art. The primers may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

The primers can be employed as compositions for use in methods for identification of bacterial bioagents as follows: a primer pair composition is contacted with nucleic acid of an unknown bacterial bioagent. The nucleic acid is then amplified by a nucleic acid amplification technique, such as PCR for example, to obtain an amplification product that represents a bioagent identifying amplicon. The molecular mass of a single strand or each strand of the double-stranded amplification product is determined by a molecular mass measurement technique such as mass spectrometry for example, wherein the two strands of the double-stranded amplification product are separated during the ionization process. In some embodiments, the mass spectrometry is electrospray Fourier transform ion cyclotron resonance mass spectrometry (ESI-FTICR-MS) or electrospray time of flight mass spectrometry (ESI-TOF-MS). A list of possible base compositions can be generated for the molecular mass value obtained for each strand and the choice of the correct base composition from the list is facilitated by matching the base composition of one strand with a complementary base composition of the other strand. The molecular mass or base composition thus determined is then compared with a database of molecular masses or base compositions of analogous bioagent identifying amplicons for known bioagents. A match between the molecular mass or base composition of the amplification product and the molecular mass or base composition of an analogous bioagent identifying amplicon for a known bioagent indicates the identity of the unknown bioagent. In some embodiments, the method is repeated using a different primer pair to resolve possible ambiguities in the identification process or to improve the confidence level for the identification assignment.

In some embodiments, a bioagent identifying amplicon or a calibration amplicon may be produced using only a single primer composition (either the forward or reverse primer of any given primer pair), provided an appropriate amplification method is chosen, such as, for example, low stringency single primer PCR (LSSP-PCR).

In some embodiments, the oligonucleotide primers are "broad range survey primers" which hybridize to conserved regions of nucleic acid encoding ribosomal RNA (rRNA) of at least 50%, at least 60%, at least 70%, at least 80%, at least 90%, at least 99%, or all known bacteria and produce bacterial bioagent identifying amplicons. As used herein, the term "broad range survey primers" refers to primers that bind to nucleic acid encoding rRNAs of at least 50%, at least 60%, at least 70%, at least 80%, at least 90%, at least 99%, or all known species of bacteria. In some embodiments, the rRNAs to which the primers hybridize are 16S and 23S rRNAs.

In some cases, the molecular mass or base composition of a bacterial bioagent identifying amplicon defined by a broad range survey primer pair does not provide enough resolution to unambiguously identify a bacterial bioagent at the species level. These cases benefit from further analysis of one or more bacterial bioagent identifying amplicons generated from at least one additional broad range survey primer pair or from at least one additional "division-wide" primer pair (vide infra). The employment of more than one bioagent identifying amplicon for identification of a bioagent is herein referred to as "triangulation identification" (vide infra).

In other embodiments, the oligonucleotide primers are "division-wide" primers which hybridize to nucleic acid encoding genes of broad divisions of bacteria such as members of the *Bacillus/Clostridia* group or members of the α-, β-, γ-, and ε-proteobacteria. In some embodiments, a division of bacteria comprises any grouping of bacterial genera with more than one genus represented. For example, the β-proteobacteria group comprises members of the following genera: *Eikenella, Neisseria, Achromobacter, Bordetella, Burkholderia*, and *Raltsonia*. Species members of these genera can be identified using bacterial bioagent identifying amplicons generated with a primer pair which produces a bacterial bioagent identifying amplicon from the tufB gene of β-proteobacteria. Examples of genes to which division-wide primers may hybridize to include, but are not limited to: RNA polymerase subunits such as rpoB and rpoC, tRNA synthetases such as valyl-tRNA synthetase (valS) and aspartyl-tRNA synthetase (aspS), elongation factors such as elongation factor EF-Tu (tufB), ribosomal proteins such as ribosomal protein L2 (rplB), protein chain initiation factors such as protein chain initiation factor infB, chaperonins such as groL and dnaK, and cell division proteins such as peptidase ftsH (hflB).

In other embodiments, the oligonucleotide primers are designed to enable the identification of bacteria at the clade group level, which is a monophyletic taxon referring to a group of organisms which includes the most recent common ancestor of at least 70%, at least 80%, at least 90%, or all of its members and at least 70%, at least 80%, at least 90%, or all of the descendants of that most recent common ancestor. The *Bacillus cereus* clade is an example of a bacterial clade group.

In other embodiments, the oligonucleotide primers are "drill-down" primers which enable the identification of "sub-species characteristics." These primers can hybridize to conserved regions of nucleic acid of genes encoding structural proteins or proteins implicated in, for example, pathogenicity. Examples of genes indicating sub-species characteristics include, but are not limited to: toxin genes, pathogenicity markers, antibiotic resistance genes and virulence factors. Drill down primers provide the functionality of producing bacterial bioagent identifying amplicons for drill-down analyses such as strain typing when contacted with bacterial nucleic acid under amplification conditions. Identification of such sub-species characteristics is often critical for determining proper clinical treatment of bacterial infections.

It is, thus, readily apparent that one with ordinary skill can design calibration sequences that can be amplified by any of the primer classes disclosed herein in order to produce appropriate calibration amplicons.

One with ordinary skill in the art of design of amplification primers will recognize that a given primer need not hybridize with 100% complementarity in order to effectively prime the synthesis of a complementary nucleic acid strand in an amplification reaction. Moreover, a primer may hybridize over one or more segments such that intervening or adjacent segments are not involved in the hybridization event. (e.g: a loop structure or a hairpin structure). The primers of the present invention may comprise at least 70%, at least 75%, at least 80%, at least 85%, at least 90%, at least 95% or at least 99% sequence identity with any of the primers listed in Table 1. Thus, in some embodiments of the present invention, an extent of variation of 70% to 100% of the sequence identity is possible relative to the specific primer sequences disclosed herein. Determination of sequence identity is described in the following example: a primer 20 nucleobases in length which is identical to another 20 nucleobase primer having two non-identical residues has 18 of 20 identical residues (18/20=0.9 or 90% sequence identity). In another example, a primer 15 nucleobases in length having all residues identical to a 15 nucleobase segment of primer 20 nucleobases in length would have 15/20=0.75 or 75% sequence identity with the 20 nucleobase primer.

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some embodiments, complementarity of primers with respect to the conserved priming regions of bacterial nucleic acid, is between about 70% and about 80%. In other embodiments, homology, sequence identity or complementarity, is between about 80% and about 90%. In yet other embodiments, homology, sequence identity or complementarity, is about 90%, about 92%, about 94%, about 95%, about 96%, about 97%, about 98%, about 99% or about 100%.

One with ordinary skill is able to calculate percent sequence identity or percent sequence homology and able to determine, without undue experimentation, the effects of variation of primer sequence identity on the function of the primer in its role in priming synthesis of a complementary strand of nucleic acid for production of an amplification product of a corresponding bioagent identifying amplicon.

In some embodiments of the present invention, the oligonucleotide primers are between 13 and 35 nucleobases in length (13 to 35 linked nucleotide residues). These embodiments comprise oligonucleotide primers 13, 14, 15, 16, 17, 18, 19, 20, 21, 22, 23, 24, 25, 26, 27, 28, 29, 30, 31, 32, 33, 34 or 35 nucleobases in length, or any range therewithin.

In some embodiments, any given primer comprises a modification comprising the addition of a non-templated T residue to the 5' end of the primer i.e: the added T residue does not necessarily hybridize to the nucleic acid being amplified. The addition of a non-templated T residue has the effect of minimizing the addition of non-templated A residues as a result of the non-specific enzyme activity of Taq polymerase (Magnuson et al., Biotechniques, 1996, 21, 700-709), an occurrence which may lead to ambiguous results arising from molecular mass analysis.

In some embodiments of the present invention, primers may contain one or more universal bases. Because any variation (due to codon wobble in the 3$^{rd}$ position) in the conserved regions among species is likely to occur in the third position of a DNA triplet, oligonucleotide primers can be designed such that the nucleotide corresponding to this position is a base which can bind to more than one nucleotide, referred to herein as a "universal nucleobase." For example, under this "wobble" pairing, inosine (I) binds to U, C or A; guanine (G) binds to U or C, and uridine (U) binds to U or C. Other examples of universal nucleobases include nitroindoles such as 5-nitroindole or 3-nitropyrrole (Loakes et al., Nucleosides and Nucleotides, 1995, 14, 1001-1003), the degenerate nucleotides dP or dK (Hill et al.), an acyclic nucleoside analog containing 5-nitroindazole (Van Aerschot et al., Nucleosides and Nucleotides, 1995, 14, 1053-1056) or the purine analog 1-(2-deoxy-β-D-ribofuranosyl)-imidazole-4-carboxamide (Sala et al., Nucl. Acids Res., 1996, 24, 3302-3306).

In some embodiments, to compensate for the somewhat weaker binding by the "wobble" base, the oligonucleotide primers are designed such that the first and second positions of each triplet are occupied by nucleotide analogs which bind with greater affinity than the unmodified nucleotide. Examples of these analogs include, but are not limited to, 2,6-diaminopurine which binds to thymine, 5-propynyluracil which binds to adenine and 5-propynylcytosine and phenoxazines, including G-clamp, which binds to G. Propynylated pyrimidines are described in U.S. Pat. Nos. 5,645,985, 5,830,653 and 5,484,908, each of which is commonly owned and incorporated herein by reference in its entirety. Propynylated primers are described in U.S. Ser. No. 10/294,203 which is also commonly owned and incorporated herein by reference in entirety. Phenoxazines are described in U.S. Pat. Nos. 5,502,177, 5,763,588, and 6,005,096, each of which is incorporated herein by reference in its entirety. G-clamps are described in U.S. Pat. Nos. 6,007,992 and 6,028,183, each of which is incorporated herein by reference in its entirety.

In some embodiments, non-template primer tags are used to increase the melting temperature ($T_m$) of a primer-template duplex in order to improve amplification efficiency. A non-template tag is designed to hybridize to at least three consecutive A or T nucleotide residues on a primer which are complementary to the template. In any given non-template tag, A can be replaced by C or G and T can also be replaced by C or G. The extra hydrogen bond in a G-C pair relative to a A-T pair confers increased stability of the primer-template duplex and improves amplification efficiency.

In other embodiments, propynylated tags may be used in a manner similar to that of the non-template tag, wherein two or more 5-propynylcytidine or 5-propynyluridine residues replace template matching residues on a primer. In other embodiments, a primer contains a modified internucleoside linkage such as a phosphorothioate linkage, for example.

In some embodiments, the primers contain mass-modifying tags. Reducing the total number of possible base compositions of a nucleic acid of specific molecular weight provides a means of avoiding a persistent source of ambiguity in determination of base composition of amplification products. Addition of mass-modifying tags to certain nucleobases of a given primer will result in simplification of de novo determination of base composition of a given bioagent identifying amplicon (vide infra) from its molecular mass.

In some embodiments of the present invention, the mass modified nucleobase comprises one of the following: 7-deaza-2'-deoxyadenosine-5-triphosphate, 5-iodo-2'-deoxyuridine-5'-triphosphate, 5-bromo-2'-deoxyuridine-5'-triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, O6-methyl-2'-deoxyguanosine-5'-triphosphate, N2-methyl-2'-deoxyguanosine-5'-triphosphate, 8-oxo-2'-deoxyguanosine-5'-triphosphate or thiothymidine-5'-triphosphate. In some embodiments, the mass-modified nucleobase comprises $^{15}N$ or $^{13}C$ or both $^{15}N$ and $^{13}C$.

In some embodiments, bioagent identifying amplicons amenable to molecular mass determination which are produced by the primers described herein are either of a length, size or mass compatible with the particular mode of molecular mass determination or compatible with a means of providing a predictable fragmentation pattern in order to obtain predictable fragments of a length compatible with the particular mode of molecular mass determination. Such means of providing a predictable fragmentation pattern of an amplification product include, but are not limited to, cleavage with restriction enzymes or cleavage primers, for example. Methods of using restriction enzymes and cleavage primers are well known to those with ordinary skill in the art.

In some embodiments, amplification products corresponding to bacterial bioagent identifying amplicons are obtained using the polymerase chain reaction (PCR) which is a routine method to those with ordinary skill in the molecular biology arts. Other amplification methods may be used such as ligase chain reaction (LCR), low-stringency single primer PCR, and multiple strand displacement amplification (MDA) which are also well known to those with ordinary skill.

In the context of this invention, a "bioagent" is any organism, cell, or virus, living or dead, or a nucleic acid derived from such an organism, cell or virus. Examples of bioagents include, but are not limited, to cells, (including but not limited to human clinical samples, bacterial cells and other pathogens), viruses, fungi, protists, parasites, and pathogenicity markers (including but not limited to: pathogenicity islands, antibiotic resistance genes, virulence factors, toxin genes and other bioregulating compounds). Samples may be alive or dead or in a vegetative state (for example, vegetative bacteria or spores) and may be encapsulated or bioengineered. In the context of this invention, a "pathogen" is a bioagent which causes a disease or disorder.

In the context of this invention, the term "unknown bioagent" may mean either: (i) a bioagent whose existence is known (such as the well known bacterial species *Staphylococcus aureus* for example) but which is not known to be in a sample to be analyzed, or (ii) a bioagent whose existence is not known (for example, the SARS coronavirus was unknown prior to April 2003). For example, if the method for identification of coronaviruses disclosed in commonly owned U.S. Ser. No. 10/829,826 (incorporated herein by reference in entirety) was to be employed prior to April 2003 to identify the SARS coronavirus in a clinical sample, both meanings of "unknown" bioagent are applicable since the SARS coronavirus was unknown to science prior to April, 2003 and since it was not known what bioagent (in this case a coronavirus) was present in the sample. On the other hand, if the method of U.S. Ser. No. 10/829,826 was to be employed subsequent to April 2003 to identify the SARS coronavirus in a clinical sample, only the first meaning (i) of "unknown" bioagent would apply since the SARS coronavirus became known to science subsequent to April 2003 and since it was not known what bioagent was present in the sample.

In those embodiments wherein the bioagent is an RNA virus, the RNA of the virus is reverse transcribed to obtain corresponding DNA which can be subsequently amplified by procedures referred to above. In one embodiment, one means of reverse transcription is reverse transcriptase, an enzyme well known in the molecular biology arts.

The employment of more than one bioagent identifying amplicon for identification of a bioagent is herein referred to as "triangulation identification." Triangulation identification is pursued by analyzing a plurality of bioagent identifying amplicons selected within multiple core genes. This process can be used to reduce false negative and false positive signals, and enable reconstruction of the origin of hybrid or otherwise engineered bioagents. For example, identification of the three part toxin genes typical of *B. anthracis* (Bowen et al., J. Appl. Microbiol., 1999, 87, 270-278) in the absence of the expected signatures from the *B. anthracis* genome would suggest a genetic engineering event.

In some embodiments, the triangulation identification process can be pursued by characterization of bioagent identifying amplicons in a massively parallel fashion using the polymerase chain reaction (PCR), such as multiplex PCR where multiple primers are employed in the same amplification reaction mixture, or PCR in multi-well plate format wherein a different and unique pair of primers is used in multiple wells containing otherwise identical reaction mixtures. Such multiplex and multi-well PCR methods are well known to those with ordinary skill in the arts of rapid throughput amplification of nucleic acids.

In some embodiments, the molecular mass of a given bioagent identifying amplicon is determined by mass spectrometry. Mass spectrometry has several advantages, not the least of which is high bandwidth characterized by the ability to separate (and isolate) many molecular peaks across a broad range of mass to charge ratio (m/z). Thus mass spectrometry is intrinsically a parallel detection scheme without the need for radioactive or fluorescent labels, since every amplification product is identified by its molecular mass. The current state of the art in mass spectrometry is such that less than femtomole quantities of material can be readily analyzed to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons.

In some embodiments, intact molecular ions are generated from amplification products using one of a variety of ionization techniques to convert the sample to gas phase. These ionization methods include, but are not limited to, electrospray ionization (ES), matrix-assisted laser desorption ionization (MALDI) and fast atom bombardment (FAB). Upon ionization, several peaks are observed from one sample due to the formation of ions with different charges. Averaging the multiple readings of molecular mass obtained from a single mass spectrum affords an estimate of molecular mass of the bioagent identifying amplicon. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used in the methods of the present invention include, but are not limited to, Fourier transform ion cyclotron resonance mass spectrometry (FT-ICR-MS), ion trap, quadrupole, magnetic sector, time of flight (TOF), Q-TOF, and triple quadrupole.

In some embodiments, conversion of molecular mass data to a base composition is useful for certain analyses. As used herein, a "base composition" is the exact number of each nucleobase (A, T, C and G). For example, amplification of nucleic acid of *Neisseria meningitidis* with a primer pair that produces an amplification product from nucleic acid of 23S rRNA that has a molecular mass (sense strand) of 28480.75124, from which a base composition of A25 G27 C22 T18 is assigned from a list of possible base compositions calculated from the molecular mass using standard known molecular masses of each of the four nucleobases.

In some embodiments, assignment of base compositions to experimentally determined molecular masses is accomplished using "base composition probability clouds." Base compositions, like sequences, vary slightly from isolate to isolate within species. It is possible to manage this diversity by building "base composition probability clouds" around the composition constraints for each species. This permits identification of organisms in a fashion similar to sequence analysis. Optimal primer design requires optimal choice of bioagent identifying amplicons and maximizes the separation between the base composition signatures of individual bioagents. Areas where clouds overlap indicate regions that may result in a misclassification, a problem which is overcome by a triangulation identification process using bioagent identifying amplicons not affected by overlap of base composition probability clouds.

In some embodiments, base composition probability clouds provide the means for screening potential primer pairs in order to avoid potential misclassifications of base compositions. In other embodiments, base composition probability clouds provide the means for predicting the identity of a bioagent whose assigned base composition was not previously observed and/or indexed in a bioagent identifying amplicon base composition database due to evolutionary transitions in its nucleic acid sequence. Thus, in contrast to probe-based techniques, mass spectrometry determination of base composition does not require prior knowledge of the composition or sequence in order to make the measurement.

The present invention provides bioagent classifying information similar to DNA sequencing and phylogenetic analysis at a level sufficient to detect and identify a given bioagent. Furthermore, the process of determination of a previously unknown base composition for a given bioagent (for example, in a case where sequence information is unavailable) has downstream utility by providing additional bioagent indexing information with which to populate base composition databases. The process of future bioagent identification is thus greatly improved as more BCS indexes become available in base composition databases.

The present invention also provides kits for carrying out the methods described herein. In some embodiments, the kit may comprise a sufficient quantity of one or more primer pairs to perform an amplification reaction on a target polynucleotide from a bioagent to form a bioagent identifying amplicon. In some embodiments, the kit may comprise from one to fifty primer pairs, from one to twenty primer pairs, from one to ten primer pairs, or from two to five primer pairs. In some embodiments, the kit may comprise one or more primer pairs recited in Table 1.

In some embodiments, the kit may comprise broad range survey primers, division wide primers, clade group primers or drill-down primers, or any combination thereof. A kit may be designed so as to comprise particular primer pairs for identification of a particular bioagent. For example, a broad range survey primer kit may be used initially to identify an unknown bioagent as a member of the *Bacillus/Clostridia* group. Another example of a division-wide kit may be used to distinguish *Bacillus anthracis, Bacillus cereus* and *Bacillus thuringiensis* from each other. A drill-down kit may be used, for example, to identify genetically engineered *Bacillus anthracis*. In some embodiments, any of these kits may be combined to comprise a combination of broad range survey primers and division-wide primers so as to be able to identify the species of an unknown bioagent.

In some embodiments, the kit may contain standardized nucleic acids for use as internal amplification calibrants.

In some embodiments, the kit may also comprise a sufficient quantity of reverse transcriptase (if an RNA virus is to be identified for example), a DNA polymerase, suitable nucleoside triphosphates (including any of those described above), a DNA ligase, and/or reaction buffer, or any combination thereof, for the amplification processes described above. A kit may further include instructions pertinent for the particular embodiment of the kit, such instructions describing the primer pairs and amplification conditions for operation of the method. A kit may also comprise amplification reaction containers such as microcentrifuge tubes and the like. A kit may also comprise reagents or other materials for isolating bioagent nucleic acid or bioagent identifying amplicons from amplification, including, for example, detergents, solvents, or ion exchange resins which may be linked to magnetic beads. A kit may also comprise a table of measured or calculated molecular masses and/or base compositions of bioagents using the primer pairs of the kit.

While the present invention has been described with specificity in accordance with certain of its embodiments, the following examples serve only to illustrate the invention and are not intended to limit the same. Throughout these examples, molecular cloning reactions, and other standard recombinant DNA techniques, may be carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1

Design of Calibrant Polynucleotides Based on Viral Bioagent Identifying Amplicons from the SARS Coronavirus (Viral Bioagent Identifying Amplicons)

This example describes the design of two coronavirus calibrant polynucleotides based on viral bioagent identifying amplicons for identification of coronaviruses (viral bioagent identifying amplicons) in the RNA-dependent RNA polymerase (RdRp) gene and in the nsp11 gene which are described in a method for identification of coronaviruses disclosed in U.S. application Ser. No. 10/829,826. The primers used to define the viral bioagent identifying amplicons hybridize to regions of the RdRp gene (primer pair no. 453: forward—TAAGU$^a$U$^a$TU$^a$ATGGCGGCU$^a$GG (SEQ ID NO: 1) and reverse—TTTAGGATAGTC$^a$C$^a$C$^a$ AACCCAT (SEQ ID NO: 2)) and the nsp11 gene (primer pair no. 455: forward—TGTTTG U$^a$U$^a$U$^a$U$^a$GGAATTGTAATGTTGA (SEQ ID NO: 3) and reverse—TGGAATGCATGCUa U$^a$AU$^a$U$^a$AACATACA (SEQ ID NO: 4)), wherein U$^a$ represents=5-propynyluracil and C$^a$ represents 5-propynylcytosine). The calibration sequence chosen to simulate the RdRp calibration amplicon is SEQ ID NO: 5 which corresponds to positions 15146 to 15233 of NC_004718.3 (SARS coronavirus TOR2 genome) with deletion of positions 15179-15183 to yield a calibration amplicon length of 83 bp. The calibration sequence for the nsp11 calibration amplicon is SEQ ID NO: 6, which corresponds to positions 19113 to 19249 of NC_004718.3 (SARS coronavirus TOR2 genome) with deletion of positions 19172-19176 to yield a calibration amplicon of 132 bp length. Both calibrant standard sequences (SEQ ID NOs: 5 and 6) were included on a single polynucleotide (SEQ ID NO: 7—herein designated a "combination calibration polynucleotide") which was cloned into a pCR®-Blunt vector (Invitrogen, Carlsbad, Calif.). Thus, when the combination calibration polynucleotide is added to an amplification reaction, an RdRp-based calibration amplicon will be produced in an amplification reaction with primer pair 453 (SEQ ID NOs: 1:2) and an nsp11-based calibration amplicon will be produced with primer pair 455 (SEQ ID NOs: 3:4).

The viral bioagent identifying amplicons are used as identifiers of coronaviruses due to the variable regions between the conserved priming regions which can be distinguished by mass spectrometry. The calibration polynucleotides are used to produce calibration amplicons from which the quantity of identified coronavirus is determined.

Example 2

Use of a Calibration Polynucleotide for Determining the Quantity of Coronavirus in a Clinical Sample To determine the quantity of SARS coronavirus in a clinical sample, viable SARS coronavirus was added to human serum and analyzed. The TOR2 isolate of the SARS coronavirus from three passages in Vero cells was titered by plaque assay. Virus was handled in a P3 facility by investigators wearing forced air respirators. Equipment and supplies were decontaminated with 10% hypochlorite bleach solution for a minimum of 30 minutes or by immersion in 10% formalin for a minimum of 12 hours and virus was handled in strict accordance with specific Scripps Research Institute policy. SARS coronavirus was cultured in sub confluent Vero-E6 cells at 37° C., 5% $CO_2$ in complete DMEM with final concentrations of 10% fetal bovine serum (Hyclone, Salt Lake City, Utah), 292 μg/mL L-Glutamine, 100 U/mL penicillin G sodium, 100 μg/mL streptomycin sulfate (Invitrogen, Carlsbad Calif.), and 10 mM HEPES (Invitrogen, Carlsbad Calif.). Virus-containing medium was collected during the peak of viral cytopathic effects, 48 h after inoculation with approximately 10 PFU/cell of SARS coronavirus from the second passage of stock virus. Infectious virus was titered by plaque assay. Monolayers of Vero-E6 cells were prepared at 70-80% confluence in tissue culture plates. Serial tenfold dilutions of virus were prepared in complete DMEM. Medium was aspirated from cells, replaced by 200 μL of inoculum, and cells were incubated at 37° C., 5% $CO_2$ for 1 hour. Cells were overlaid with 2-3 mL/well of 0.7% agarose, 1×DMEM overlay containing 2% fetal bovine serum. Agarose was allowed to solidify at room temperature then cells were incubated at 37° C., 5% $CO_2$ for 72 h. Plates were decontaminated by overnight formalin immersion, agarose plugs were removed, and cells were stained with 0.1% crystal violet to highlight viral plaques.

RNA was isolated from serum containing two different concentrations of the virus ($1.7\times10^5$ and 170 PFU/mL) and reverse transcribed to cDNA using random primers and reverse transcriptase. A PFU (plate forming unit) is a quantitative measure of the number of infectious virus particles in a given sample, since each infectious virus particle can give rise to a single clear plaque on infection of a continuous "lawn" of bacteria or a continuous sheet of cultured cells. PCR amplifications were performed using both the RdRp and the nsp11 primer sets on serial ten-fold dilutions of these cDNAs. Amplification products were purified and analyzed by methods commonly owned and disclosed in U.S. application Ser. Nos. 10/829,826 and 10/844,938, each of which is incorporated herein by reference in its entirety. The limit of SARS coronavirus detection was 10-2 PFU per PCR reaction (~1.7 PFU/mL serum). Since PFU reflects the number of infectious viral particles and not the total number of RNA genomes, the number of reverse-transcribed SARS genomes was estimated by competitive, quantitative PCR using a calibration polynucleotide. Analysis of ratios of mass spectral peak heights of titrations of the calibration polynucleotide and the SARS cDNA showed that approximately 300 reverse-transcribed viral genomes were present per PFU, similar to the ratio of viral genome copies per PFU reported for RNA viruses (J. S. Towner et al., J Virol In Press (2004)). Using this estimate, the PCR primers were sensitive to three genomes per PCR reaction, consistent with previously reported detection limits for optimized SARS-specific primers (Drosten et al., *New England Journal of Medicine,* 2003, 348, 1967). When RT-PCR products were measured for varying dilutions of the SARS virus spiked directly into serum, 1 PFU (~300 genomes) per PCR reaction or 170 PFU (5.1×104 genomes) per mL serum could be reliably detected. The discrepancy between the detection sensitivities in the two experimental protocols described above suggests that there were losses associated with RNA extraction and reverse transcription when very little virus was present (<300 copies) in the starting sample in serum.

Figure 2:
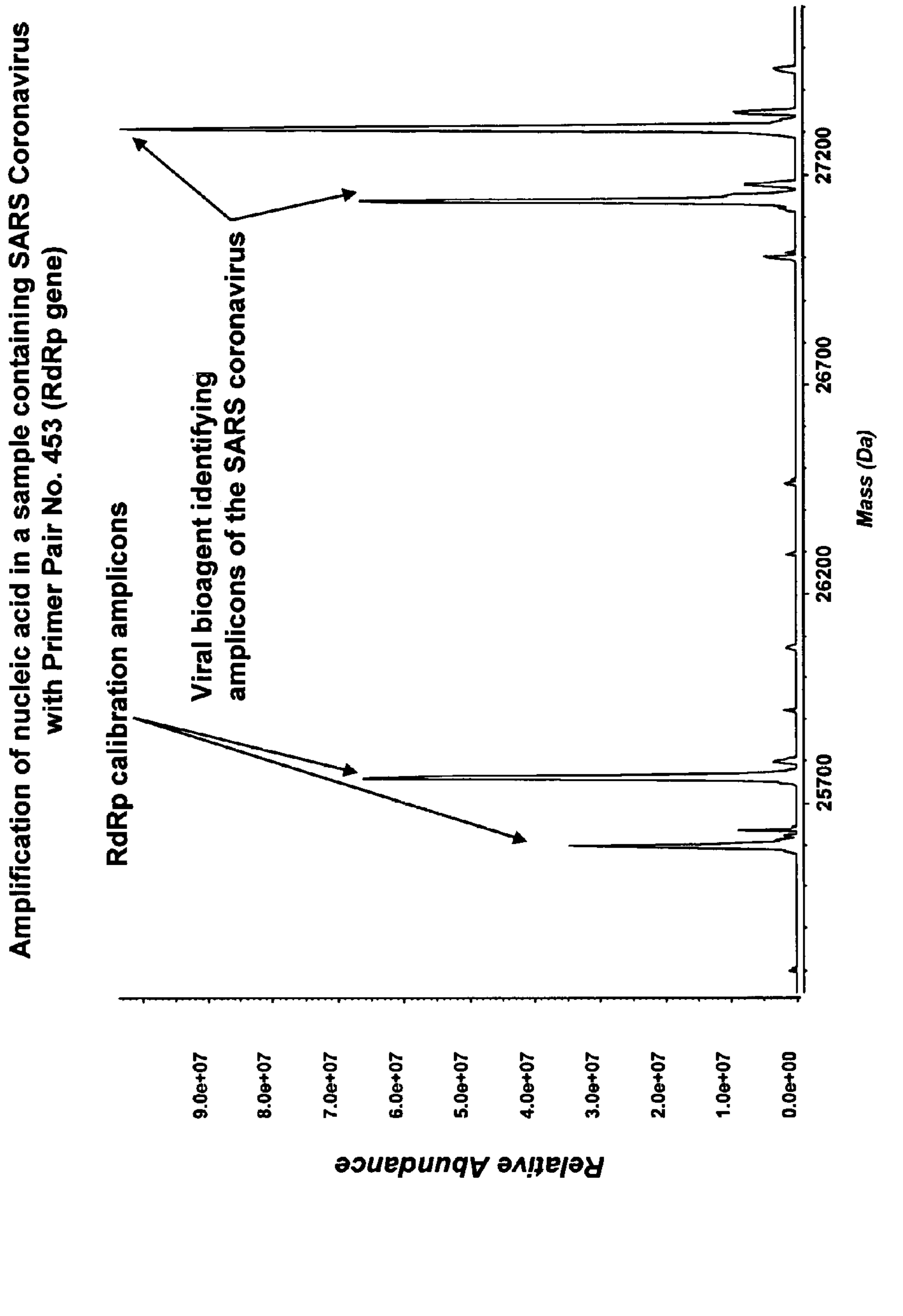
FIG. 2 shows a representative mass spectrum of a viral bioagent identifying amplicon for the RdRp primer set of the SARS coronavirus (SARS) and the corresponding RdRp calibration amplicon.

To determine the relationship between PFU and copies of nucleic acid target, the virus stock was analyzed using the methods of the present invention. Synthetic DNA templates with nucleic acid sequence identical in all respects to RdRp-based (SEQ ID NO: 5) and nsp11-based (SEQ ID NO: 6) viral bioagent identifying amplicons for the SARS coronavirus with the exception of 5 base deletions internal to each amplicon were combined into a single combination calibration polynucleotide (SEQ ID NO: 7) and cloned into a pCR®-Blunt vector (Invitrogen, Carlsbad, Calif.) to produce a calibration polynucleotide. The calibrant plasmid stock solutions were quantified using $OD_{260}$ measurements, serially diluted (10-fold dilutions), and mixed with a fixed amount of post-reverse transcriptase cDNA preparation of the virus stock and analyzed by competitive PCR and electrospray mass spectrometry. Each PCR reaction produced two sets of amplicons, one corresponding to the calibrant amplicon and the other to the viral bioagent identifying amplicon. Since the primers hybridize to both the calibration polynucleotide and the coronavirus cDNA, it was reasonably assumed that the calibration polynucleotide and coronavirus cDNA would have similar PCR efficiencies for amplification of the two products. Analysis of the ratios of peak heights (abundance data) of the resultant mass spectra of the calibration amplicons DNA and viral bioagent identifying amplicons used to determine the amounts of nucleic acid copies (as measured by calibrant molecules) present per PFU. Since all of the extracted RNA was used in the reverse transcriptase step to produce the viral cDNA, the approximate amount of nucleic acids associated with infectious virus particles in the original viral preparation could be estimated. Mass spectrometry analysis showed an approximate 1:1 peak abundance between the calibrant peak at the $3\times10^4$ copy number dilution and the viral bioagent identifying amplicon peak for the RdRp primer set (FIG. 2). Thus, the relationship between PFU and copies of nucleic acid was calculated to be 1 PFU=300 copies of nucleic acid.

The calibration sequences described in this example are appropriate for use in production of calibration amplicons which are in turn useful for determining the quantity of all known members of the coronavirus family. Further, it is reasonably expected that these calibration sequences will likewise be appropriate for quantification of any coronaviruses that are yet to be discovered.

Example 3

Design of Calibrant Polynucleotides based on Bioagent Identifying Amplicons for Identification of Species of Bacteria (Bacterial Bioagent Identifying Amplicons)

This example describes the design of 19 calibrant polynucleotides based on broad range bacterial bioagent identifying amplicons. The bacterial bioagent identifying amplicons are obtained upon amplification of bacterial nucleic acid with primers (Table 1) that have been disclosed in U.S. patent application Ser. Nos. 10/660,122, 10,728,486, and 60/559,754, each of which is commonly owned and incorporated herein by reference in its entirety.

Calibration sequences were designed to simulate bacterial bioagent identifying amplicons produced by the primer pairs shown in Table 1. The calibration sequences were chosen as a representative member of the section of bacterial genome from specific bacterial species which would be amplified by a given primer pair. The model bacterial species upon which the calibration sequences are based are also shown in Table 1. For example, the calibration sequence chosen to correspond to an amplicon produced by primer pair no. 346 is SEQ ID NO: 8. In Table 1, the forward (_F) or reverse (_R) primer name indicates the coordinates of an extraction representing a gene of a standard reference bacterial genome to which the primer hybridizes e.g.: the forward primer name 16S_EC_713_732_TMOD_F indicates that the forward primer hybridizes to residues 713-732 of the gene encoding 16S ribosomal RNA in an *E. coli* reference sequence (in this case, the reference sequence (SEQ ID NO: 66 in Table 2) is an extraction consisting of residues 4033120-403-4661 of the genomic sequence of *E. coli* K12 (GenBank Accession No. NC_000913)—See Table 2. Additional gene coordinate reference information is shown in Table 2. The designation "TMOD" in the primer names indicates that the 5' end of the primer has been modified with a non-matched template T residue. This modification prevents the PCR polymerase from adding non-templated adenosine residues to the 5' end of the amplification product, an occurrence which may result in miscalculation of base composition from molecular mass data.

The 19 calibration sequences shown in Table 1 were combined into a single calibration polynucleotide sequence (SEQ ID NO: 9—which is herein designated a "combination calibration polynucleotide") which was then cloned into a pCR®-Blunt vector (Invitrogen, Carlsbad, Calif.). This combination calibration polynucleotide can be used in conjunction with the primers of Table 1 as an internal standard to produce calibration amplicons for use in determination of the quantity of any bacterial bioagent. Thus, for example, when the combination calibration polynucleotide vector is present in an amplification reaction mixture, a calibration amplicon based on primer pair 346 (16S rRNA) will be produced in an amplification reaction with primer pair 346 and a calibration amplicon based on primer pair 363 (rpoC) will be produced with primer pair 363.

TABLE 1

Bacterial Primer Pairs for Production of Bacterial Bioagent Identifying Amplicons and Corresponding Representative Calibration Sequences

| Primer Pair No. | Forward Primer Name | Forward Primer (SEQ ID NO:) | Reverse Primer Name | Reverse Primer (SEQ ID NO:) | Calibration Sequence Model Species | Calibration Sequence (SEQ ID NO:) |
|---|---|---|---|---|---|---|
| 346 | 16S_EC_713_732_TMOD_F | 10 | 16S_EC_789_809_TMOD_R | 11 | *Bacillus anthracis* | 8 |
| 347 | 16S_EC_785_806_TMOD_F | 12 | 16S_EC_880_897_TMOD_R | 13 | *Bacillus anthracis* | 14 |
| 348 | 16S_EC_960_981_TMOD_F | 15 | 16S_EC_1054_1073_TMOD_R | 16 | *Bacillus anthracis* | 17 |
| 349 | 23S_EC_1826_1843_TMOD_F | 18 | 23S_EC_1906_1924_TMOD_R | 19 | *Bacillus anthracis* | 20 |
| 350 | CAPC_BA_274_303_TMOD_F | 21 | CAPC_BA_349_376_TMOD_R | 22 | *Bacillus anthracis* | 23 |
| 351 | CYA_BA_1353_1379_TMOD_F | 24 | CYA_BA_1448_1467_TMOD_R | 25 | *Bacillus anthracis* | 26 |
| 352 | INFB_EC_1365_1393_TMOD_F | 27 | INFB_EC_1439_1467_TMOD_R | 28 | *Bacillus anthracis* | 29 |
| 353 | LEF_BA_756_781_TMOD_F | 30 | LEF_BA_843_872_TMOD_R | 31 | *Bacillus anthracis* | 32 |
| 354 | RPOC_EC_2218_2241_TMOD_F | 33 | RPOC_EC_2313_2337_TMOD_R | 34 | *Bacillus anthracis* | 35 |
| 355 | SSPE_BA_115_137_TMOD_F | 36 | SSPE_BA_197_222_TMOD_R | 37 | *Bacillus anthracis* | 38 |
| 356 | RPLB_EC_650_679_TMOD_F | 39 | RPLB_EC_739_762_TMOD_R | 40 | *Clostridium botulinum* | 41 |

TABLE 1-continued

Bacterial Primer Pairs for Production of Bacterial Bioagent Identifying Amplicons and Corresponding Representative Calibration Sequences

| Primer Pair No. | Forward Primer Name | Forward Primer (SEQ ID NO:) | Reverse Primer Name | Reverse Primer (SEQ ID NO:) | Calibration Sequence Model Species | Calibration Sequence (SEQ ID NO:) |
|---|---|---|---|---|---|---|
| 358 | VALS_EC_1105_1124_TMOD_F | 42 | VALS_EC_1195_1218_TMOD_R | 43 | *Yersinia Pestis* | 44 |
| 359 | RPOB_EC_1845_1866_TMOD_F | 45 | RPOB_EC_1909_1929_TMOD_R | 46 | *Yersinia Pestis* | 47 |
| 360 | 23S_EC_2646_2667_TMOD_F | 48 | 23S_EC_2745_2765_TMOD_R | 49 | *Bacillus anthracis* | 50 |
| 361 | 16S_EC_1090_1111_2_TMOD_F | 51 | 16S_EC_1175_1196_TMOD_R | 52 | *Bacillus anthracis* | 53 |
| 362 | RPOB_EC_3799_3821_TMOD_F | 54 | RPOB_EC_3862_3888_TMOD_R | 55 | *Burkholderia mallei* | 56 |
| 363 | RPOC_EC_2146_2174_TMOD_F | 57 | RPOC_EC_2227_2245_TMOD_R | 58 | *Burkholderia mallei* | 59 |
| 367 | TUFB_EC_957_979_TMOD_F | 60 | TUFB_EC_1034_1058_TMOD_R | 61 | *Burkholderia mallei* | 62 |
| 449 | RPLB_EC_690_710_F | 63 | RPLB_EC_737_758_R | 64 | *Clostridium botulinum* | 65 |

TABLE 2

Primer Pair Gene Coordinate References and Calibration Polynucleotide Sequence Coordinates within the Combination Calibration Polynucleotide

| Bacterial Gene | Primer Pair No. | Gene Extraction SEQ ID NO: | Gene Extraction Coordinates or Genomic or Plasmid Sequence | GenBank Accession No. of Genomic (G) or Plasmid (P) Sequence | Coordinates of Calibration Sequence in Combination Calibration Polynucleotide (SEQ ID NO: 9) |
|---|---|---|---|---|---|
| 16S *E. coli* | 346 | 66 | 4033120 . . . 4034661 | NC_000913 (G) | 16 . . . 109 |
| 16S *E. coli* | 347 | 66 | 4033120 . . . 4034661 | NC_000913 (G) | 83 . . . 190 |
| 16S *E. coli* | 348 | 66 | 4033120 . . . 4034661 | NC_000913 (G) | 246 . . . 353 |
| 16S *E. coli* | 361 | 66 | 4033120 . . . 4034661 | NC_000913 (G) | 368 . . . 469 |
| 23S *E. coli* | 349 | 67 | 4166220 . . . 4169123 | NC_000913 (G) | 743 . . . 837 |
| 23S *E. coli* | 360 | 67 | 4166220 . . . 4169123 | NC_000913 (G) | 865 . . . 981 |
| rpoB *E. coli*. | 359 | 68 | 4178823 . . . 4182851 (complement strand) | NC_000913 (G) | 1591 . . . 1672 |
| rpoB *E. coli* | 362 | 68 | 4178823 . . . 4182851 (complement strand) | NC_000913 (G) | 2081 . . . 2167 |
| rpoC *E. coli* | 354 | 69 | 4182928 . . . 4187151 | NC_000913 (G) | 1810 . . . 1926 |
| rpoC *E. coli* | 363 | 69 | 4182928 . . . 4187151 | NC_000913 (G) | 2183 . . . 2279 |
| infB *E. coli* | 352 | 70 | 3313655 . . . 3310983 (complement strand) | NC_000913 (G) | 1692 . . . 1791 |
| tufB *E. coli* | 367 | 71 | 4173523 . . . 4174707 | NC_000913 (G) | 2400 . . . 2498 |
| rplB *E. coli* | 356 | 72 | 3449001 . . . 3448180 | NC_000913 (G) | 1945 . . . 2060 |
| rplB *E. coli* | 449 | 72 | 3449001 . . . 3448180 | NC_000913 (G) | 1986 . . . 2055 |
| valS *E. coli* | 358 | 73 | 4481405 . . . 4478550 (complement strand) | NC_000913 (G) | 1462 . . . 1572 |
| capC *B. anthracis* | 350 | 74 | 56074 . . . 55628 (complement strand) | AF188935 (P) | 2517 . . . 2616 |
| Cya *B. anthracis* | 351 | 75 | 156626 . . . 154288 (complement strand) | AF065404 (P) | 1338 . . . 1449 |
| Lef *B. anthracis* | 353 | 76 | 127442 . . . 129921 | AF065404 (P) | 1121 . . . 1234 |
| sspE *B. anthracis* | 355 | 77 | 226496 . . . 226783 | AE017025 (G) | 1007-1104 |

Example 4

Figure 3:
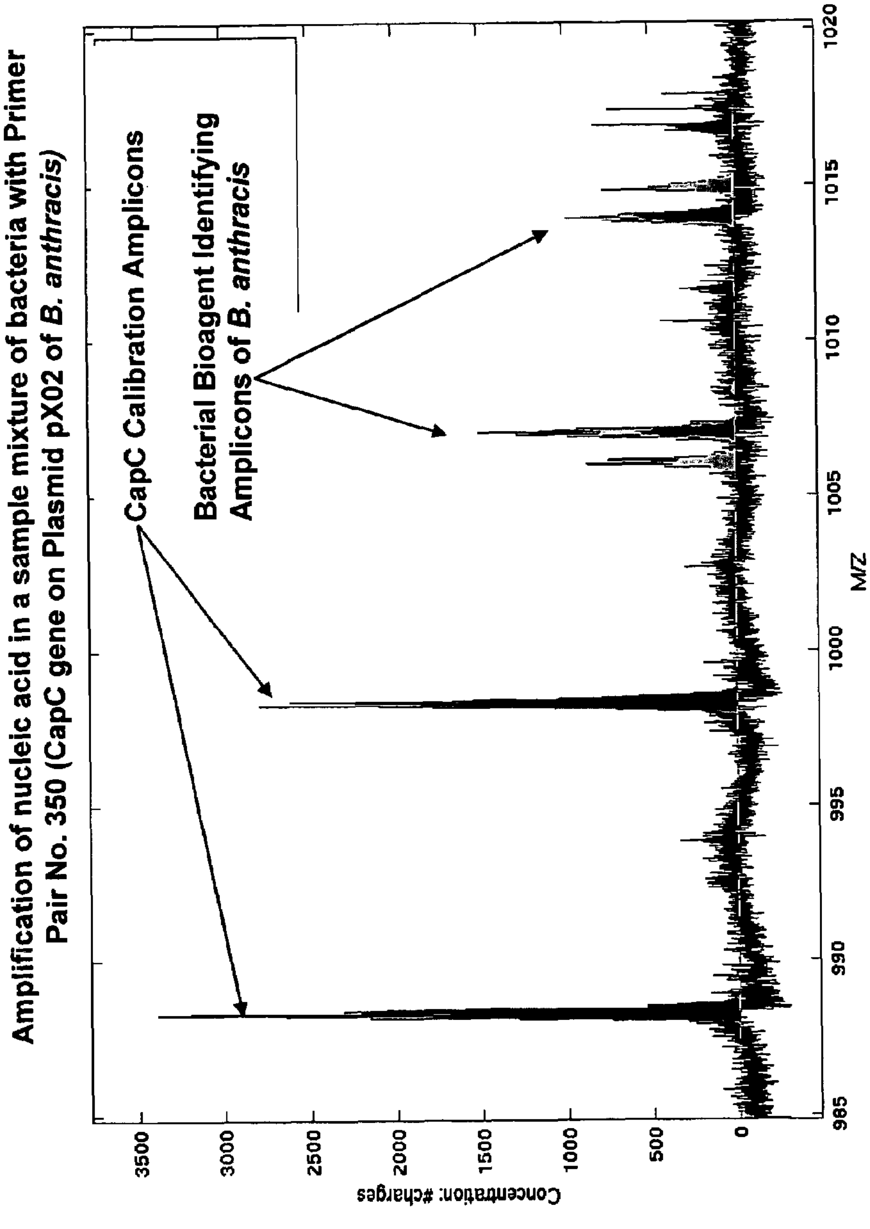
FIG. 3 shows a representative mass spectrum of an amplified nucleic acid mixture containing the Ames strain of *Bacillus anthracis*, a known quantity of combination calibration polynucleotide vector which includes the CapC calibration sequence for *Bacillus anthracis* and primer pair 350 (see Example 4).

Use of a Calibration Polynucleotide for Determining the Quantity of *Bacillus Anthracis* in a Sample Containing a Mixture of Microbes The capC gene is a gene involved in capsule synthesis which resides on the pX02 plasmid of *Bacillus anthracis*. Primer pair no. 350 (see Tables 1 and 2) was designed to identify *Bacillus anthracis* via production of a bacterial bioagent identifying amplicon. Known quantities of the combination calibration polynucleotide vector described in Example 3 were added to amplification mixtures containing bacterial bioagent nucleic acid from a mixture of microbes which included the Ames strain of *Bacillus anthracis*. Upon amplification of the bacterial bioagent nucleic acid and the combination calibration polynucleotide vector with primer pair no. 350, bacterial bioagent identifying amplicons and calibration amplicons were obtained and characterized by mass spectrometry. A spectrum of an amplified nucleic acid mixture containing the Ames strain of *Bacillus anthracis*, a known quantity of combination calibration polynucleotide vector which includes the CapC calibration sequence for *Bacillus anthracis* and primer pair 350 is shown in FIG. 3. The molecular masses of the bioagent identifying amplicons provided the means for identification of the bioagent from which they were obtained (Ames strain of *Bacillus anthracis*) and the molecular masses of the calibration amplicons provided the means for their identification as well. The relationship between the abundance (peak height) of the calibration amplicon signals and the bacterial bioagent identifying amplicon signals provides the means of calculation of the copies of the pX02 plasmid of the Ames strain of *Bacillus anthracis*. Methods of calculating quantities of molecules based on internal calibration procedures are well known to those of ordinary skill in the art.

Calibration amplicons and bacterial bioagent identifying amplicons produced in the reaction are visible in the mass spectrum as indicated and abundance (peak height) data are used to calculate the quantity of the pX02 plasmid of the Ames strain of *Bacillus anthracis* in the sample. Averaging the results of 10 repetitions of the experiment described above, enabled a calculation that indicated that the quantity of Ames strain of *Bacillus anthracis* present in the sample corresponds to approximately 10 copies of pX02 plasmid.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method for simultaneous analysis of the identity and quantity of a bioagent in a sample comprising:

contacting nucleic acid of said sample with:

a pair of primers designed to produce a bioagent identifying amplicon from said nucleic acid under polymerase chain reaction amplification conditions; and a known quantity of a calibration polynucleotide comprising a calibration sequence designed to produce a calibration amplicon as a result of polymerase chain reaction amplification with said primers under said amplification conditions;

concurrently amplifying said nucleic acid and said calibration sequence with said pair of primers in the same amplification mixture to obtain a first polymerase chain reaction amplification product comprising a bioagent identifying amplicon and a second polymerase chain reaction amplification product comprising a calibration amplicon;

obtaining molecular mass data and abundance data for said first and second polymerase chain reaction amplification products in said amplification mixture wherein the 5' and 3' ends of said amplification products are the sequences of said pair of primers or complements thereof;

distinguishing said first and second polymerase chain reaction amplification products based on their respective molecular masses, wherein the molecular mass of said first polymerase chain reaction amplification product identifies said bioagent, and the molecular mass of said second polymerase chain reaction amplification product identifies said calibration amplicon; and calculating the quantity of said bioagent from said abundance data of said first and second polymerase chain reaction amplification products.

2. A method for determining the identity and quantity of a bioagent in a sample comprising:

contacting said sample with a pair of primers and a known quantity of a calibration polynucleotide comprising a calibration sequence;

concurrently amplifying nucleic acid from said bioagent in said sample with a polymerase chain reaction and said pair of primers and amplifying nucleic acid from said calibration polynucleotide in said sample with a polymerase chain reaction and said pair of primers to obtain a first polymerase chain reaction amplification product comprising a bioagent identifying amplicon and a second polymerase chain reaction amplification product comprising a calibration amplicon;

obtaining molecular mass and abundance data for said bioagent identifying amplicon and for said calibration amplicon wherein the 5' and 3' ends of said amplicons are the sequences of said pair of primers or complements thereof; and distinguishing said bioagent identifying amplicon from said calibration amplicon based on their respective molecular masses, wherein the molecular mass of said bioagent identifying amplicon indicates the identity of said bioagent, and comparison of bioagent identifying amplicon abundance data and calibration amplicon abundance data indicates the quantity of bioagent in said sample.

3. The method of claim 2 wherein said bioagent is a bacterium or a virus.

4. The method of claim 2 wherein said calibration sequence comprises a chosen standard sequence of a bioagent identifying amplicon with the exception of a deletion of about 2 to about 8 consecutive nucleotide residues of said standard sequence.

5. The method of claim 2 wherein said calibration sequence comprises a chosen standard sequence of a bioagent identifying amplicon with the exception of an insertion of about 2 to about 8 consecutive nucleotide residues of said standard sequence.

6. The method of claim 2 wherein said calibration sequence has at least 80% sequence identity with a chosen standard sequence of a bioagent identifying amplicon.

7. The method of claim 2 wherein said calibration polynucleotide is present within a vector.

8. The method of claim 2 wherein said molecular mass is obtained by mass spectrometry.

9. The method of claim 2 wherein said molecular mass is obtained by ESI-FTICR or ESI-TOF mass spectrometry.

10. The method of claim 2 wherein said molecular mass of said bioagent identifying amplicon identifies said bioagent as a result of determination of the base composition of said bioagent identifying amplicon.

11. A method for determining the identity and quantity of a bacterium or a virus in a sample comprising:

contacting said sample with a pair of primers and a known quantity of a calibration polynucleotide comprising a calibration sequence;

concurrently amplifying nucleic acid from said bacterium or virus in said sample with a polymerase chain reaction and said pair of primers and amplifying nucleic acid from said calibration polynucleotide in said sample with a polymerase chain reaction and said pair of primers to obtain a first polymerase chain reaction amplification product comprising a bacterial or viral bioagent identifying amplicon and a second polymerase chain reaction amplification product comprising a calibration amplicon;

obtaining the molecular mass and abundance data for said bacterial or viral bioagent identifying amplicon and for said calibration amplicon wherein the 5' and 3' ends of said bioagent identifying amplicon and said calibration amplicon are the sequences of said pair of primers or complements thereof; and distinguishing said bacterial or viral bioagent identifying amplicon from said calibration amplicon based on their respective molecular masses, wherein the molecular mass of said bacterial or viral bioagent identifying amplicon indicates the identity of said bacterium or virus, and comparison of bacterial or viral bioagent identifying amplicon abundance data and calibration amplicon abundance data indicates the quantity of bacterium or virus in said sample.

12. The method of claim 11 wherein said virus is an RNA virus whose RNA is reverse transcribed to DNA which represents said nucleic acid amplified by said pair of primers.

13. The method of claim 12 wherein said reverse transcribing is accomplished using reverse transcriptase.

14. The method of claim 11 wherein said virus is a DNA virus whose DNA represents said nucleic acid amplified by said primers.

15. The method of claim 11 wherein said calibration sequence comprises the sequence of a chosen standard sequence of a bacterial or viral bioagent identifying amplicon with the exception of a deletion of about 2 to about 8 consecutive nucleotide residues of said standard sequence.

16. The method of claim 11 wherein said calibration sequence comprises the sequence of a chosen standard sequence of a bacterial or viral bioagent identifying amplicon with the exception of an insertion of about 2 to about 8 consecutive nucleotide residues of said standard sequence.

17. The method of claim 11 wherein said calibration sequence has at least 80% sequence identity with a chosen standard sequence of a viral bioagent identifying amplicon.

18. The method of claim 11 wherein said calibration polynucleotide is present within a vector.

19. The method of claim 11 wherein said molecular mass is obtained by mass spectrometry.

20. The method of claim 11 wherein said molecular mass is obtained by ESI-FTICR or ESI-TOF mass spectrometry.

21. A method for simultaneous analysis of the identity and quantity of a bioagent in a sample comprising:

contacting nucleic acid of said sample with:

a pair of primers designed to produce a bioagent identifying amplicon from said nucleic acid under amplification conditions; and a known quantity of a calibration polynucleotide comprising a calibration sequence designed to produce a calibration amplicon as a result of amplification with said primers under said amplification conditions;

concurrently amplifying said nucleic acid and said calibration sequence with said pair of primers in the same amplification mixture to obtain a first amplification product comprising a bioagent identifying amplicon and a second amplification product comprising a calibration amplicon;

obtaining molecular mass data and abundance data for said first and second amplification products in said amplification mixture wherein the 5' and 3' ends of said amplification products are the sequences of said pair of primers or complements thereof;

distinguishing said first and second amplification products based on their respective molecular masses, wherein the molecular mass of said first amplification product identifies said bioagent, and the molecular mass of said second amplification product identifies said calibration amplicon; and calculating the quantity of said bioagent from said abundance data of said first and second amplification products.

22. A method for determining the identity and quantity of a bioagent in a sample consisting of:

contacting said sample with a pair of primers and a known quantity of a calibration polynucleotide comprising a calibration sequence;

concurrently amplifying nucleic acid from said bioagent in said sample with said pair of primers and amplifying nucleic acid from said calibration polynucleotide in said sample with said pair of primers to obtain a first amplification product comprising a bioagent identifying amplicon and a second amplification product comprising a calibration amplicon;

obtaining molecular mass and abundance data for said bioagent identifying amplicon and for said calibration amplicon wherein the 5' and 3' ends of said bioagent identifying amplicon and said calibration amplicon are the sequences of said pair of primers or complements thereof; and distinguishing said bioagent identifying amplicon from said calibration amplicon based on their respective molecular masses, wherein the molecular mass of said bioagent identifying amplicon indicates the identity of said bioagent, and comparison of bioagent identifying amplicon abundance data and calibration amplicon abundance data indicates the quantity of bioagent in said sample.

23. The method of claim 22 wherein said bioagent is a bacterium or a virus.

24. The method of claim 22 wherein said calibration sequence comprises a chosen standard sequence of a bioagent identifying amplicon with the exception of a deletion of about 2 to about 8 consecutive nucleotide residues of said standard sequence.

25. The method of claim 22 wherein said calibration sequence comprises a chosen standard sequence of a bioagent identifying amplicon with the exception of an insertion of about 2 to about 8 consecutive nucleotide residues of said standard sequence.

26. The method of claim 22 wherein said calibration sequence has at least 80% sequence identity with a chosen standard sequence of a bioagent identifying amplicon.

27. The method of claim 22 wherein said calibration polynucleotide is present within a vector.

28. The method of claim 22 wherein said molecular mass is obtained by mass spectrometry.

29. The method of claim 22 wherein said molecular mass is obtained by ESI-FTICR or ESI-TOF mass spectrometry.

30. The method of claim 22 wherein said molecular mass of said bioagent identifying amplicon identifies said bioagent as a result of determination of the base composition of said bioagent identifying amplicon.

* * * * *

SEQUENCE LISTING

```
<160> NUMBER OF SEQ ID NOS: 77

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1

taagttttat ggcggctgg                                                   19


<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2

tttaggatag tcccaaccca t                                                21


<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3

tgtttgtttt ggaattgtaa tgttga                                           26


<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4

tggaatgcat gcttattaac ataca                                            25


<210> SEQ ID NO 5
<211> LENGTH: 83
```

-continued

<212> TYPE: DNA
<213> ORGANISM: Artificial Sequence
<220> FEATURE:
<223> OTHER INFORMATION: Oligonucleotide

<400> SEQUENCE: 5
caagttttac ggtggctggc ataatatgtt aaatttacag tgatgtagaa actccacacc 60
ttatgggttg ggattatcca aaa 83

<210> SEQ ID NO 6
<211> LENGTH: 132
<212> TYPE: DNA
<213> ORGANISM: Artificial Sequence
<220> FEATURE:
<223> OTHER INFORMATION: Oligonucleotide

<400> SEQUENCE: 6
tgtttgtttt ggaattgtaa cgttgatcgt tacccagcca atgcaattgt gtgtaggttc 60
aagagtcttg tcaaacttga acttaccagg ctgtgatggt ggtagtttgt atgtgaataa 120
gcatgcattc ca 132

<210> SEQ ID NO 7
<211> LENGTH: 265
<212> TYPE: DNA
<213> ORGANISM: Artificial Sequence
<220> FEATURE:
<223> OTHER INFORMATION: Oligonucleotide

<400> SEQUENCE: 7
tggaacaagc aagttttacg gtggctggca taatatgtta aatttacagt gatgtagaaa 60
ctccacacct tatgggttgg gattatccaa aatgtgacag aggataaatt cactgatggt 120
gtttgtttgt tttggaattg taacgttgat cgttacccag ccaatgcaat tgtgtgtagg 180
ttcaagagtc ttgtcaaact tgaacttacc aggctgtgat ggtggtagtt tgtatgtgaa 240
taagcatgca ttccacactc cagct 265

<210> SEQ ID NO 8
<211> LENGTH: 1542
<212> TYPE: DNA
<213> ORGANISM: Artificial Sequence
<220> FEATURE:
<223> OTHER INFORMATION: Oligonucleotide

<400> SEQUENCE: 8
aaattgaaga gtttgatcat ggctcagatt gaacgctggc ggcaggccta acacatgcaa 60
gtcgaacggt aacaggaaga agcttgcttc tttgctgacg agtggcggac gggtgagtaa 120
tgtctgggaa actgcctgat ggagggggat aactactgga aacggtagct aataccgcat 180
aacgtcgcaa gaccaaagag ggggaccttc gggcctcttg ccatcggatg tgcccagatg 240
ggattagcta gtaggtgggg taacggctca cctaggcgac gatccctagc tggtctgaga 300
ggatgaccag ccacactgga actgagacac ggtccagact cctacgggag gcagcagtgg 360
ggaatattgc acaatgggcg caagcctgat gcagccatgc cgcgtgtatg aagaaggcct 420
tcgggttgta aagtactttc agcggggagg aagggagtaa agttaatacc tttgctcatt 480
gacgttaccc gcagaagaag caccggctaa ctccgtgcca gcagccgcgg taatacggag 540
ggtgcaagcg ttaatcggaa ttactgggcg taaagcgcac gcaggcggtt tgttaagtca 600
gatgtgaaat ccccgggctc aacctgggaa ctgcatctga tactggcaag cttgagtctc 660

-continued

```
gtagaggggg gtagaattcc aggtgtagcg gtgaaatgcg tagagatctg gaggaatacc    720

ggtggcgaag gcggcccccct ggacgaagac tgacgctcag gtgcgaaagc gtggggagca    780

aacaggatta gataccctgg tagtccacgc cgtaaacgat gtcgacttgg aggttgtgcc    840

cttgaggcgt ggcttccgga gctaacgcgt taagtcgacc gcctggggag tacggccgca    900

aggttaaaac tcaaatgaat tgacgggggc ccgcacaagc ggtggagcat gtggtttaat    960

tcgatgcaac gcgaagaacc ttacctggtc ttgacatcca cggaagtttt cagagatgag   1020

aatgtgcctt cgggaaccgt gagacaggtg ctgcatggct gtcgtcagct cgtgttgtga   1080

aatgttgggt taagtcccgc aacgagcgca acccttatcc tttgttgcca gcggtccggc   1140

cgggaactca aaggagactg ccagtgataa actggaggaa ggtggggatg acgtcaagtc   1200

atcatggccc ttacgaccag ggctacacac gtgctacaat ggcgcataca aagagaagcg   1260

acctcgcgag agcaagcgga cctcataaag tgcgtcgtag tccggattgg agtctgcaac   1320

tcgactccat gaagtcggaa tcgctagtaa tcgtggatca gaatgccacg gtgaatacgt   1380

tcccgggcct tgtacacacc gcccgtcaca ccatgggagt gggttgcaaa agaagtaggt   1440

agcttaacct tcgggagggc gcttaccact ttgtgattca tgactggggt gaagtcgtaa   1500

caaggtaacc gtaggggaac ctgcggttgg atcacctcct ta                      1542


<210> SEQ ID NO 9
<211> LENGTH: 2628
<212> TYPE: DNA
<213> ORGANISM: Artificial Sequence
<220> FEATURE:
<223> OTHER INFORMATION: Oligonucleotide

<400> SEQUENCE: 9

gaagtagaga tatggaggaa caccagtggc gaaggcgact ttctggtctg taactgacac     60

tgagaaagcg tggggagcaa acaggattag ataccctggt agtccacgcc gtaaacgatg    120

agtgctaagt gttagaggcc tttagtgctg aagttaacgc attaagcact ccgcctgggg    180

agtacggccg caaggctgaa actcaaagga attgacgggg cacaagcggt ggagcatgtg    240

gtttaattcg aagcaacgcg aagaacctta ccaggtcttg acatcctctg acaaccctag    300

cttctccttc gggagcagag tgacaggtgg tgcatggttg tcgtcagctc gtgtcgtgag    360

atgttgggtt aagtcccgca acgagcgcaa cccttgatct tagttgttta gttgggcact    420

ctaaggtgac tgccggtgac aaaccggagg aaggtgggga tgacgtcaaa tcatcatgcc    480

ccagtaccgt gagggaaagg tgaaaagcac cccggaaggg gagtgaaaga gatcctgaaa    540

ccgtgtgcca tagtcagagc ccgttaacgg gtgatggcgt gccttttgta gaatgaaccg    600

gcgagttata agatccgtag tcaaaaggga aacagcccag accgccagct aaggtcccaa    660

agtgtgtatt gaaaaggatg tggagttgct tagacaacta ggatgttggc ttagaagcag    720

ccaccattta aagagtatag gggtgacac ctgcccggtg ctggaaggtt aaggagaggg     780

gttagcgtaa ctctgaactg aagccccagt aaacggcggc cgtaactata acggtcctaa    840

ggtagcgaaa gaaatttgag aggagctgtc cttagtacga gaggaccggg atggacgcac    900

cggtaccagt tgttctgcca agggcatagc tgggtagcta tgtgcggaag ggataagtgc    960

tgaaagcatc taagcatgaa gcccccctca agatgagagc agtaaaacaa gcaaacgcac   1020

aatcagaagc taagaaagcg caagcttctg gaaagcacaa atgctagtta tggtacagaa   1080

tttgcaactg aaacagacgt gcatgctgtg aaatttgcga aagcttttgc atattatatc   1140

gagccacagc atcgtgatgt tttacagctt tatgcaccgg aagcttttaa tggataaatt   1200
```

-continued taacgaacaa gaaataaatc tatccttgga agaacttaaa gatcaacgga tgctggcaag 1260
atatgaaaaa taagataaaa cagcactatc aacactggag cgattcttta tctgaagaag 1320
gaagagcgat gaaaacaacg aagtacaata caagacaaaa gaaggtaaaa ttactgtttt 1380
aggggaaaaa ttcaagaaat atagaagtga tggctaaaaa tgtagaaggg gtcttgaagc 1440
cgttaacagc tgttatggcg accgtggcgg cgtggttatc gaacccatgc tgaccgatca 1500
atggtacgtg cacaccgccc cccaaagtcg cgattgaagc cgtagagaac ggcgagatcc 1560
agttcgtccc taaacagtac ggcaacttcg ttatcgctca ggcgaactcc aacctggatg 1620
atgaaggccg ctttttagaa ggtgacttgt cgtagcaaag gcgaatcaag cctgtttagc 1680
cacaactatg cgtgctcgtg gtgcacaagt aacggatatt acaatcattg ttgttgcagc 1740
tgatgacggc gtaataaaca gttgaagcga ttaaccatgc gaaagcagca ggagtaccaa 1800
ctttactcag cttgctggta tgcgtggtct gatggccaat ccatctggtc gtatcatcga 1860
acttccaatc aagtttccgt gaaggtttaa cagtacttga gtacttcatc tctacgcatg 1920
gtgcgcgtaa aggtcatggg agtaagacct acagtaagag gttctgtaat gaaccctaat 1980
gaccatccac acggtggtgg tgaaggtaga tctcctatcg gaaagtccac gtactccatg 2040
gggtaaacca gcacttggat acaaaacaag cgcagttcgg cggccagcgc ttcggtgaaa 2100
tggaagtggc tcgaagcgta tggcgcttcg tacgtgctgc aggaaatgct gacggtgaag 2160
tcggacgacg tgaccggacg cgccaggaat cgttcaactc gatctacatg atggccgacc 2220
gcccggggtt cggcggtgca gattcgtcag ctggccggca tgcgcggcct gatggcgaag 2280
ccggacgcgg cgttcaacgc cgacttcgac ggtgaccagc gttcacgtgc cgctgtcgct 2340
cgaagcgcag atggaagcgc gcacgctgat gctcgcgtcg aacaacgacg aaggcggccg 2400
ccacacgccg ttcttcaaca actaccgtgt tctacttccg tacgacggac gtgacgggct 2460
cgatcgagct gccgaaggac aaggaaatgg tgatgccggg cgacaacact tttatttgat 2520
tattgttatc ctgttatgcc atttgagatt tttgagtggt attggagtta ttgttccagg 2580
attaattgca aatacaattc aaagacaagg gttaccatta acaatcat 2628

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
tagaacaccg atggcgaagg c 21

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
tcgtggacta ccagggtatc ta 22

<210> SEQ ID NO 12
<211> LENGTH: 23
<212> TYPE: DNA
<213> ORGANISM: Artificial Sequence
<220> FEATURE:

-continued

<223> OTHER INFORMATION: Primer

<400> SEQUENCE: 12
tggattagag accctggtag tcc 23

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
tggccgtact ccccaggcg 19

<210> SEQ ID NO 14
<211> LENGTH: 108
<212> TYPE: DNA
<213> ORGANISM: Artificial Sequence
<220> FEATURE:
<223> OTHER INFORMATION: Oligonucleotide

<400> SEQUENCE: 14
tggattagag accctggtag tccacgccgt aaacgatgag tgctaagtgt tagaggcctt 60
tagtgctgaa gttaacgcat taagcactcc gcctggggag tacggcca 108

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
tttcgatgca acgcgaagaa cct 23

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
tacgagctga cgacagccat g 21

<210> SEQ ID NO 17
<211> LENGTH: 108
<212> TYPE: DNA
<213> ORGANISM: Artificial Sequence
<220> FEATURE:
<223> OTHER INFORMATION: Oligonucleotide

<400> SEQUENCE: 17
tttcgatgca acgcgaagaa ccttaccagg tcttgacatc ctctgacaac cctagcttct 60
ccttcgggag cagagtgaca ggtggtgcat ggctgtcgtc agctcgta 108

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18

-continued tctgacacct gcccggtgc 19

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tgaccgttat agttacggcc 20

<210> SEQ ID NO 20
<211> LENGTH: 95
<212> TYPE: DNA
<213> ORGANISM: Artificial Sequence
<220> FEATURE:
<223> OTHER INFORMATION: Oligonucleotide

<400> SEQUENCE: 20
tctgacacct gcccggtgct ggaaggttaa ggagaggggt tagcgtaact ctgaactgaa 60
gccccagtaa acggcggccg taactataac ggtca 95

<210> SEQ ID NO 21
<211> LENGTH: 31
<212> TYPE: DNA
<213> ORGANISM: Artificial Sequence
<220> FEATURE:
<223> OTHER INFORMATION: Primer

<400> SEQUENCE: 21
tgattattgt tatcctgtta tgccatttga g 31

<210> SEQ ID NO 22
<211> LENGTH: 29
<212> TYPE: DNA
<213> ORGANISM: Artificial Sequence
<220> FEATURE:
<223> OTHER INFORMATION: Primer

<400> SEQUENCE: 22
tgtaaccctt gtctttgaat tgtatttgc 29

<210> SEQ ID NO 23
<211> LENGTH: 100
<212> TYPE: DNA
<213> ORGANISM: Artificial Sequence
<220> FEATURE:
<223> OTHER INFORMATION: Oligonucleotide

<400> SEQUENCE: 23
tgattattgt tatcctgtta tgccatttga gatttttgag tggtattgga gttattgttc 60
caggattaat tgcaaataca attcaaagac aagggttaca 100

<210> SEQ ID NO 24
<211> LENGTH: 28
<212> TYPE: DNA
<213> ORGANISM: Artificial Sequence
<220> FEATURE:
<223> OTHER INFORMATION: Primer

<400> SEQUENCE: 24
tcgaagtaca atacaagaca aaagaagg 28

-continued

```
<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25

ttgttaacgg cttcaagacc c                                                21


<210> SEQ ID NO 26
<211> LENGTH: 112
<212> TYPE: DNA
<213> ORGANISM: Artificial Sequence
<220> FEATURE:
<223> OTHER INFORMATION: Oligonucleotide

<400> SEQUENCE: 26

tcgaagtaca atacaagaca aaagaaggta aaattactgt tttaggggaa aaattcaaga      60

aatatagaag tgatggctaa aaatgtagaa ggggtcttga agccgttaac aa             112


<210> SEQ ID NO 27
<211> LENGTH: 30
<212> TYPE: DNA
<213> ORGANISM: Artificial Sequence
<220> FEATURE:
<223> OTHER INFORMATION: Primer

<400> SEQUENCE: 27

ttgctcgtgg tgcacaagta acggatatta                                       30


<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28

ttgctgcttt cgcatggtta attgcttcaa                                       30


<210> SEQ ID NO 29
<211> LENGTH: 100
<212> TYPE: DNA
<213> ORGANISM: Artificial Sequence
<220> FEATURE:
<223> OTHER INFORMATION: Oligonucleotide

<400> SEQUENCE: 29

ttgctcgtgg tgcacaagta acggatatta caatcattgt tgttgcagct gatgacggcg      60

taataaacag ttgaagcaat taaccatgcg aaagcagcaa                           100


<210> SEQ ID NO 30
<211> LENGTH: 27
<212> TYPE: DNA
<213> ORGANISM: Artificial Sequence
<220> FEATURE:
<223> OTHER INFORMATION: Primer

<400> SEQUENCE: 30

tagcttttgc atattatatc gagccac                                          27


<210> SEQ ID NO 31
<211> LENGTH: 31
```

-continued

```
<212> TYPE: DNA
<213> ORGANISM: Artificial Sequence
<220> FEATURE:
<223> OTHER INFORMATION: Primer

<400> SEQUENCE: 31

ttcttccaag gatagattta tttcttgttc g                                31


<210> SEQ ID NO 32
<211> LENGTH: 114
<212> TYPE: DNA
<213> ORGANISM: Artificial Sequence
<220> FEATURE:
<223> OTHER INFORMATION: Oligonucleotide

<400> SEQUENCE: 32

tagcttttgc atattatatc gagccacagc atcgtgatgt tttacagctt tatgcaccgg     60

aagcttttaa tggataaatt taacgaacaa gaaataaatc tatccttgga agaa         114


<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33

tctggcaggt atgcgtggtc tgatg                                       25


<210> SEQ ID NO 34
<211> LENGTH: 26
<212> TYPE: DNA
<213> ORGANISM: Artificial Sequence
<220> FEATURE:
<223> OTHER INFORMATION: Primer

<400> SEQUENCE: 34

tcgcaccgtg ggttgagatg aagtac                                      26


<210> SEQ ID NO 35
<211> LENGTH: 117
<212> TYPE: DNA
<213> ORGANISM: Artificial Sequence
<220> FEATURE:
<223> OTHER INFORMATION: Oligonucleotide

<400> SEQUENCE: 35

tctggcaggt atgcgtggtc tgatggccaa tccatctggt cgtatcatcg aacttccaat     60

caagtttccg tgaaggttta acagtacttg agtacttcat ctcaacccac ggtgcga      117


<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36

tcaagcaaac gcacaatcag aagc                                        24


<210> SEQ ID NO 37
<211> LENGTH: 27
<212> TYPE: DNA
<213> ORGANISM: Artificial Sequence
<220> FEATURE:
```

-continued

<223> OTHER INFORMATION: Primer

<400> SEQUENCE: 37
ttgcacgtct gtttcagttg caaattc 27

<210> SEQ ID NO 38
<211> LENGTH: 98
<212> TYPE: DNA
<213> ORGANISM: Artificial Sequence
<220> FEATURE:
<223> OTHER INFORMATION: Oligonucleotide

<400> SEQUENCE: 38
tcaagcaaac gcacaatcag aagctaagaa agcgcaagct tctggaaagc acaaatgcta 60
gttatggtac agaatttgca actgaaacag acgtgcaa 98

<210> SEQ ID NO 39
<211> LENGTH: 31
<212> TYPE: DNA
<213> ORGANISM: Artificial Sequence
<220> FEATURE:
<223> OTHER INFORMATION: Primer

<400> SEQUENCE: 39
tgacctacag taagaggttc tgtaatgaac c 31

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
ttccaagtgc tggtttaccc catgg 25

<210> SEQ ID NO 41
<211> LENGTH: 116
<212> TYPE: DNA
<213> ORGANISM: Artificial Sequence
<220> FEATURE:
<223> OTHER INFORMATION: Oligonucleotide

<400> SEQUENCE: 41
tgacctacag taagaggttc tgtaatgaac cctaatgacc atccacacgg tggtggtgaa 60
ggtagatctc ctatcggaaa gtccacgtac tccatggggt aaaccagcac ttggaa 116

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
tcgtggcggc gtggttatcg a 21

<210> SEQ ID NO 43
<211> LENGTH: 25
<212> TYPE: DNA
<213> ORGANISM: Artificial Sequence
<220> FEATURE:
<223> OTHER INFORMATION: Primer

<400> SEQUENCE: 43

-continued tcggtacgaa ctggatgtcg ccgtt 25

<210> SEQ ID NO 44
<211> LENGTH: 111
<212> TYPE: DNA
<213> ORGANISM: Artificial Sequence
<220> FEATURE:
<223> OTHER INFORMATION: Oligonucleotide

<400> SEQUENCE: 44
tcgtggcggc gtggttatcg aacccatgct gaccgatcaa tggtacgtgc acaccgcccc 60
ccaaagtcgc gattgaagcc gtagagaacg gcgacatcca gttcgtaccg a 111

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
ttatcgctca ggcgaactcc aac 23

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
tgctggattc gcctttgcta cg 22

<210> SEQ ID NO 47
<211> LENGTH: 82
<212> TYPE: DNA
<213> ORGANISM: Artificial Sequence
<220> FEATURE:
<223> OTHER INFORMATION: Oligonucleotide

<400> SEQUENCE: 47
ttatcgctca ggcgaactcc aacctggatg atgaaggccg ctttttagaa ggtgacttgt 60
cgtagcaaag gcgaatccag ca 82

<210> SEQ ID NO 48
<211> LENGTH: 23
<212> TYPE: DNA
<213> ORGANISM: Artificial Sequence
<220> FEATURE:
<223> OTHER INFORMATION: Primer

<400> SEQUENCE: 48
tctgttctta gtacgagagg acc 23

<210> SEQ ID NO 49
<211> LENGTH: 22
<212> TYPE: DNA
<213> ORGANISM: Artificial Sequence
<220> FEATURE:
<223> OTHER INFORMATION: Primer

<400> SEQUENCE: 49
tttcgtgctt agatgctttc ag 22

-continued

<210> SEQ ID NO 50
<211> LENGTH: 117
<212> TYPE: DNA
<213> ORGANISM: Artificial Sequence
<220> FEATURE:
<223> OTHER INFORMATION: Oligonucleotide

<400> SEQUENCE: 50
tctgttctta gtacgagagg accgggatgg acgcaccggt accagttgtt ctgccaaggg 60
catagctggg tagctatgtg cggaagggat aagtgctgaa agcatctaag cacgaaa 117

<210> SEQ ID NO 51
<211> LENGTH: 23
<212> TYPE: DNA
<213> ORGANISM: Artificial Sequence
<220> FEATURE:
<223> OTHER INFORMATION: Primer

<400> SEQUENCE: 51
tttaagtccc gcaacgagcg caa 23

<210> SEQ ID NO 52
<211> LENGTH: 23
<212> TYPE: DNA
<213> ORGANISM: Artificial Sequence
<220> FEATURE:
<223> OTHER INFORMATION: Primer

<400> SEQUENCE: 52
ttgacgtcat ccccaccttc ctc 23

<210> SEQ ID NO 53
<211> LENGTH: 102
<212> TYPE: DNA
<213> ORGANISM: Artificial Sequence
<220> FEATURE:
<223> OTHER INFORMATION: Oligonucleotide

<400> SEQUENCE: 53
tttaagtccc gcaacgagcg caacccttga tcttagttgt ttagttgggc actctaaggt 60
gactgccggt gacaaaccgg aggaaggtgg ggatgacgtc aa 102

<210> SEQ ID NO 54
<211> LENGTH: 24
<212> TYPE: DNA
<213> ORGANISM: Artificial Sequence
<220> FEATURE:
<223> OTHER INFORMATION: Primer

<400> SEQUENCE: 54
tgggcagcgt ttcggcgaaa tgga 24

<210> SEQ ID NO 55
<211> LENGTH: 28
<212> TYPE: DNA
<213> ORGANISM: Artificial Sequence
<220> FEATURE:
<223> OTHER INFORMATION: Primer

<400> SEQUENCE: 55
tgtccgactt gacggtcaac atttcctg 28

<210> SEQ ID NO 56
<211> LENGTH: 87

-continued

<212> TYPE: DNA
<213> ORGANISM: Artificial Sequence
<220> FEATURE:
<223> OTHER INFORMATION: Oligonucleotide

<400> SEQUENCE: 56
tgggcagcgt ttcggcgaaa tggaagtggc tcgaagcgta tggcgcttcg tacgtgctgc 60
aggaaatgtt gaccgtcaag tcggaca 87

<210> SEQ ID NO 57
<211> LENGTH: 30
<212> TYPE: DNA
<213> ORGANISM: Artificial Sequence
<220> FEATURE:
<223> OTHER INFORMATION: Primer

<400> SEQUENCE: 57
tcaggagtcg ttcaactcga tctacatgat 30

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
tacgccatca ggccacgcat 20

<210> SEQ ID NO 59
<211> LENGTH: 97
<212> TYPE: DNA
<213> ORGANISM: Artificial Sequence
<220> FEATURE:
<223> OTHER INFORMATION: Oligonucleotide

<400> SEQUENCE: 59
tcaggagtcg ttcaactcga tctacatgat ggccgaccgc ccggggttcg gcggtgcaga 60
ttcgtcagct ggccggcatg cgtggcctga tggcgta 97

<210> SEQ ID NO 60
<211> LENGTH: 24
<212> TYPE: DNA
<213> ORGANISM: Artificial Sequence
<220> FEATURE:
<223> OTHER INFORMATION: Primer

<400> SEQUENCE: 60
tccacacgcc gttcttcaac aact 24

<210> SEQ ID NO 61
<211> LENGTH: 26
<212> TYPE: DNA
<213> ORGANISM: Artificial Sequence
<220> FEATURE:
<223> OTHER INFORMATION: Primer

<400> SEQUENCE: 61
tggcatcacc atttccttgt ccttcg 26

<210> SEQ ID NO 62
<211> LENGTH: 99
<212> TYPE: DNA
<213> ORGANISM: Artificial Sequence
<220> FEATURE:

-continued

<223> OTHER INFORMATION: Oligonucleotide

<400> SEQUENCE: 62
tccacacgcc gttcttcaac aactaccgtg ttctacttcc gtacgacgga cgtgacgggc 60
tcgatcgagc tgccgaagga caaggaaatg gtgatgcca 99

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
tccacacggt ggtggtgaag g 21

<210> SEQ ID NO 64
<211> LENGTH: 22
<212> TYPE: DNA
<213> ORGANISM: Artificial Sequence
<220> FEATURE:
<223> OTHER INFORMATION: Primer

<400> SEQUENCE: 64
tgtgctggtt taccccatgg ag 22

<210> SEQ ID NO 65
<211> LENGTH: 70
<212> TYPE: DNA
<213> ORGANISM: Artificial Sequence
<220> FEATURE:
<223> OTHER INFORMATION: Oligonucleotide

<400> SEQUENCE: 65
tccacacggt ggtggtgaag gtagatctcc tatcggaaag tccacgtact ccatggggta 60
aaccagcaca 70

<210> SEQ ID NO 66
<211> LENGTH: 1542
<212> TYPE: DNA
<213> ORGANISM: E. coli

<400> SEQUENCE: 66
aaattgaaga gtttgatcat ggctcagatt gaacgctggc ggcaggccta acacatgcaa 60
gtcgaacggt aacaggaaga agcttgcttc tttgctgacg agtggcggac gggtgagtaa 120
tgtctgggaa actgcctgat ggagggggat aactactgga aacggtagct aataccgcat 180
aacgtcgcaa gaccaaagag ggggaccttc gggcctcttg ccatcggatg tgcccagatg 240
ggattagcta gtaggtgggg taacggctca cctaggcgac gatccctagc tggtctgaga 300
ggatgaccag ccacactgga actgagacac ggtccagact cctacgggag gcagcagtgg 360
ggaatattgc acaatgggcg caagcctgat gcagccatgc cgcgtgtatg aagaaggcct 420
tcgggttgta aagtactttc agcggggagg aagggagtaa agttaatacc tttgctcatt 480
gacgttaccc gcagaagaag caccggctaa ctccgtgcca gcagccgcgg taatacggag 540
ggtgcaagcg ttaatcggaa ttactgggcg taaagcgcac gcaggcggtt tgttaagtca 600
gatgtgaaat ccccgggctc aacctgggaa ctgcatctga tactggcaag cttgagtctc 660
gtagaggggg gtagaattcc aggtgtagcg gtgaaatgcg tagagatctg gaggaatacc 720
ggtggcgaag gcggccccct ggacgaagac tgacgctcag gtgcgaaagc gtggggagca 780

```
aacaggatta gataccctgg tagtccacgc cgtaaacgat gtcgacttgg aggttgtgcc    840

cttgaggcgt ggcttccgga gctaacgcgt taagtcgacc gcctggggag tacggccgca    900

aggttaaaac tcaaatgaat tgacgggggc ccgcacaagc ggtggagcat gtggtttaat    960

tcgatgcaac gcgaagaacc ttacctggtc ttgacatcca cggaagtttt cagagatgag   1020

aatgtgcctt cgggaaccgt gagacaggtg ctgcatggct gtcgtcagct cgtgttgtga   1080

aatgttgggt taagtcccgc aacgagcgca acccttatcc tttgttgcca gcggtccggc   1140

cgggaactca aaggagactg ccagtgataa actggaggaa ggtggggatg acgtcaagtc   1200

atcatggccc ttacgaccag ggctacacac gtgctacaat ggcgcataca aagagaagcg   1260

acctcgcgag agcaagcgga cctcataaag tgcgtcgtag tccggattgg agtctgcaac   1320

tcgactccat gaagtcggaa tcgctagtaa tcgtggatca gaatgccacg gtgaatacgt   1380

tcccgggcct tgtacacacc gcccgtcaca ccatgggagt gggttgcaaa agaagtaggt   1440

agcttaacct tcgggagggc gcttaccact ttgtgattca tgactggggt gaagtcgtaa   1500

caaggtaacc gtaggggaac ctgcggttgg atcacctcct ta                       1542
```

<210> SEQ ID NO 67
<211> LENGTH: 2904
<212> TYPE: DNA
<213> ORGANISM: E. coli

<400> SEQUENCE: 67

```
ggttaagcga ctaagcgtac acggtggatg ccctggcagt cagaggcgat gaaggacgtg     60

ctaatctgcg ataagcgtcg gtaaggtgat atgaaccgtt ataaccggcg atttccgaat    120

ggggaaaccc agtgtgtttc gacacactat cattaactga atccataggt taatgaggcg    180

aaccggggga actgaaacat ctaagtaccc cgaggaaaag aaatcaaccg agattccccc    240

agtagcggcg agcgaacggg gagcagccca gagcctgaat cagtgtgtgt gttagtggaa    300

gcgtctggaa aggcgcgcga tacagggtga cagccccgta cacaaaaatg cacatgctgt    360

gagctcgatg agtagggcgg gacacgtggt atcctgtctg aatatggggg gaccatcctc    420

caaggctaaa tactcctgac tgaccgatag tgaaccagta ccgtgaggga aaggcgaaaa    480

gaaccccggc gaggggagtg aaaaagaacc tgaaaccgtg tacgtacaag cagtgggagc    540

acgcttaggc gtgtgactgc gtaccttttg tataatgggt cagcgactta tattctgtag    600

caaggttaac cgaatagggg agccgaaggg aaaccgagtc ttaactgggc gttaagttgc    660

agggtataga cccgaaaccc ggtgatctag ccatgggcag gttgaaggtt gggtaacact    720

aactggagga ccgaaccgac taatgttgaa aaattagcgg atgacttgtg gctgggggtg    780

aaaggccaat caaaccggga gatagctggt tctccccgaa agctatttag gtagcgcctc    840

gtgaattcat ctccgggggt agagcactgt ttcggcaagg gggtcatccc gacttaccaa    900

cccgatgcaa actgcgaata ccggagaatg ttatcacggg agacacacgg cgggtgctaa    960

cgtccgtcgt gaagagggaa acaacccaga ccgccagcta aggtcccaaa gtcatggtta   1020

agtgggaaac gatgtgggaa ggcccagaca gccaggatgt tggcttagaa gcagccatca   1080

tttaaagaaa gcgtaatagc tcactggtcg agtcggcctg cgcggaagat gtaacggggc   1140

taaaccatgc accgaagctg cggcagcgac gcttatgcgt tgttgggtag gggagcgttc   1200

tgtaagcctg cgaaggtgtg ctgtgaggca tgctggaggt atcagaagtg cgaatgctga   1260

cataagtaac gataaagcgg gtgaaaagcc cgctcgccgg aagaccaagg gttcctgtcc   1320
```

-continued

```
aacgttaatc ggggcagggt gagtcgaccc ctaaggcgag gccgaaaggc gtagtcgatg   1380

ggaaacaggt taatattcct gtacttggtg ttactgcgaa ggggggacgg agaaggctat   1440

gttggccggg cgacggttgt cccggtttaa gcgtgtaggc tggttttcca ggcaaatccg   1500

gaaaatcaag gctgaggcgt gatgacgagg cactacggtg ctgaagcaac aaatgccctg   1560

cttccaggaa aagcctctaa gcatcaggta acatcaaatc gtaccccaaa ccgacacagg   1620

tggtcaggta gagaatacca aggcgcttga gagaactcgg gtgaaggaac taggcaaaat   1680

ggtgccgtaa cttcgggaga aggcacgctg atatgtaggt gaggtccctc gcggatggag   1740

ctgaaatcag tcgaagatac cagctggctg caactgttta ttaaaaacac agcactgtgc   1800

aaacacgaaa gtggacgtat acggtgtgac gcctgcccgg tgccggaagg ttaattgatg   1860

gggttagcgc aagcgaagct cttgatcgaa gccccggtaa acggcggccg taactataac   1920

ggtcctaagg tagcgaaatt ccttgtcggg taagttccga cctgcacgaa tggcgtaatg   1980

atggccaggc tgtctccacc cgagactcag tgaaattgaa ctcgctgtga agatgcagtg   2040

tacccgcggc aagacggaaa gaccccgtga acctttacta tagcttgaca ctgaacattg   2100

agccttgatg tgtaggatag gtgggaggct ttgaagtgtg gacgccagtc tgcatggagc   2160

cgaccttgaa ataccaccct ttaatgtttg atgttctaac gttgacccgt aatccgggtt   2220

gcggacagtg tctggtgggt agtttgactg gggcggtctc ctcctaaaga gtaacggagg   2280

agcacgaagg ttggctaatc ctggtcggac atcaggaggt tagtgcaatg gcataagcca   2340

gcttgactgc gagcgtgacg gcgcgagcag gtgcgaaagc aggtcatagt gatccggtgg   2400

ttctgaatgg aagggccatc gctcaacgga taaaaggtac tccggggata acaggctgat   2460

accgcccaag agttcatatc gacggcggtg tttggcacct cgatgtcggc tcatcacatc   2520

ctggggctga agtaggtccc aagggtatgg ctgttcgcca tttaaagtgg tacgcgagct   2580

gggtttagaa cgtcgtgaga cagttcggtc cctatctgcc gtgggcgctg gagaactgag   2640

gggggctgct cctagtacga gaggaccgga gtggacgcat cactggtgtt cgggttgtca   2700

tgccaatggc actgcccggt agctaaatgc ggaagagata agtgctgaaa gcatctaagc   2760

acgaaacttg ccccgagatg agttctccct gaccctttaa gggtcctgaa ggaacgttga   2820

agacgacgac gttgataggc cgggtgtgta agcgcagcga tgcgttgagc taaccggtac   2880

taatgaaccg tgaggcttaa cctt                                           2904
```

<210> SEQ ID NO 68
<211> LENGTH: 4029
<212> TYPE: DNA
<213> ORGANISM: E. coli

<400> SEQUENCE: 68

```
atggtttact cctataccga gaaaaaacgt attcgtaagg attttggtaa acgtccacaa     60

gttctggatg taccttatct cctttctatc cagcttgact cgtttcagaa atttatcgag    120

caagatcctg aagggcagta tggtctggaa gctgctttcc gttccgtatt cccgattcag    180

agctacagcg gtaattccga gctgcaatac gtcagctacc gccttggcga accggtgttt    240

gacgtccagg aatgtcaaat ccgtggcgtg acctattccg caccgctgcg cgttaaactg    300

cgtctggtga tctatgagcg cgaagcgccg gaaggcaccg taaaagacat taaagaacaa    360

gaagtctaca tgggcgaaat tccgctcatg acagacaacg gtacctttgt tatcaacggt    420

actgagcgtg ttatcgtttc ccagctgcac cgtagtccgg gcgtcttctt tgactccgac    480

aaaggtaaaa cccactcttc gggtaaagtg ctgtataacg cgcgtatcat cccttaccgt    540
```

-continued

```
ggttcctggc tggacttcga attcgatccg aaggacaacc tgttcgtacg tatcgaccgt    600
cgccgtaaac tgcctgcgac catcattctg cgcgccctga actacaccac agagcagatc    660
ctcgacctgt tctttgaaaa agttatcttt gaaatccgtg ataacaagct gcagatggaa    720
ctggtgccgg aacgcctgcg tggtgaaacc gcatcttttg acatcgaagc taacggtaaa    780
gtgtacgtag aaaaaggccg ccgtatcact gcgcgccaca ttcgccagct ggaaaaagac    840
gacgtcaaac tgatcgaagt cccggttgag tacatcgcag gtaaagtggt tgctaaagac    900
tatattgatg agtctaccgg cgagctgatc tgcgcagcga acatggagct gagcctggat    960
ctgctggcta agctgagcca gtctggtcac aagcgtatcg aaacgctgtt caccaacgat   1020
ctggatcacg gcccatatat ctctgaaacc ttacgtgtcg acccaactaa cgaccgtctg   1080
agcgcactgg tagaaatcta ccgcatgatg cgccctggcg agccgccgac tcgtgaagca   1140
gctgaaagcc tgttcgagaa cctgttcttc tccgaagacc gttatgactt gtctgcggtt   1200
ggtcgtatga agttcaaccg ttctctgctg cgcgaagaaa tcgaaggttc cggtatcctg   1260
agcaaagacg acatcattga tgttatgaaa aagctcatcg atatccgtaa cggtaaaggc   1320
gaagtcgatg atatcgacca cctcggcaac cgtcgtatcc gttccgttgg cgaaatggcg   1380
gaaaaccagt tccgcgttgg cctggtacgt gtagagcgtg cggtgaaaga gcgtctgtct   1440
ctgggcgatc tggataccct gatgccacag gatatgatca acgccaagcc gatttccgca   1500
gcagtgaaag agttcttcgg ttccagccag ctgtctcagt ttatggacca gaacaacccg   1560
ctgtctgaga ttacgcacaa acgtcgtatc tccgcactcg gcccaggcgg tctgacccgt   1620
gaacgtgcag gcttcgaagt tcgagacgta cacccgactc actacggtcg cgtatgtcca   1680
atcgaaaccc ctgaaggtcc gaacatcggt ctgatcaact ctctgtccgt gtacgcacag   1740
actaacgaat acggcttcct tgagactccg tatcgtaaag tgaccgacgg tgttgtaact   1800
gacgaaattc actacctgtc tgctatcgaa gaaggcaact acgttatcgc ccaggcgaac   1860
tccaacttgg atgaagaagg ccacttcgta gaagacctgg taacttgccg tagcaaaggc   1920
gaatccagct tgttcagccg cgaccaggtt gactacatgg acgtatccac ccagcaggtg   1980
gtatccgtcg gtgcgtccct gatcccgttc ctggaacacg atgacgccaa ccgtgcattg   2040
atgggtgcga acatgcaacg tcaggccgtt ccgactctgc gcgctgataa gccgctggtt   2100
ggtactggta tggaacgtgc tgttgccgtt gactccggtg taactgcggt agctaaacgt   2160
ggtggtgtcg ttcagtacgt ggatgcttcc cgtatcgtta tcaaagttaa cgaagacgag   2220
atgtatccgg gtgaagcagg tatcgacatc tacaacctga ccaaatacac ccgttctaac   2280
cagaacacct gtatcaacca gatgccgtgt gtgtctctgg gtgaaccggt tgaacgtggc   2340
gacgtgctgg cagacggtcc gtccaccgac ctcggtgaac tggcgcttgg tcagaacatg   2400
cgcgtagcgt tcatgccgtg gaatggttac aacttcgaag actccatcct cgtatccgag   2460
cgtgttgttc aggaagaccg tttcaccacc atccacattc aggaactggc gtgtgtgtcc   2520
cgtgacacca agctgggtcc ggaagagatc accgctgaca tcccgaacgt gggtgaagct   2580
gcgctctcca aactggatga atccggtatc gtttacattg gtgcggaagt gaccggtggc   2640
gacattctgg ttggtaaggt aacgccgaaa ggtgaaactc agctgacccc agaagaaaaa   2700
ctgctgcgtg cgatcttcgg tgagaaagcc tctgacgtta aagactcttc tctgcgcgta   2760
ccaaacggtg tatccggtac ggttatcgac gttcaggtct ttactcgcga tggcgtagaa   2820
aaagacaaac gtgcgctgga aatcgaagaa atgcagctca aacaggcgaa gaaagacctg   2880
```

-continued

```
tctgaagaac tgcagatcct cgaagcgggt ctgttcagcc gtatccgtgc tgtgctggta   2940

gccggtggcg ttgaagctga gaagctcgac aaactgccgc gcgatcgctg gctggagctg   3000

ggcctgacag acgaagagaa acaaaatcag ctggaacagc tggctgagca gtatgacgaa   3060

ctgaaacacg agttcgagaa gaaactcgaa gcgaaacgcc gcaaaatcac ccagggcgac   3120

gatctggcac cgggcgtgct gaagattgtt aaggtatatc tggcggttaa acgccgtatc   3180

cagcctggtg acaagatggc aggtcgtcac ggtaacaagg gtgtaatttc taagatcaac   3240

ccgatcgaag atatgcctta cgatgaaaac ggtacgccgg tagacatcgt actgaacccg   3300

ctgggcgtac cgtctcgtat gaacatcggt cagatcctcg aaacccacct gggtatggct   3360

gcgaaaggta tcggcgacaa gatcaacgcc atgctgaaac agcagcaaga agtcgcgaaa   3420

ctgcgcgaat tcatccagcg tgcgtacgat ctgggcgctg acgttcgtca gaaagttgac   3480

ctgagtacct tcagcgatga agaagttatg cgtctggctg aaaacctgcg caaaggtatg   3540

ccaatcgcaa cgccggtgtt cgacggtgcg aaagaagcag aaattaaaga gctgctgaaa   3600

cttggcgacc tgccgacttc cggtcagatc cgcctgtacg atggtcgcac tggtgaacag   3660

ttcgagcgtc cggtaaccgt tggttacatg tacatgctga aactgaacca cctggtcgac   3720

gacaagatgc acgcgcgttc caccggttct tacagcctgg ttactcagca gccgctgggt   3780

ggtaaggcac agttcggtgg tcagcgtttc ggggagatgg aagtgtgggc gctggaagca   3840

tacggcgcag catacaccct gcaggaaatg ctcaccgtta agtctgatga cgtgaacggt   3900

cgtaccaaga tgtataaaaa catcgtggac ggcaaccatc agatggagcc gggcatgcca   3960

gaatccttca acgtattgtt gaaagagatt cgttcgctgg gtatcaacat cgaactggaa   4020

gacgagtaa                                                           4029
```

<210> SEQ ID NO 69
<211> LENGTH: 4096
<212> TYPE: DNA
<213> ORGANISM: E. coli

<400> SEQUENCE: 69

```
gtgaaagatt tattaaagtt tctgaaagcg cagactaaaa ccgaagagtt tgatgcgatc     60

aaaattgctc tggcttcgcc agacatgatc cgttcatggt ctttcggtga agttaaaaag    120

ccggaaacca tcaactaccg tacgttcaaa ccagaacgtg acggcctttt ctgcgcccgt    180

atctttgggc cggtaaaaga ttacgagtgc ctgtgcggta agtacaagcg cctgaaacac    240

cgtggcgtca tctgtgagaa gtgcggcgtt gaagtgaccc agactaaagt acgccgtgag    300

cgtatgggcc acatcgaact ggcttccccg actgcgcaca tctggttcct gaaatcgctg    360

ccgtcccgta tcggtctgct gctcgatatg ccgctgcgcg atatcgaacg cgtactgtac    420

tttgaatcct atgtggttat cgaaggcggt atgaccaacc tggaacgtca gcagatcctg    480

actgaagagc agtatctgga cgcgctggaa gagttcggtg acgaattcga cgcgaagatg    540

ggggcggaag caatccaggc tctgctgaag agcatggatc tggagcaaga gtgcgaacag    600

ctgcgtgaag agctgaacga aaccaactcc gaaaccaagc gtaaaaagct gaccaagcgt    660

atcaaactgc tggaagcgtt cgttcagtct ggtaacaaac cagagtggat gatcctgacc    720

gttctgccgg tactgccgcc agatctgcgt ccgctggttc cgctggatgg tggtcgtttc    780

gcgacttctg acctgaacga tctgtatcgt cgcgtcatta accgtaacaa ccgtctgaaa    840

cgtctgctgg atctggctgc gccggacatc atcgtacgta acgaaaaacg tatgctgcag    900

gaagcggtag acgccctgct ggataacggt cgtcgcggtc gtgcgatcac cggttctaac    960
```

-continued aagcgtcctc tgaaatcttt ggccgacatg atcaaaggta aacagggtcg tttccgtcag 1020
aacctgctcg gtaagcgtgt tgactactcc ggtcgttctg taatcaccgt aggtccatac 1080
ctgcgtctgc atcagtgcgg tctgccgaag aaaatggcac tggagctgtt caaaccgttc 1140
atctacggca agctggaact gcgtggtctt gctaccacca ttaaagctgc gaagaaaatg 1200
gttgagcgcg aagaagctgt cgtttgggat atcctggacg aagttatccg cgaacacccg 1260
gtactgctga accgtgcacc gactctgcac cgtctgggta tccaggcatt tgaaccggta 1320
ctgatcgaag gtaaagctat ccagctgcac ccgctggttt gtgcggcata taacgccgac 1380
ttcgatggtg accagatggc tgttcacgta ccgctgacgc tggaagccca gctggaagcg 1440
cgtgcgctga tgatgtctac caacaacatc ctgtccccgg cgaacggcga accaatcatc 1500
gttccgtctc aggacgttgt actgggtctg tactacatga cccgtgactg tgttaacgcc 1560
aaaggcgaag gcatggtgct gactggcccg aaagaagcag aacgtctgta tcgctctggt 1620
ctggcttctc tgcatgcgcg cgttaaagtg cgtatcaccg agtatgaaaa agatgctaac 1680
ggtgaattag tagcgaaaac cagcctgaaa gacacgactg ttggccgtgc cattctgtgg 1740
atgattgtac cgaaaggtct gccttactcc atcgtcaacc aggcgctggg taaaaaagca 1800
atctccaaaa tgctgaacac ctgctaccgc attctcggtc tgaaaccgac cgttattttt 1860
gcggaccaga tcatgtacac cggcttcgcc tatgcagcgc gttctggtgc atctgttggt 1920
atcgatgaca tggtcatccc ggagaagaaa cacgaaatca tctccgaggc agaagcagaa 1980
gttgctgaaa ttcaggagca gttccagtct ggtctggtaa ctgcgggcga acgctacaac 2040
aaagttatcg atatctgggc tgcggcgaac gatcgtgtat ccaaagcgat gatggataac 2100
ctgcaaactg aaaccgtgat taaccgtgac ggtcaggaag agaagcaggt ttccttcaac 2160
agcatctaca tgatggccga ctccggtgcg cgtggttctg cggcacagat tcgtcagctt 2220
gctggtatgc gtggtctgat ggcgaagccg gatggctcca tcatcgaaac gccaatcacc 2280
gcgaacttcc gtgaaggtct gaacgtactc cagtacttca tctccaccca cggtgctcgt 2340
aaaggtctgg cggataccgc actgaaaact gcgaactccg gttacctgac tcgtcgtctg 2400
gttgacgtgg cgcaggacct ggtggttacc gaagacgatt gtggtaccca tgaaggtatc 2460
atgatgactc cggttatcga gggtggtgac gttaaagagc cgctgcgcga tcgcgtactg 2520
ggtcgtgtaa ctgctgaaga cgttctgaag ccgggtactg ctgatatcct cgttccgcgc 2580
aacacgctgc tgcacgaaca gtggtgtgac ctgctggaag agaactctgt cgacgcggtt 2640
aaagtacgtt ctgttgtatc ttgtgacacc gactttggtg tatgtgcgca ctgctacggt 2700
cgtgacctgg cgcgtggcca catcatcaac aagggtgaag caatcggtgt tatcgcggca 2760
cagtccatcg gtgaaccggg tacacagctg accatgcgta cgttccacat cggtggtgcg 2820
gcatctcgtg cggctgctga atccagcatc caagtgaaaa acaaaggtag catcaagctc 2880
agcaacgtga agtcggttgt gaactccagc ggtaaactgg ttatcacttc ccgtaatact 2940
gaactgaaac tgatcgacga attcggtcgt actaaagaaa gctacaaagt accttacggt 3000
gcggtactgg cgaaaggcga tggcgaacag gttgctggcg gcgaaaccgt tgcaaactgg 3060
gacccgcaca ccatgccggt tatcaccgaa gtaagcggtt ttgtacgctt tactgacatg 3120
atcgacggcc agaccattac gcgtcagacc gacgaactga ccggtctgtc ttcgctggtg 3180
gttctggatt ccgcagaacg taccgcaggt ggtaaagatc tgcgtccggc actgaaaatc 3240
gttgatgctc agggtaacga cgttctgatc ccaggtaccg atatgccagc gcagtacttc 3300

-continued

```
ctgccgggta aagcgattgt tcagctggaa gatggcgtac agatcagctc tggtgacacc   3360

ctggcgcgta ttccgcagga atccggcggt accaaggaca tcaccggtgg tctgccgcgc   3420

gttgcggacc tgttcgaagc acgtcgtccg aaagagccgg caatcctggc tgaaatcagc   3480

ggtatcgttt ccttcggtaa agaaaccaaa ggtaaacgtc gtctggttat caccccggta   3540

gacggtagcg atccgtacga agagatgatt ccgaaatggc gtcagctcaa cgtgttcgaa   3600

ggtgaacgtg tagaacgtgg tgacgtaatt tccgacggtc cggaagcgcc gcacgacatt   3660

ctgcgtctgc gtggtgttca tgctgttact cgttacatcg ttaacgaagt acaggacgta   3720

taccgtctgc agggcgttaa gattaacgat aaacacatcg aagttatcgt tcgtcagatg   3780

ctgcgtaaag ctaccatcgt taacgcgggt agctccgact tcctggaagg cgaacaggtt   3840

gaatactctc gcgtcaagat cgcaaaccgc gaactggaag cgaacggcaa agtgggtgca   3900

acttactccc gcgatctgct gggtatcacc aaagcgtctc tggcaaccga gtccttcatc   3960

tccgcggcat cgttccagga gaccactcgc gtgctgaccg aagcagccgt tgcgggcaaa   4020

cgcgacgaac tgcgcggcct gaaagagaac gttatcgtgg gtcgtctgat cccggcaggt   4080

accggttacg cgtacc                                                   4096
```

<210> SEQ ID NO 70
<211> LENGTH: 128
<212> TYPE: DNA
<213> ORGANISM: E. coli

<400> SEQUENCE: 70

```
accaggatcg tatgcgtcgc cgtgctgcgg gtgaagctcc ggctgcaccg caggtgactg     60

cagaagacgc atctgccagc ctggcagaac tgctgaacgc aggtctgggc ggttctgata    120

acgagtaa                                                             128
```

<210> SEQ ID NO 71
<211> LENGTH: 1185
<212> TYPE: DNA
<213> ORGANISM: E. coli

<400> SEQUENCE: 71

```
atgtctaaag aaaagtttga acgtacaaaa ccgcacgtta acgtcggtac tatcggccac     60

gttgaccatg gtaaaacaac gctgaccgct gcaatcacta ccgtactggc taaaacctac    120

ggcggtgctg ctcgcgcatt cgaccagatc gataacgcgc cggaagaaaa agctcgtggt    180

atcaccatca acacttctca cgttgaatac gacaccccga cccgtcacta cgcacacgta    240

gactgcccgg ggcacgccga ctatgttaaa aacatgatca ccggtgctgc gcagatggac    300

ggcgcgatcc tggtagttgc tgcgactgac ggcccgatgc cgcagactcg tgagcacatc    360

ctgctgggtc gtcaggtagg cgttccgtac atcatcgtgt tcctgaacaa atgcgacatg    420

gttgatgacg aagagctgct ggaactggtt gaaatggaag ttcgtgaact tctgtctcag    480

tacgacttcc cgggcgacga cactccgatc gttcgtggtt ctgctctgaa agcgctggaa    540

ggcgacgcag agtgggaagc gaaaatcctg gaactggctg gcttcctgga ttcttacatt    600

ccggaaccag agcgtgcgat tgacaagccg ttcctgctgc cgatcgaaga cgtattctcc    660

atctccggtc gtggtaccgt tgttaccggt cgtgtagaac gcggtatcat caaagttggt    720

gaagaagttg aaatcgttgg tatcaaagag actcagaagt ctacctgtac tggcgttgaa    780

atgttccgca aactgctgga cgaaggccgt gctggtgaga acgtaggtgt tctgctgcgt    840

ggtatcaaac gtgaagaaat cgaacgtggt caggtactgg ctaagccggg caccatcaag    900
```

-continued

```
ccgcacacca agttcgaatc tgaagtgtac attctgtcca aagatgaagg cggccgtcat    960

actccgttct tcaaaggcta ccgtccgcag ttctacttcc gtactactga cgtgactggt   1020

accatcgaac tgccggaagg cgtagagatg gtaatgccgg gcgacaacat caaaatggtt   1080

gttaccctga tccacccgat cgcgatggac gacggtctgc gtttcgcaat ccgtgaaggc   1140

ggccgtaccg ttggcgcggg cgttgtagca aaagttctga gctaa                   1185
```

```
<210> SEQ ID NO 72
<211> LENGTH: 822
<212> TYPE: DNA
<213> ORGANISM: E. coli

<400> SEQUENCE: 72

atggcagttg ttaaatgtaa accgacatct ccgggtcgtc gccacgtagt taaagtggtt     60

aaccctgagc tgcacaaggg caaacctttt gctccgttgc tggaaaaaaa cagcaaatcc    120

ggtggtcgta acaacaatgg ccgtatcacc actcgtcata tcggtggtgg ccacaagcag    180

gcttaccgta ttgttgactt caaacgcaac aaagacggta tcccggcagt tgttgaacgt    240

cttgagtacg atccgaaccg ttccgcgaac atcgcgctgg ttctgtacaa agacggtgaa    300

cgccgttaca tcctggcccc taaaggcctg aaagctggcg accagattca gtctggcgtt    360

gatgctgcaa tcaaaccagg taacaccctg ccgatgcgca acatcccggt tggttctact    420

gttcataacg tagaaatgaa accaggtaaa ggcggtcagc tggcacgttc cgctggtact    480

tacgttcaga tcgttgctcg tgatggtgct tatgtcaccc tgcgtctgcg ttctggtgaa    540

atgcgtaaag tagaagcaga ctgccgtgca actctgggcg aagttggcaa tgctgagcat    600

atgctgcgcg ttctgggtaa agcaggtgct gcacgctggc gtggtgttcg tccgaccgtt    660

cgcggtaccg cgatgaaccc ggtagaccac ccacatggtg gtggtgaagg tcgtaacttt    720

ggtaagcacc cggtaactcc gtggggcgtt cagaccaaag gtaagaagac ccgcagcaac    780

aagcgtactg ataaattcat cgtacgtcgc cgtagcaaat aa                       822
```

```
<210> SEQ ID NO 73
<211> LENGTH: 2856
<212> TYPE: DNA
<213> ORGANISM: E. coli

<400> SEQUENCE: 73

atggaaaaga catataaccc acaagatatc gaacagccgc tttacgagca ctgggaaaag     60

cagggctact ttaagcctaa tggcgatgaa agccaggaaa gtttctgcat catgatcccg    120

ccgccgaacg tcaccggcag tttgcatatg ggtcacgcct tccagcaaac catcatggat    180

accatgatcc gctatcagcg catgcagggc aaaaacaccc tgtggcaggt cggtactgac    240

cacgccggga tcgctaccca gatggtcgtt gagcgcaaga ttgccgcaga agaaggtaaa    300

acccgtcacg actacggccg cgaagctttc atcgacaaaa tctgggaatg gaaagcggaa    360

tctggcggca ccattacccg tcagatgcgc cgtctcggca actccgtcga ctgggagcgt    420

gaacgcttca ccatggacga aggcctgtcc aatgcggtga aagaagtttt cgttcgtctg    480

tataaagaag acctgattta ccgtggcaaa cgcctggtaa actgggatcc gaaactgcgc    540

accgctatct ctgacctgga agtcgaaaac cgcgaatcga aaggttcgat gtggcacatc    600

cgctatccgc tggctgacgg tgcgaaaacc gcagacggta aagattatct ggtggtcgcg    660

actacccgtc cagaaaccct gctgggcgat actggcgtag ccgttaaccc ggaagatccg    720
```

-continued

```
cgttacaaag atctgattgg caaatatgtc attctgccgc tggttaaccg tcgtattccg    780

atcgttggcg acgaacacgc cgacatggaa aaaggcaccg gctgcgtgaa aatcactccg    840

gcgcacgact ttaacgacta tgaagtgggt aaacgtcacg ccctgccgat gatcaacatc    900

ctgacctttg acggcgatat ccgtgaaagc gcccaggtgt tcgataccaa aggtaacgaa    960

tctgacgttt attccagcga aatccctgca gagttccaga aactggagcg ttttgctgca   1020

cgtaaagcag tcgttgccgc agttgacgcg cttggcctgc tggaagaaat taaaccgcac   1080

gacctgaccg ttccttacgg cgaccgtggc ggcgtagtta tcgaaccaat gctgaccgac   1140

cagtggtacg tgcgtgccga tgtcctggcg aaaccggcgg ttgaagcggt tgagaacggc   1200

gacattcagt tcgtaccgaa gcagtacgaa aacatgtact tctcctggat gcgcgatatt   1260

caggactggt gtatctctcg tcagttgtgg tggggtcacc gtatcccggc atggtatgac   1320

gaagcgggta acgtttatgt tggccgcaac gaagacgaag tgcgtaaaga aaataacctc   1380

ggtgctgatg ttgtcctgcg tcaggacgaa gacgttctcg atacctggtt ctcttctgcg   1440

ctgtggacct tctctaccct tggctggccg gaaaataccg acgccctgcg tcagttccac   1500

ccaaccagcg tgatggtatc tggtttcgac atcattttct tctggattgc ccgcatgatc   1560

atgatgacca tgcacttcat caaagatgaa aatggcaaac cgcaggtgcc gttccacacc   1620

gtttacatga ccggcctgat tcgtgatgac gaaggccaga agatgtccaa atccaagggt   1680

aacgttatcg acccactgga tatggttgac ggtatttcgc tgccagaact gctggaaaaa   1740

cgtaccggca atatgatgca gccgcagctg gcggacaaaa tccgtaagcg caccgagaag   1800

cagttcccga acggtattga gccgcacggt actgacgcgc tgcgcttcac cctggcggcg   1860

ctggcgtcta ccggtcgtga catcaactgg gatatgaagc gtctggaagg ttaccgtaac   1920

ttctgtaaca agctgtggaa cgccagccgc tttgtgctga tgaacacaga aggtcaggat   1980

tgcggcttca acggcggcga aatgacgctg tcgctggcgg accgctggat tctggcggag   2040

ttcaaccaga ccatcaaagc gtaccgcgaa gcgctggaca gcttccgctt cgatatcgcc   2100

gcaggcattc tgtatgagtt cacctggaac cagttctgtg actggtatct cgagctgacc   2160

aagccggtaa tgaacggtgg caccgaagca gaactgcgcg gtactcgcca tacgctggtg   2220

actgtactgg aaggtctgct gcgcctcgcg catccgatca ttccgttcat caccgaaacc   2280

atctggcagc gtgtgaaagt actttgcggt atcactgccg acaccatcat gctgcagccg   2340

ttcccgcagt acgatgcatc tcaggttgat gaagccgcac tggccgacac cgaatggctg   2400

aaacaggcga tcgttgcggt acgtaacatc cgtgcagaaa tgaacatcgc gccgggcaaa   2460

ccgctggagc tgctgctgcg tggttgcagc gcggatgcag aacgtcgcgt aaatgaaaac   2520

cgtggcttcc tgcaaaccct ggcgcgtctg gaaagtatca ccgtgctgcc tgccgatgac   2580

aaaggtccgg tttccgttac gaagatcatc gacggtgcag agctgctgat cccgatggct   2640

ggcctcatca acaaagaaga tgagctggcg cgtctggcga aagaagtggc gaagattgaa   2700

ggtgaaatca gccgtatcga gaacaaactg gcgaacgaag gctttgtcgc ccgcgcaccg   2760

gaagcggtca tcgcgaaaga gcgtgagaag ctggaaggct atgcggaagc gaaagcgaaa   2820

ctgattgaac agcaggctgt tatcgccgcg ctgtaa                             2856
```

<210> SEQ ID NO 74
<211> LENGTH: 447
<212> TYPE: DNA
<213> ORGANISM: B. anthracis

<400> SEQUENCE: 74

-continued

```
atgtttggat cagatttata tattgcatta gtattaggag ttacactgag ccttattttt     60

acagaaagaa caggtatttt acctgcaggt ttagttgtac ctggttattt agcactcgtt    120

tttaatcagc ccgtatttat gttggttgtt ttatttatca gtattttaac atatgtaatc    180

gttacgtatg gtgtttcaag attcatgatt ttatatggcc gtagaaaatt tgcggcaacg    240

ctaattacag gtatttgttt aaaactttta tttgattatt gttatcctgt tatgccattt    300

gagatttttg aattccgtgg tattggagtt attgttccag gattaattgc aaatacaatt    360

caaagacaag ggttaccatt aacaattgga actacaattt tgttaagtgg tgcaacattt    420

gcaatcatga atatttatta cttattt                                        447
```

<210> SEQ ID NO 75
<211> LENGTH: 2339
<212> TYPE: DNA
<213> ORGANISM: B. anthracis

<400> SEQUENCE: 75

```
atgactagaa ataaatttat acctaataag tttagtatta tatccttttc agtattacta     60

tttgctatat cctcctcaca ggctatagaa gtaaatgcta tgaatgaaca ttacactgag    120

agtgatatta aaagaaacca taaaactgaa aaaaataaaa ctgaaaaaga aaaatttaaa    180

gacagtatta ataacttagt taaaacagaa tttaccaatg aaactttaga taaaatacag    240

cagacacaag acttattaaa aaagatacct aaggatgtac ttgaaattta tagtgaatta    300

ggaggagaaa tctattttac agatatagat ttagtagaac ataaggagtt acaagattta    360

agtgaagaag agaaaaatag tatgaatagt agaggtgaaa aagttccgtt tgcatcccgt    420

tttgtatttg aaaagaaaag ggaaacacct aaattaatta taaatatcaa agattatgca    480

attaatagtg aacaaagtaa agaagtatat tatgaaattg gaaaggggat ttctcttgat    540

attataagta aggataaatc tctagatcca gagtttttaa atttaattaa gagtttaagc    600

gatgatagtg atagtagcga ccttttattt agtcaaaaat ttaaagagaa gctagaattg    660

aataataaaa gtatagatat aaattttata aaagaaaatt taactgaatt tcagcatgcg    720

ttttctttag cgttttctta ttattttgca cctgaccata gaacggtatt agagttatat    780

gcccccgaca tgtttgagta tatgaataag ttagaaaaag ggggatttga gaaaataagt    840

gaaagtttga agaaagaagg tgtggaaaaa gataggattg atgtgctgaa aggagaaaaa    900

gcacttaaag cttcaggttt agtaccagaa catgcagatg cttttaaaaa aattgctaga    960

gaattaaata catatattct ttttaggcct gttaataagt tagctacaaa ccttattaaa   1020

agtggtgtgg ctacaaaggg attgaatgtt catggaaaga gttcggattg ggggccctgta  1080

gctggataca taccatttga tcaagattta tctaagaagc atggtcaaca attagctgtc   1140

gagaaaggaa atttagaaaa taaaaaatca attacagagc atgaaggtga aataggtaaa   1200

ataccattaa agttagacca tttaagaata gaagagttaa aggaaaatgg gataattttg   1260

aagggtaaaa aagaaattga taatggtaaa aaatattatt tgttagaatc gaataatcag   1320

gtatatgaat ttagaattag cgatgaaaac aacgaagtac aatacaagac aaaagaaggt   1380

aaaattactg ttttagggga aaaattcaat tggagaaata tagaagtgat ggctaaaaat   1440

gtagaagggg tcttgaagcc gttaacagct gactatgatt tatttgcact tgccccaagt   1500

ttaacagaaa taaaaaaaca aataccacaa aaagaatggg ataaagtagt taacacccca   1560

aattcattag aaaagcaaaa aggtgttact aatttattga ttaaatatgg aattgagagg   1620
```

-continued

```
aaaccggatt caactaaggg aactttatca aattggcaaa aacaaatgct tgatcgtttg   1680

aatgaagcag tcaaatatac aggatataca gggggggatg tggttaacca tggcacagag   1740

caagataatg aagagtttcc tgaaaaagat aacgaaattt ttataattaa tccagaaggt   1800

gaatttatat taactaaaaa ttgggagatg acaggtagat ttatagaaaa aaacattacg   1860

ggaaaagatt atttatatta ttttaaccgt tcttataata aaatagctcc tggtaataaa   1920

gcttatattg agtggactga tccgattaca aaagccaaaa taaataccat ccctacgtca   1980

gcagagttta taaaaaactt atccagtatc agaagatctt caaatgtagg agtttataaa   2040

gatagtggcg acaaagacga atttgcaaaa aaagaaagcg tgaaaaaaat tgcaggatat   2100

ttgtcagact attacaattc agcaaatcat atttttctc aggaaaaaaa gcgtaaaata   2160

tcaatatttc gtggaatcca agcctataat gaaattgaaa atgttctaaa atctaaacaa   2220

atagcaccag aatacaaaaa ttattttcaa tatttaaagg aaaggattac caatcaagtt   2280

caattgcttc taacacatca aaaatctaat attgaattta aattattgta taaacaatt    2339
```

```
<210> SEQ ID NO 76
<211> LENGTH: 2480
<212> TYPE: DNA
<213> ORGANISM: B. anthracis

<400> SEQUENCE: 76

atgaatataa aaaaagaatt tataaaagta attagtatgt catgtttagt aacagcaatt     60

actttgagtg gtcccgtctt tatccccctt gtacaggggg cgggcggtca tggtgatgta    120

ggtatgcacg taaaagagaa agagaaaaat aaagatgaga ataagagaaa agatgaagaa    180

cgaaataaaa cacaggaaga gcatttaaag gaaatcatga aacacattgt aaaaatagaa    240

gtaaaagggg aggaagctgt taaaaaagag gcagcagaaa agctacttga gaaagtacca    300

tctgatgttt tagagatgta taaagcaatt ggaggaaaga tatatattgt ggatggtgat    360

attacaaaac atatatcttt agaagcatta tctgaagata agaaaaaaat aaaagacatt    420

tatgggaaag atgctttatt acatgaacat tatgtatatg caaaagaagg atatgaaccc    480

gtacttgtaa tccaatcttc ggaagattat gtagaaaata ctgaaaaggc actgaacgtt    540

tattatgaaa taggtaagat attatcaagg gatattttaa gtaaaattaa tcaaccatat    600

cagaaatttt tagatgtatt aaataccatt aaaaatgcat ctgattcaga tggacaagat    660

cttttattta ctaatcagct taaggaacat cccacagact tttctgtaga attcttggaa    720

caaaatagca atgaggtaca agaagtattt gcgaaagctt ttgcatatta tatcgagcca    780

cagcatcgtg atgttttaca gctttatgca ccggaagctt ttaattacat ggataaattt    840

aacgaacaag aaataaatct atccttggaa gaacttaaag atcaacggat gctgtcaaga    900

tatgaaaaat gggaaaagat aaaacagcac tatcaacact ggagcgattc tttatctgaa    960

gaaggaagag gacttttaaa aaagctgcag attcctattg agccaaagaa agatgacata   1020

attcattctt tatctcaaga agaaaaagag cttctaaaaa gaatacaaat tgatagtagt   1080

gatttttat ctactgagga aaaagagttt ttaaaaaagc tacaaattga tattcgtgat   1140

tctttatctg aagaagaaaa agagctttta aatagaatac aggtggatag tagtaatcct   1200

ttatctgaaa aagaaaaaga gtttttaaaa aagctgaaac ttgatattca accatatgat   1260

attaatcaaa ggttgcaaga tacaggaggg ttaattgata gtccgtcaat taatcttgat   1320

gtaagaaagc agtataaaag ggatattcaa aatattgatg ctttattaca tcaatccatt   1380

ggaagtacct tgtacaataa aatttatttg tatgaaaata tgaatatcaa taaccttaca   1440
```

-continued

```
gcaaccctag gtgcggattt agttgattcc actgataata ctaaaattaa tagaggtatt   1500

ttcaatgaat tcaaaaaaaa tttcaaatat agtatttcta gtaactatat gattgttgat   1560

ataaatgaaa ggcctgcatt agataatgag cgtttgaaat ggagaatcca attatcacca   1620

gatactcgag caggatattt agaaaatgga aagcttatat tacaaagaaa catcggtctg   1680

gaaataaagg atgtacaaat aattaagcaa tccgaaaaag aatatataag gattgatgcg   1740

aaagtagtgc caaagagtaa aatagataca aaaattcaag aagcacagtt aaatataaat   1800

caggaatgga ataaagcatt agggttacca aaatatacaa agcttattac attcaacgtg   1860

cataatagat atgcatccaa tattgtagaa agtgcttatt taatattgaa tgaatggaaa   1920

aataatattc aaagtgatct tataaaaaag gtaacaaatt acttagttga tggtaatgga   1980

agatttgttt ttaccgatat tactctccct aatatagctg aacaatatac acatcaagat   2040

gagatatatg agcaagttca ttcaaaaggg ttatatgttc cagaatcccg ttctatatta   2100

ctccatggac cttcaaaagg tgtagaatta aggaatgata gtgagggttt tatacacgaa   2160

tttggacatg ctgtggatga ttatgctgga tatctattag ataagaacca atctgattta   2220

gttacaaatt ctaaaaaatt cattgatatt tttaaggaag aagggagtaa tttaacttcg   2280

tatgggagaa caaatgaagc ggaatttttt gcagaagcct ttaggttaat gcattctacg   2340

gaccatgctg aacgtttaaa agttcaaaaa aatgctccga aaactttcca atttattaac   2400

gatcagatta agttcattat taactcataa gtaatgtatt aaaaattttc aaatggattt   2460

aataataata ataataataa                                               2480


<210> SEQ ID NO 77
<211> LENGTH: 288
<212> TYPE: DNA
<213> ORGANISM: B. anthracis

<400> SEQUENCE: 77

atgagtaaaa aacaacaagg ttataacaag gcaacttctg gtgctagcat tcaaagcaca     60

aatgctagtt atggtacaga gtttgcgact gaaacaaatg tacaagcagt aaaacaagca    120

aacgcacaat cagaagctaa gaaagcgcaa gcttctggtg ctagcattca aagcacaaat    180

gctagttatg gtacagaatt tgcaactgaa acagacgtgc atgctgtgaa aaaacaaaat    240

gcacaatcag ctgcaaaaca atcacaatct tctagttcaa atcagtaa                 288
```